(12) United States Patent
Altarac et al.

(10) Patent No.: US 12,035,947 B2
(45) Date of Patent: Jul. 16, 2024

(54) DEVICES AND METHODS FOR TREATING A PATIENT'S SPINE

(71) Applicant: VertiFlex, Inc., Carlsbad, CA (US)

(72) Inventors: Moti Altarac, Irvine, CA (US); Robert Gutierrez, Mission Viejo, CA (US); Shawn Tebbe, Leixlip (IE); Daniel H. Kim, Houston, TX (US); J. Christopher Flaherty, Auburndale, FL (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 671 days.

(21) Appl. No.: 17/354,341

(22) Filed: Jun. 22, 2021

(65) Prior Publication Data

US 2021/0322063 A1    Oct. 21, 2021

Related U.S. Application Data

(63) Continuation of application No. 16/116,735, filed on Aug. 29, 2018, now Pat. No. 11,076,893, which is a
(Continued)

(51) Int. Cl.
*A61B 17/70* (2006.01)
*A61B 17/00* (2006.01)
(Continued)

(52) U.S. Cl.
CPC ...... *A61B 17/7065* (2013.01); *A61B 17/0206* (2013.01); *A61B 17/025* (2013.01);
(Continued)

(58) Field of Classification Search
CPC . A61B 17/70; A61B 17/7062; A61B 17/7064; A61B 17/7065; A61B 17/7067
See application file for complete search history.

(56) References Cited

U.S. PATENT DOCUMENTS 2,248,054 A   7/1941   Becker
2,677,369 A   5/1954   Knowles
(Continued)

FOREIGN PATENT DOCUMENTS

CA    268461 A     2/1927
CN    2794456 Y    7/2006
(Continued)

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
(Continued)

*Primary Examiner* — Christopher D. Prone
(74) *Attorney, Agent, or Firm* — Branch Partners PLLC; Bruce E. Black

(57) ABSTRACT

A plurality of individual tools is provided where each tool is uniquely configured to perform a step or a portion of a step in a novel procedure associated with the implantation of a stabilizing device (e.g., an interspinous spacer) for stabilizing at least one spinal motion segment. The tools are usable individually, or more preferably as a tooling system in which the tools are collectively employed to implant an interspinous spacer, generally in a minimally invasive manner. For example, each of the tools is arranged with coordinated markings and/or other features to ensure consistent depths of insertion, proper orientation of the tools with respect to each other or an anatomical feature of the patient, and precise delivery of the spacer to maintain safe positioning throughout the implantation procedure.

20 Claims, 49 Drawing Sheets

Related U.S. Application Data continuation of application No. 14/879,901, filed on Oct. 9, 2015, now Pat. No. 10,080,587, which is a continuation of application No. 13/413,550, filed on Mar. 6, 2012, now Pat. No. 9,155,572, which is a continuation of application No. 11/582,874, filed on Oct. 18, 2006, now Pat. No. 8,128,662.

(51) Int. Cl.

| | | |
|---|---|---|
| A61B 17/02 | (2006.01) | |
| A61B 17/16 | (2006.01) | |
| A61B 17/17 | (2006.01) | |
| A61B 17/34 | (2006.01) | |
| A61B 17/88 | (2006.01) | |
| A61B 17/84 | (2006.01) | |
| A61B 90/00 | (2016.01) | |
| A61F 2/00 | (2006.01) | |

(52) U.S. Cl.
CPC ...... *A61B 17/1671* (2013.01); *A61B 17/1697* (2013.01); *A61B 17/1757* (2013.01); *A61B 17/3421* (2013.01); *A61B 17/7067* (2013.01); *A61B 17/8866* (2013.01); *A61B 2017/00004* (2013.01); *A61B 2017/0023* (2013.01); *A61B 2017/00261* (2013.01); *A61B 2017/00557* (2013.01); *A61B 2017/0256* (2013.01); *A61B 17/7062* (2013.01); *A61B 17/848* (2013.01); *A61B 17/8897* (2013.01); *A61B 2090/033* (2016.02); *A61B 2090/034* (2016.02); *A61B 2090/062* (2016.02); *A61F 2/0077* (2013.01)

(56) References Cited

U.S. PATENT DOCUMENTS

| | | |
|---|---|---|
| 2,933,114 A | 4/1960 | Bystrom |
| 3,242,120 A | 3/1966 | Steuber |
| 3,486,505 A | 12/1969 | Morrison |
| 3,648,691 A | 3/1972 | Lumb et al. |
| 3,780,733 A | 12/1973 | Martinez |
| 3,986,383 A | 10/1976 | Petteys |
| 4,545,374 A | 10/1985 | Jacobson |
| 4,632,101 A | 12/1986 | Freeland |
| 4,685,447 A | 8/1987 | Iversen et al. |
| 4,799,484 A | 1/1989 | Smith et al. |
| 4,863,476 A | 9/1989 | Sheppard |
| 4,895,564 A | 1/1990 | Farrell |
| 4,986,831 A | 1/1991 | King |
| 5,011,484 A | 4/1991 | Breard et al. |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere et al. |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,335 A | 8/1997 | Allen |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin et al. |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,763 B1 | 7/2001 | Castro |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |

(56) References Cited

U.S. PATENT DOCUMENTS

| | | |
|---|---|---|
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps |
| 6,610,065 B1 | 8/2003 | Branch et al. |
| 6,610,091 B1 | 8/2003 | Reiley |
| 6,616,673 B1 | 9/2003 | Stone et al. |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | Dicarlo |
| 6,712,819 B2 | 3/2004 | Zucherman et al. |
| 6,716,215 B1 | 4/2004 | David et al. |
| 6,716,245 B2 | 4/2004 | Pasquel et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Amin et al. |
| 6,974,478 B2 | 12/2005 | Reiley et al. |
| 6,976,988 B2 | 12/2005 | Ralph et al. |
| 7,011,685 B2 | 3/2006 | Amin |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquel et al. |
| 7,097,648 B1 | 8/2006 | Globerman |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,187,064 B2 | 6/2007 | Matge et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell et al. |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Amin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu |
| 7,727,233 B2 | 6/2010 | Blackwell et al. |
| 7,727,241 B2 | 6/2010 | Gorensek et al. |
| 7,731,751 B2 | 6/2010 | Butler |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Amin |
| 7,763,028 B2 | 7/2010 | Lim |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Amin et al. |
| 7,811,322 B2 | 10/2010 | Amin et al. |
| 7,811,323 B2 | 10/2010 | Amin et al. |
| 7,811,324 B2 | 10/2010 | Amin et al. |
| 7,811,330 B2 | 10/2010 | Amin et al. |
| 7,819,921 B2 | 10/2010 | Grotz |

(56) References Cited

U.S. PATENT DOCUMENTS

| | | |
|---|---|---|
| 7,828,822 B2 | 11/2010 | Zucherman et al. |
| 7,828,849 B2 | 11/2010 | Lim |
| 7,833,272 B2 | 11/2010 | Amin et al. |
| 7,837,687 B2 | 11/2010 | Harp |
| 7,837,688 B2 | 11/2010 | Boyer et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Salsberg |
| 7,942,830 B2 | 5/2011 | Salsberg |
| 7,955,392 B2 | 6/2011 | Dewey et al. |
| 7,985,246 B2 | 7/2011 | Trieu et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Salsberg |
| 8,613,747 B2 | 12/2013 | Altarac et al. |
| 8,628,574 B2 | 1/2014 | Altarac et al. |
| 8,696,671 B2 | 4/2014 | Salsberg |
| 8,734,477 B2 | 5/2014 | Salsberg |
| 8,740,948 B2 | 6/2014 | Reglas |
| 8,845,726 B2 | 9/2014 | Tebbe et al. |
| 8,864,828 B2 | 10/2014 | Altarac et al. |
| 8,882,772 B2 | 11/2014 | Salsberg |
| 8,894,653 B2 | 11/2014 | Salsberg |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglas |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 | 9/2016 | Altarac et al. |
| 9,532,812 B2 | 1/2017 | Altarac et al. |
| 9,572,603 B2 | 2/2017 | Altarac et al. |
| 9,675,303 B2 | 6/2017 | Choi |
| 9,861,398 B2 | 1/2018 | Altarac et al. |
| 9,956,011 B2 | 5/2018 | Altarac et al. |
| 10,058,358 B2 | 8/2018 | Altarac et al. |
| 10,080,587 B2 | 9/2018 | Altarac et al. |
| 2001/0031965 A1 | 10/2001 | Zucherman et al. |
| 2002/0022856 A1 | 2/2002 | Johnson |
| 2002/0042607 A1 | 4/2002 | Palmer |
| 2002/0116009 A1 | 8/2002 | Fraser |
| 2002/0143331 A1 | 10/2002 | Zucherman et al. |
| 2002/0151977 A1 | 10/2002 | Paes et al. |
| 2003/0040746 A1 | 2/2003 | Mitchell et al. |
| 2003/0040753 A1 | 2/2003 | Daum |
| 2003/0074075 A1 | 4/2003 | Thomas et al. |
| 2003/0105466 A1 | 6/2003 | Ralph et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0148028 A1 | 7/2004 | Ferree |
| 2004/0167625 A1 | 8/2004 | Beyar et al. |
| 2004/0220568 A1 | 11/2004 | Zucherman et al. |
| 2004/0225295 A1 | 11/2004 | Zubok et al. |
| 2005/0021042 A1 | 1/2005 | Marnay |
| 2005/0049708 A1 | 3/2005 | Atkinson et al. |
| 2005/0075634 A1 | 4/2005 | Zucherman et al. |
| 2005/0090822 A1 | 4/2005 | DiPoto et al. |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0209698 A1 | 9/2005 | Gordon |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278036 A1 | 12/2005 | Leonard et al. |
| 2006/0030860 A1 | 2/2006 | Peterman |
| 2006/0036258 A1 | 2/2006 | Zucherman et al. |
| 2006/0064107 A1 | 3/2006 | Bertagnoli et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0122458 A1 | 6/2006 | Bleich |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |

(56) References Cited

U.S. PATENT DOCUMENTS

| | | |
|---|---|---|
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191857 A1 | 8/2007 | Allard et al. |
| 2007/0191948 A1 | 8/2007 | Amin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquel et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Salsberg |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0086212 A1 | 4/2008 | Zucherman et al. |
| 2008/0108990 A1 | 5/2008 | Mitchell |
| 2008/0114455 A1 | 5/2008 | Lange et al. |
| 2008/0132952 A1 | 6/2008 | Malandain |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling |
| 2010/0160947 A1 | 6/2010 | Akyuz et al. |
| 2010/0228092 A1 | 9/2010 | Ortiz |
| 2010/0234889 A1 | 9/2010 | Hess |

(56) References Cited

U.S. PATENT DOCUMENTS

| | | |
|---|---|---|
| 2010/0262243 A1 | 10/2010 | Zucherman et al. |
| 2010/0280551 A1 | 11/2010 | Pool |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Lopez |
| 2012/0303039 A1 | 11/2012 | Chin et al. |
| 2012/0330359 A1 | 12/2012 | Kim et al. |
| 2013/0012998 A1 | 1/2013 | Altarac et al. |
| 2013/0072985 A1 | 3/2013 | Kim et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi |
| 2013/0289622 A1 | 10/2013 | Kim |
| 2014/0081332 A1 | 3/2014 | Altarac et al. |
| 2014/0214082 A1 | 7/2014 | Reglos |
| 2015/0150598 A1 | 6/2015 | Tebbe et al. |
| 2015/0150604 A1 | 6/2015 | Kim |
| 2015/0374415 A1 | 12/2015 | Kim |
| 2016/0030092 A1 | 2/2016 | Altarac et al. |
| 2016/0066963 A1 | 3/2016 | Kim |
| 2016/0317193 A1 | 11/2016 | Kim et al. |
| 2017/0071588 A1 | 3/2017 | Choi |
| 2017/0128110 A1 | 5/2017 | Altarac et al. |
| 2017/0245883 A1 | 8/2017 | Tebbe et al. |
| 2017/0258501 A1 | 9/2017 | Altarac et al. |
| 2017/0273722 A1 | 9/2017 | Altarac et al. |
| 2018/0028130 A1 | 2/2018 | Choi |
| 2018/0193064 A1 | 7/2018 | Kim |
| 2018/0228519 A1 | 8/2018 | Altarac et al. |
| 2019/0069933 A1 | 3/2019 | Altarac et al. |
| 2019/0090912 A1 | 3/2019 | Altarac et al. |
| 2019/0105082 A1 | 4/2019 | Altarac et al. |
| 2019/0105083 A1 | 4/2019 | Kim |
| 2019/0201057 A1 | 7/2019 | Altarac et al. |

FOREIGN PATENT DOCUMENTS

| | | |
|---|---|---|
| CN | 101897603 A | 12/2010 |
| DE | 69507480 T2 | 9/1999 |
| EP | 322334 A1 | 6/1989 |
| EP | 0767636 A1 | 4/1997 |
| EP | 0768843 B1 | 2/1999 |
| EP | 1027004 A1 | 8/2000 |
| EP | 1030615 A1 | 8/2000 |
| EP | 1138268 A1 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 0959792 B1 | 11/2007 |
| EP | 1861046 A2 | 12/2007 |
| FR | 2681525 A1 | 3/1993 |
| FR | 2717675 A1 | 3/1994 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO07131165 A2 | 11/1970 |
| WO | WO9404088 A1 | 3/1994 |
| WO | WO9426192 A1 | 11/1994 |
| WO | WO9525485 A1 | 9/1995 |
| WO | WO9531158 A1 | 11/1995 |
| WO | WO9600049 A1 | 1/1996 |
| WO | WO9829047 A1 | 7/1998 |
| WO | WO9921500 A1 | 5/1999 |
| WO | WO9921501 A1 | 5/1999 |
| WO | WO9942051 A1 | 8/1999 |
| WO | WO0013619 A1 | 3/2000 |
| WO | WO0044319 A1 | 8/2000 |
| WO | WO0044321 A2 | 8/2000 |
| WO | WO0128442 A1 | 4/2001 |
| WO | WO0191657 A1 | 12/2001 |
| WO | WO0191658 A1 | 12/2001 |
| WO | WO0203882 A2 | 1/2002 |
| WO | WO0207623 A1 | 1/2002 |
| WO | WO0207624 A1 | 1/2002 |
| WO | WO02051326 A1 | 7/2002 |
| WO | WO02067793 A2 | 9/2002 |
| WO | WO02071960 A1 | 9/2002 |
| WO | WO02076336 A2 | 10/2002 |
| WO | WO03007791 A2 | 1/2003 |
| WO | WO03007829 A1 | 1/2003 |
| WO | WO03008016 A2 | 1/2003 |
| WO | WO03015646 A2 | 2/2003 |
| WO | WO03024298 A2 | 3/2003 |
| WO | WO03045262 A2 | 6/2003 |
| WO | WO03099147 A1 | 12/2003 |
| WO | WO03101350 A1 | 12/2003 |
| WO | WO04073533 A1 | 9/2004 |
| WO | WO04110300 A2 | 12/2004 |
| WO | WO05009300 A1 | 2/2005 |
| WO | WO05013839 A2 | 2/2005 |
| WO | WO05025461 A2 | 3/2005 |
| WO | WO05041799 A1 | 5/2005 |
| WO | WO05044152 A1 | 5/2005 |
| WO | WO05055868 A2 | 6/2005 |
| WO | WO05079672 A2 | 9/2005 |
| WO | WO2005086776 A2 | 9/2005 |
| WO | WO05115261 A1 | 12/2005 |
| WO | WO06033659 A2 | 3/2006 |
| WO | WO06034423 A2 | 3/2006 |
| WO | WO06039243 A1 | 4/2006 |
| WO | WO06039260 A2 | 4/2006 |
| WO | WO06045094 A2 | 4/2006 |
| WO | WO2006045094 A2 | 4/2006 |
| WO | WO06063047 A2 | 6/2006 |
| WO | WO06065774 A1 | 6/2006 |
| WO | WO2006063047 A2 | 6/2006 |
| WO | WO2006064356 A1 | 6/2006 |
| WO | WO2006089085 A2 | 8/2006 |
| WO | WO06102269 A1 | 9/2006 |
| WO | WO06102428 A1 | 9/2006 |
| WO | WO06102485 A2 | 9/2006 |
| WO | WO06107539 A1 | 10/2006 |
| WO | WO06110462 A2 | 10/2006 |
| WO | WO06110464 A2 | 10/2006 |
| WO | WO06110767 A1 | 10/2006 |
| WO | WO06113080 A2 | 10/2006 |
| WO | WO06113406 A2 | 10/2006 |
| WO | WO06113814 A2 | 10/2006 |
| WO | WO06118945 A1 | 11/2006 |
| WO | WO06119235 A1 | 11/2006 |
| WO | WO06119236 A2 | 11/2006 |
| WO | WO06135511 A1 | 12/2006 |
| WO | WO07015028 A1 | 2/2007 |
| WO | WO07035120 A1 | 3/2007 |
| WO | WO07075375 A2 | 7/2007 |
| WO | WO07075788 A2 | 7/2007 |
| WO | WO07075791 A2 | 7/2007 |
| WO | WO07089605 A2 | 8/2007 |
| WO | WO07089905 A2 | 8/2007 |
| WO | WO07089975 A1 | 8/2007 |
| WO | WO07097735 A2 | 8/2007 |
| WO | WO07109402 A2 | 9/2007 |
| WO | WO07110604 A1 | 10/2007 |
| WO | WO07111795 A1 | 10/2007 |
| WO | WO07111979 A2 | 10/2007 |
| WO | WO07111999 A2 | 10/2007 |
| WO | WO07117882 A1 | 10/2007 |
| WO | WO07121070 A2 | 10/2007 |
| WO | WO07127550 A2 | 11/2007 |
| WO | WO07127588 A1 | 11/2007 |

(56) References Cited

FOREIGN PATENT DOCUMENTS

| | | |
|---|---|---|
| WO | WO07127677 A1 | 11/2007 |
| WO | WO07127689 A2 | 11/2007 |
| WO | WO07127694 A2 | 11/2007 |
| WO | WO07127734 A2 | 11/2007 |
| WO | WO07127736 A2 | 11/2007 |
| WO | WO07134113 A2 | 11/2007 |
| WO | WO2008009049 A1 | 1/2008 |
| WO | WO08048645 A2 | 4/2008 |
| WO | WO2008057506 A2 | 5/2008 |
| WO | WO20081 30564 A1 | 10/2008 |
| WO | WO2009014728 A2 | 1/2009 |
| WO | WO2009033093 A1 | 3/2009 |
| WO | WO2009086010 A2 | 7/2009 |
| WO | WO2009091922 A2 | 7/2009 |
| WO | WO2009094463 A2 | 7/2009 |
| WO | WO2009114479 A2 | 9/2009 |
| WO | WO20110844 77 A2 | 7/2011 |
| WO | WO2015171814 A1 | 11/2015 |

OTHER PUBLICATIONS

Australia Exam Report for Application No. AU2006329867, Applicant: The Board of Trustees of Leland Stanford Junior University; Date of Issue: Jan. 27, 2012, 2 pages.
Australia Exam Report for Application No. AU2007317886, Applicant: VertiFlex, Inc.; Date of Issue: Jun. 18, 2012, 3 pages.
Australia Exam Report for Application No. AU2008241447, Applicant: VertiFlex, Inc.; Date of Issue: Jul. 5, 2012, 4 pages.
Australia Exam Report for Application No. AU2008275708, Applicant: VertiFlex, Inc.; Date of Issue: Nov. 12, 2012, 4 pages.
Australia Exam Report for Application No. AU2008279680, Applicant: VertiFlex, Inc.; Date of Issue: Oct. 30, 2012, 5 pages.
Australia Exam Report for Application No. AU2008296066, Applicant: VertiFlex, Inc.; Date of Issue: Mar. 6, 2013, 3 pages.
Australia Exam Report for Application No. AU2008343092, Applicant: VertiFlex, Inc.; Date of Issue: Feb. 8, 2013, 4 pages.
Australia Exam Report for Application No. AU2013273815, Applicant: The Board of Trustees of Leland Stanford Junior University; Date of Issue: Apr. 17, 2015, 3 pages.
Australia Exam Report for Application No. AU2014203394, Applicant: VertiFlex, Inc., Date of Issue: Mar. 15, 2016, 2 pages.
Australia Exam Report No. 1 for Application No. AU2009206098, Applicant: VertiFlex, Inc.; Date of Issue: Mar. 6, 2013, 4 pages.
Australia Exam Report No. 2 for Application No. AU2009206098, Applicant: VertiFlex, Inc.; Date of Issue: Aug. 19, 2014, 4 pages.
Canada Exam Report for Application No. CA2634251, Applicant: The Board of Trustees of Leland Stanford Junior University; Date of Issue: Dec. 3, 2013, 2 pages.
Canada Exam Report for Application No. CA2668833, Applicant: Vertiflex, Inc.; Date of Issue: Dec. 5, 2013, 2 pages.
Canada Exam Report for Application No. CA2695937, Applicant: Vertiflex, Inc.; Date of Issue: Aug. 7, 2014, 2 pages.
Canada Exam Report for Application No. CA2697628, Applicant: Vertiflex, Inc.; Date of Issue: Oct. 16, 2014, 2 pages.
Canada Exam Report for Application No. CA2698718, Applicant: Vertiflex, Inc.; Date of Issue: May 20, 2014, 3 pages.
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
European Further Exam Report for Application No. EP09702116.6; Applicant: VertiFlex, Inc.; Date of Mailing: Jul. 4, 2016, 4 pages.
European Examination Report for Application No. 08794704.0; Applicant: Vertiflex, Inc.; Date of Mailing Apr. 5, 2017, 6 pages.
European Examination Report for Application No. 08799267.3; Applicant: Vertiflex, Inc.: Date of Mailing Sep. 5, 2017, 4 pages.
Fast, Avital et al., "Surgical Treatment of Lumbar Spinal Stenosis in the Elderly," Arch Phys. Med Rehabil., Mar. 1985, pp. 149-151, vol. 66.
First Examination Report in European Patent Application No. 08780034.8, mail date Jan. 16, 2017, 5 pages.
Further Examination Report in European Patent Application No. 07861426.0, mail date Oct. 4, 2017, 4 pages.
Further Examination Report in European Patent Application No. 08867282.9, mail date Oct. 15, 2018, 7 pages.
International Search Report and Written Opinion; Application No. PCT/US2006/047824; Mailing Date: Oct. 16, 2008, 17 pages.
International Search Report and Written Opinion; Application No. PCT/US2006/048611; Mailing Date: Oct. 14, 2008; 10 pages.
International Search Report and Written Opinion; Application No. PCT/US2006/048614; Mailing Date: Feb. 3, 2006; 23 pages.
International Search Report and Written Opinion; Application No. PCT/US2007/022171; Mailing Date: Apr. 15, 2008, 9 pages.
International Search Report and Written Opinion; Application No. PCT/US2007/023312; Mailing Date: May 22, 2008, 14 pages.
International Search Report and Written Opinion; Application No. PCT/US2008/004901; Mailing Date: Aug. 19, 2008, 7 pages.
International Search Report and Written Opinion; Application No. PCT/US2008/008382; Mailing Date: Mar. 2, 2009, 13 pages.
International Search Report and Written Opinion; Application No. PCT/US2008/008983; Mailing Date: Feb. 23, 2009, 7 pages.
International Search Report and Written Opinion; Application No. PCT/US2008/075487; Mailing Date: Dec. 31, 2008, 7 pages.
International Search Report and Written Opinion; Application No. PCT/US2008/087527; Mailing Date: Jul. 30, 2009, 10 pages.
International Search Report and Written Opinion; Application No. PCT/US2009/031150; Mailing Date: Aug. 28, 2009, 6 pages.
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
McCulloch, John A., Young, Paul H., "Essentials of Spinal Microsurgery," 1998, pp. 453-485. Lippincott-Raven Publishers, Philadelphia, PA (37 pages total).
Minns, R.J., et al., "Preliminary Design and Experimental Studies of a Noval Soft Implant for Correcting Sagittal Plane Instability in the Lumbar Spine," (1997) Spine, 22(16): 1819-1827.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
Supplementary European Search Report for Application No. EP06845480; Applicant: VertiFlex, Inc.; Date of Completion: Aug. 14, 2012, 9 pages.
Supplementary European Search Report for Application No. EP07861426; Applicant: VertiFlex, Inc.; Date of Issue: Jun. 7, 2011, 6 pages.
Supplementary European Search Report for Application No. EP07861721.4; Applicant: VertiFlex, Inc.; Date of Issue: Nov. 24, 2009, 6 pages.
Supplementary European Search Report for Application No. EP08742949.4; Applicant: VertiFlex, Inc.; Date of Issue: Jul. 19, 2012, 4 pages.
Supplementary European Search Report for Application No. EP08780034.8; Applicant: VertiFlex, Inc.; Date of Issue: Sep. 19, 2012, 7 pages.
Supplementary European Search Report for Application No. EP08794704.0; Applicant: VertiFlex, Inc.; Date of Issue: Oct. 23, 2012, 9 pages.
Supplementary European Search Report for Application No. EP08799267.3; Applicant: VertiFlex, Inc.; Date of Issue: Jun. 29, 2011, 7 pages.
Supplementary European Search Report for Application No. EP08867282.9; Applicant: VertiFlex, Inc.; Date of Issue: Nov. 28, 2012, 10 pages.
Supplementary European Search Report for Application No. EP09170304.1; Applicant: VertiFlex, Inc.; Date of Issue: Nov. 24, 2009, 5 pages.

(56) References Cited

OTHER PUBLICATIONS

Supplementary European Search Report for Application No. EP09170338.9; Applicant: VertiFlex, Inc.; Date of Issue: Nov. 24, 2009, 6 pages.
Supplementary European Search Report for Application No. EP09702116.6; Applicant: VertiFlex, Inc.; Date of Issue: Feb. 11, 2011, 7 pages.
Supplementary European Search Report for Application No. EP11151901.3; Applicant: VertiFlex, Inc.; Date of Issue: Apr. 7, 2011, 6 pages.
Supplementary European Search Report for Application No. EP13184922.6; Applicant: VertiFlex, Inc.; Date of Issue: Oct. 30, 2013, 8 pages.
Supplementary European Search Report; Application No. EP07861426.0; Applicant: Vertiflex, Inc.; Date of Completion: Jun. 7, 2011, 6 pages.
Supplementary European Search Report; Application No. EP07861721.4; Applicant: Vertiflex, Inc.; Date of Completion: Nov. 24, 2009, 6 pages.
Supplementary European Search Report; Application No. EP09170304.1; Applicant: Vertiflex, Inc.; Date of Completion: Nov. 11, 2009, 5 pages.
Supplementary European Search Report; Application No. EP09170338.9; Applicant: Vertiflex, Inc.; Date of Completion: Nov. 12, 2009, 6 pages.
Supplementary European Search Report; Application No. EP09702116.6; Applicant: Vertiflex, Inc.; Date of Completion: Feb. 11, 2011, 6 pages.
Supplementary European Search Report; Application No. EP11151901.3; Applicant: Vertiflex, Inc.; Date of Completion: Apr. 7, 2011, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.
Tredway, Trent L et al., "Minimally Invasive Transforaminal Lumbar Interbody Fusion (MI-TLIF) and Lateral Mass Fusion with the MetRx System," (14 pages total), 2005.
Vaccaro, Alexander J. et al., MasterCases Spine Surgery, 2001, pp. 100-107. Thieme Medical Publishers, Inc., NY. (10 pages total).
Vertos mild Devices Kit—PRT-00430-C—Instructions for Use (13 pages total); see http://vertosmed.com/docs/mild1FU_PRT-00430-C.pdf., 2012.

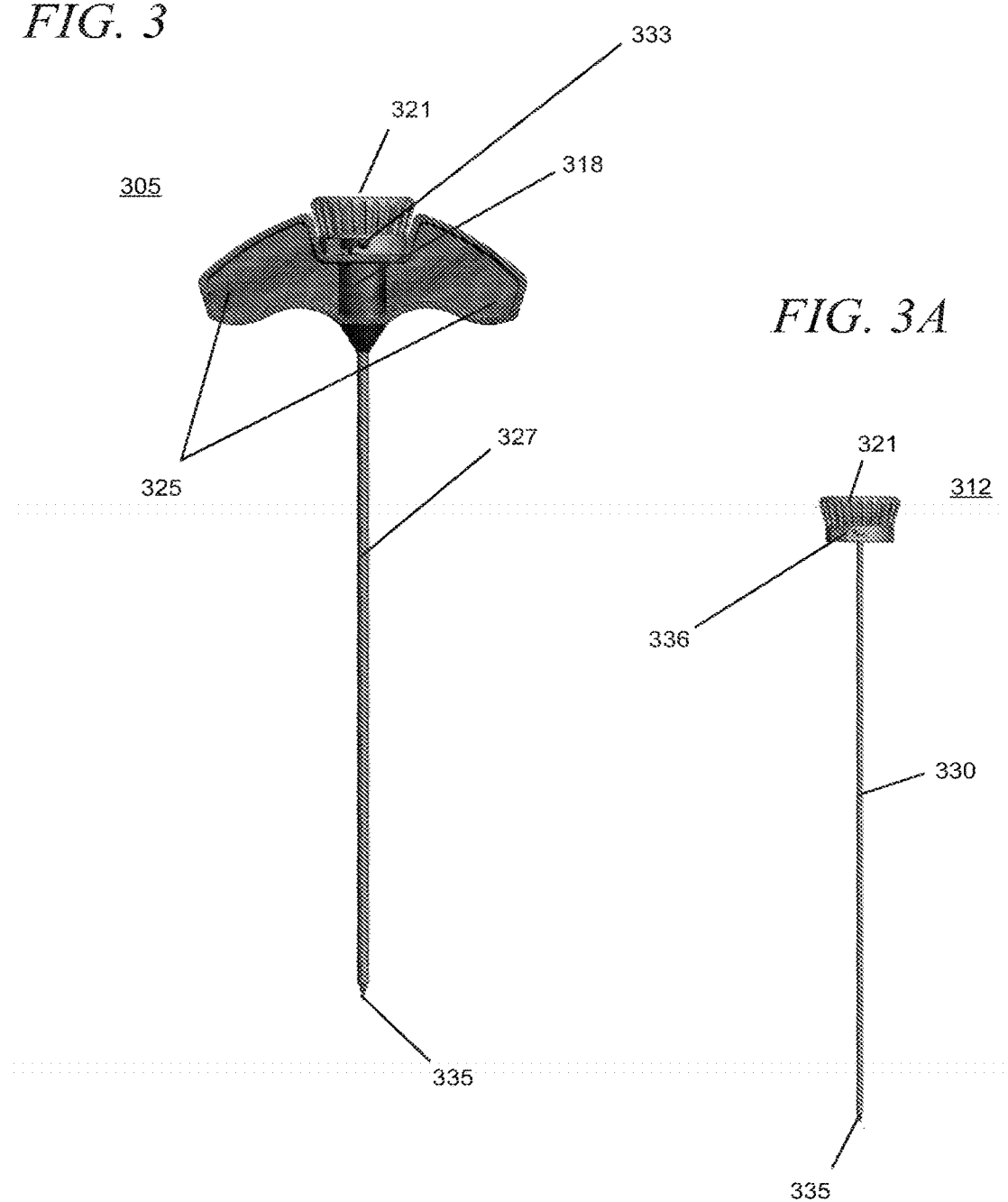

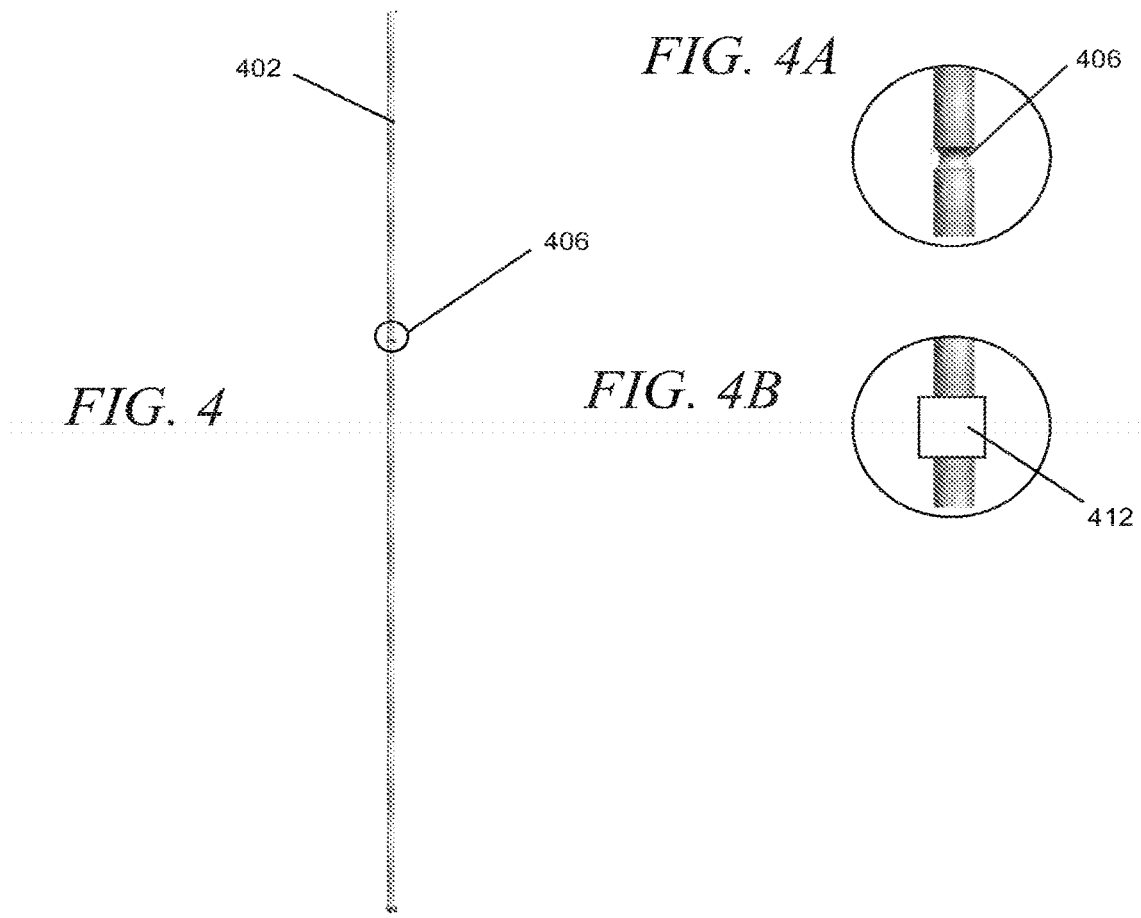
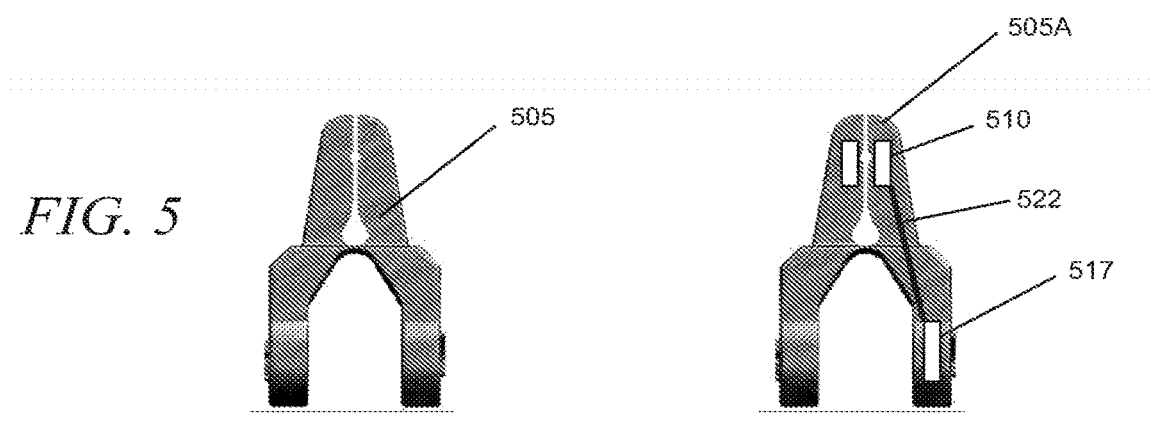

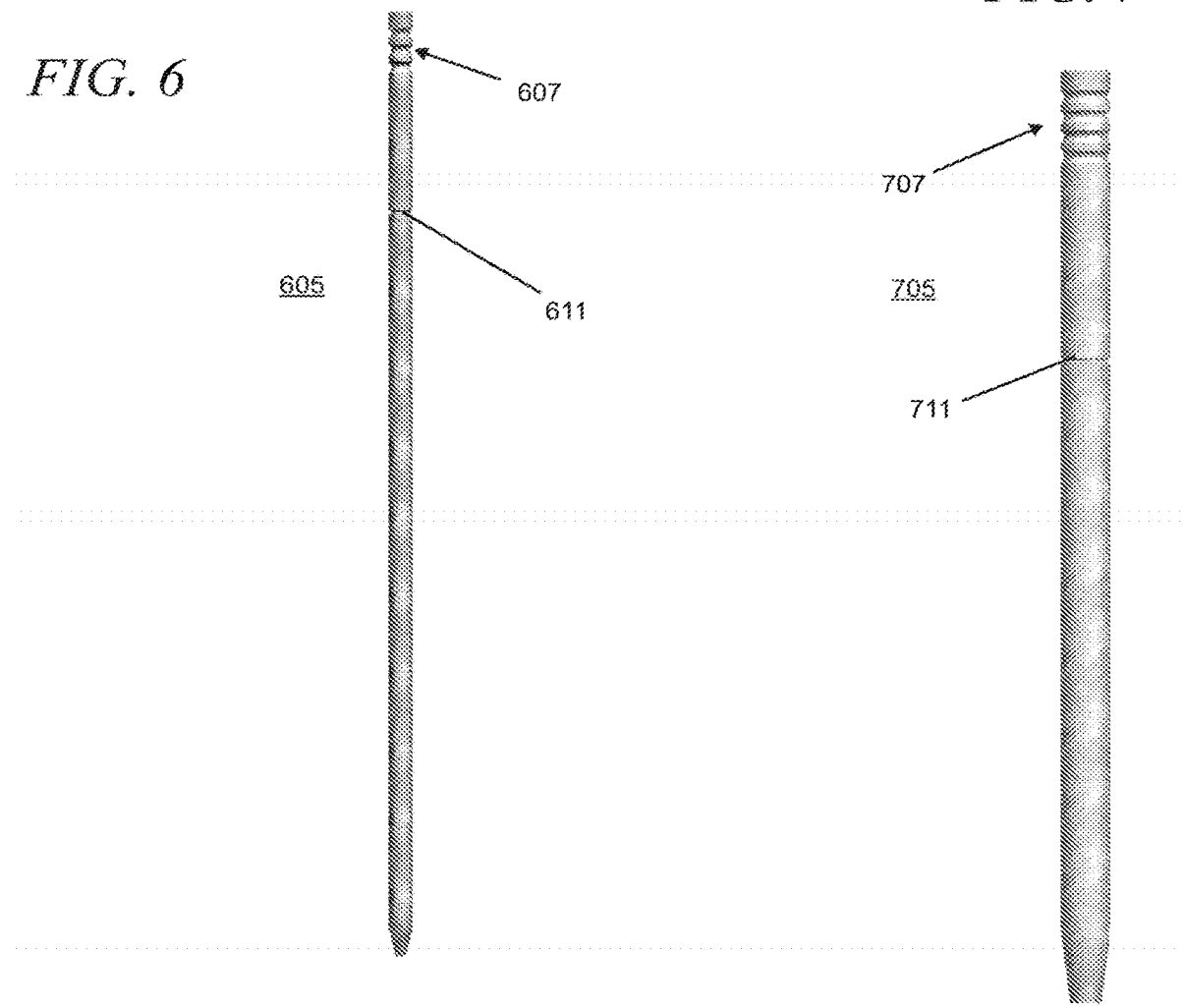
FIG. 6
FIG. 7
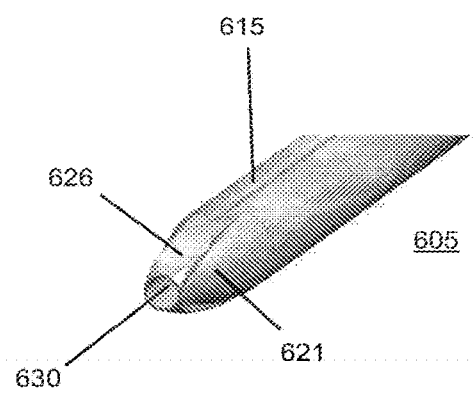
FIG. 6A
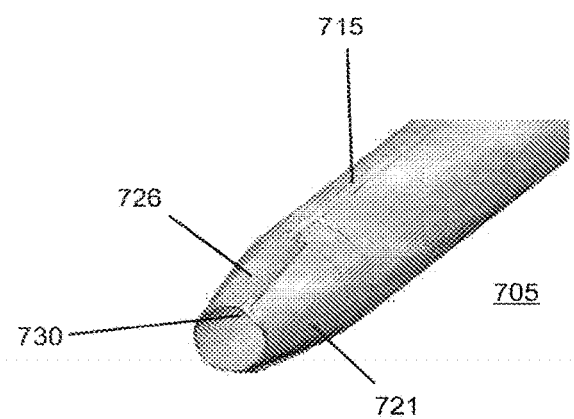
FIG. 7A

FIG. 11
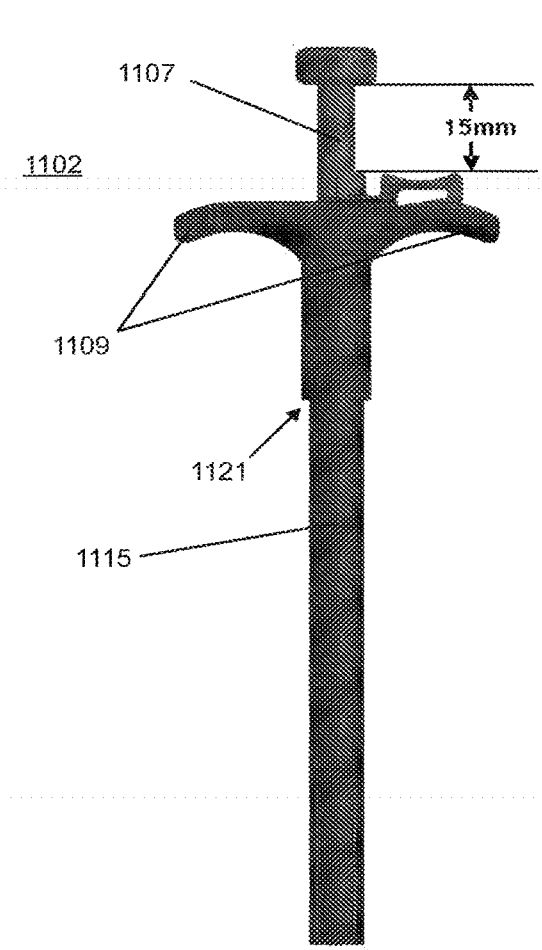
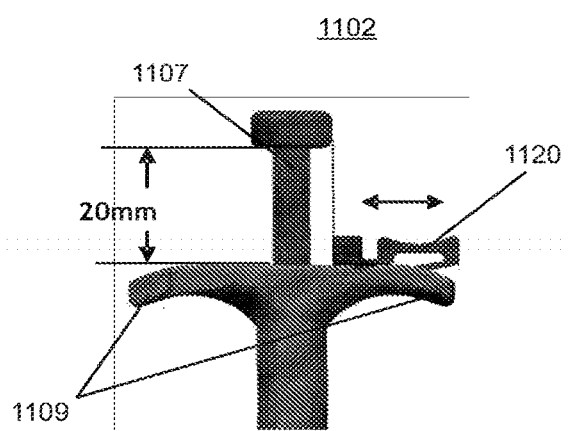
FIG. 11B
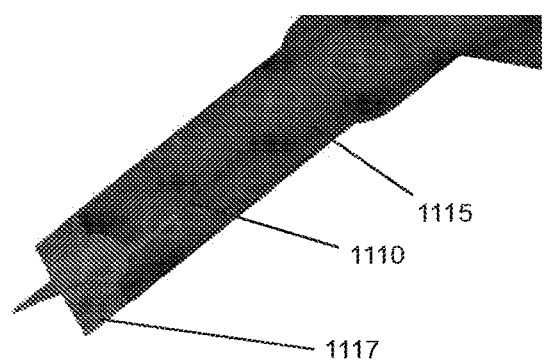
FIG. 11A

FIG. 14
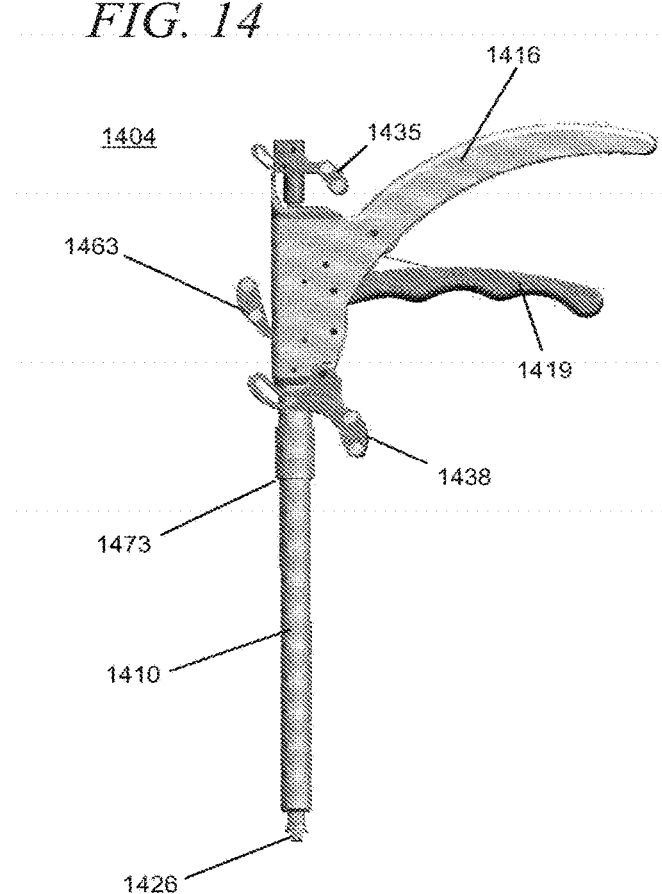
FIG. 14A
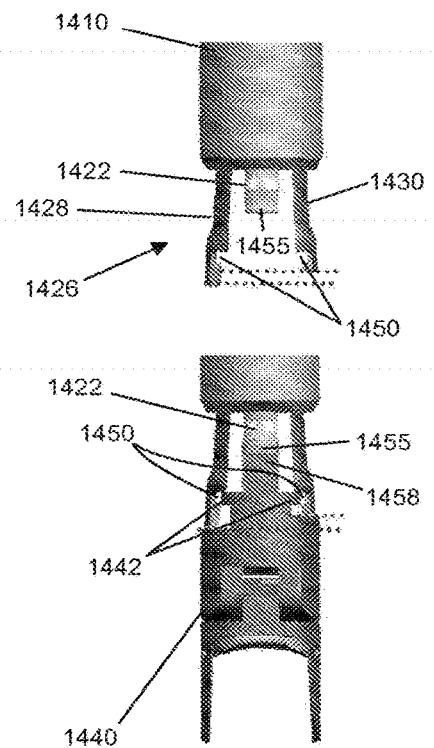
FIG. 14B
FIG. 14C
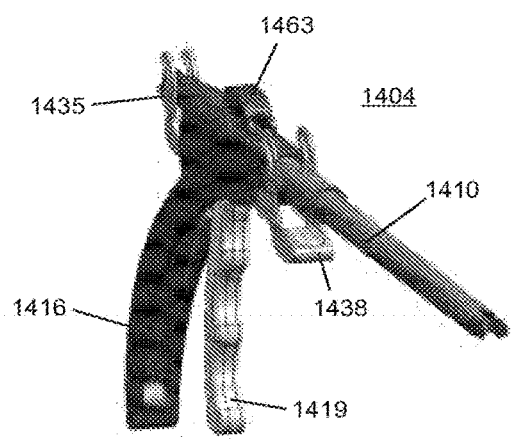
FIG. 14D
+2 = D+2mm
+1 = D+1mm
D = DEPLOYED
L = LOAD
FIG. 14E

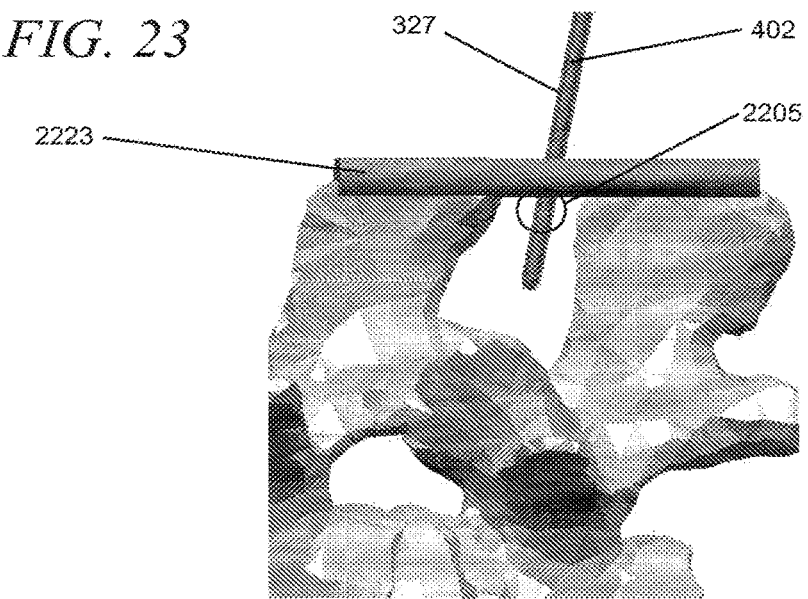
FIG. 23
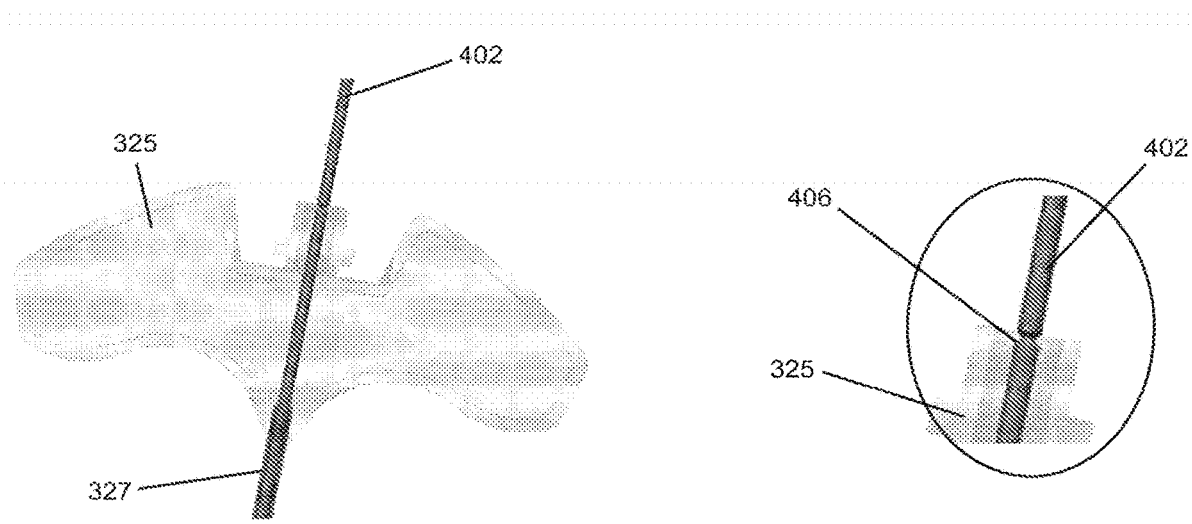
FIG. 23A
FIG. 23B

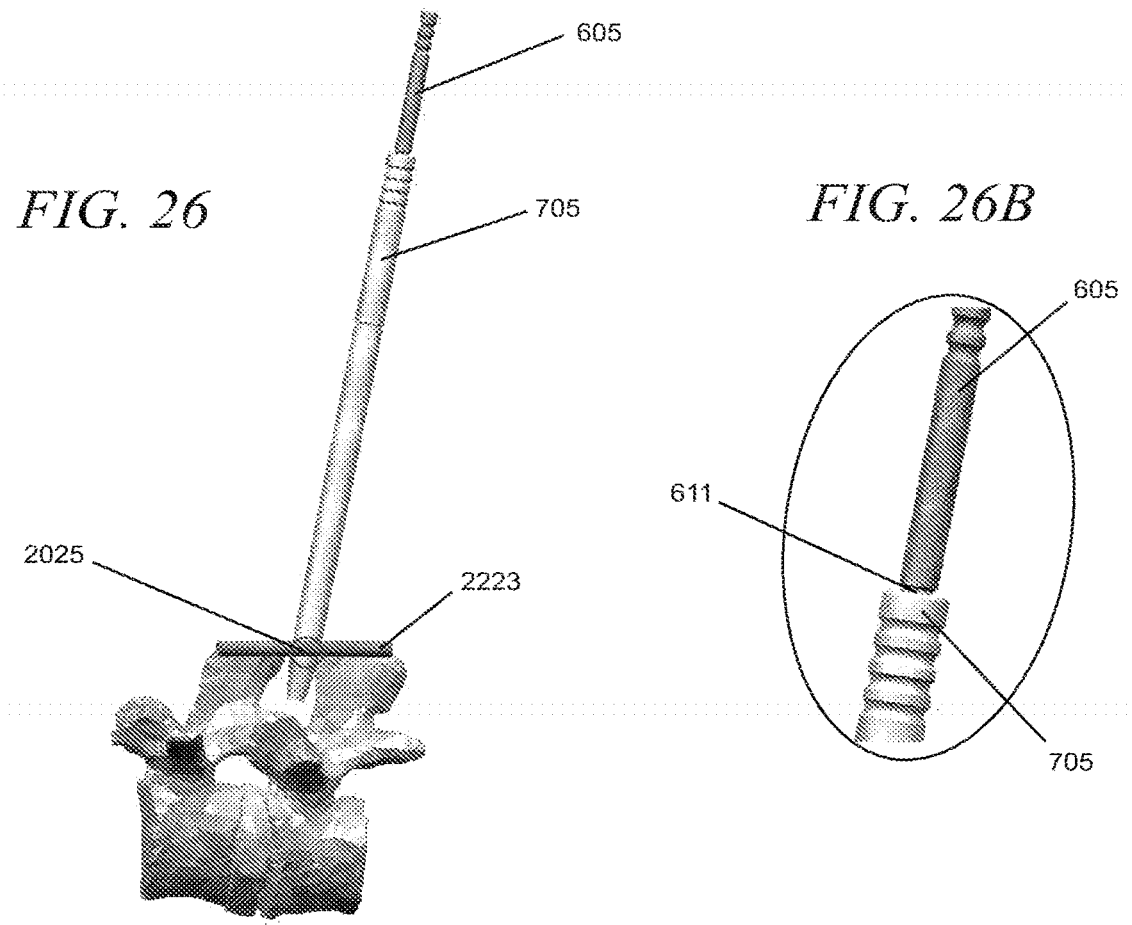
FIG. 26
FIG. 26B
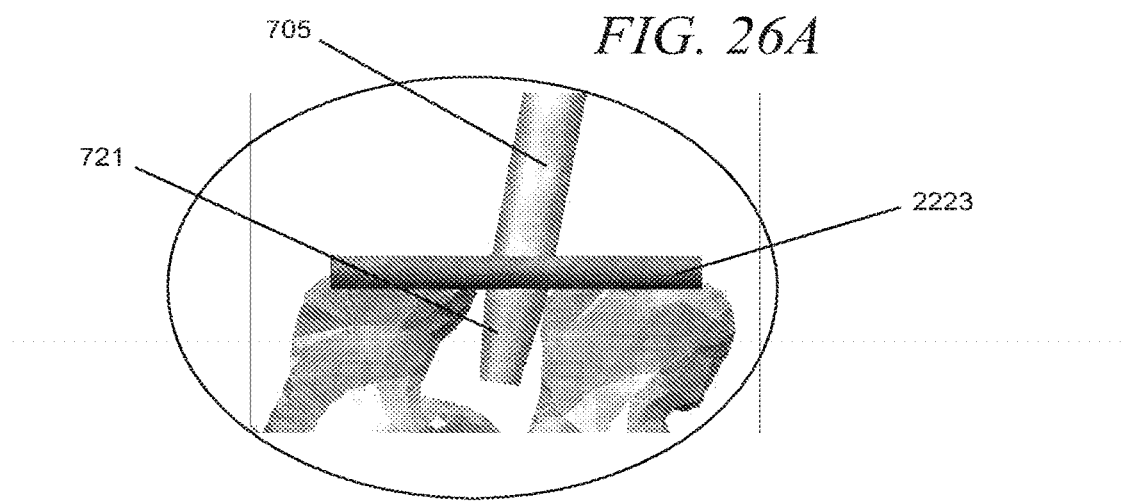
FIG. 26A

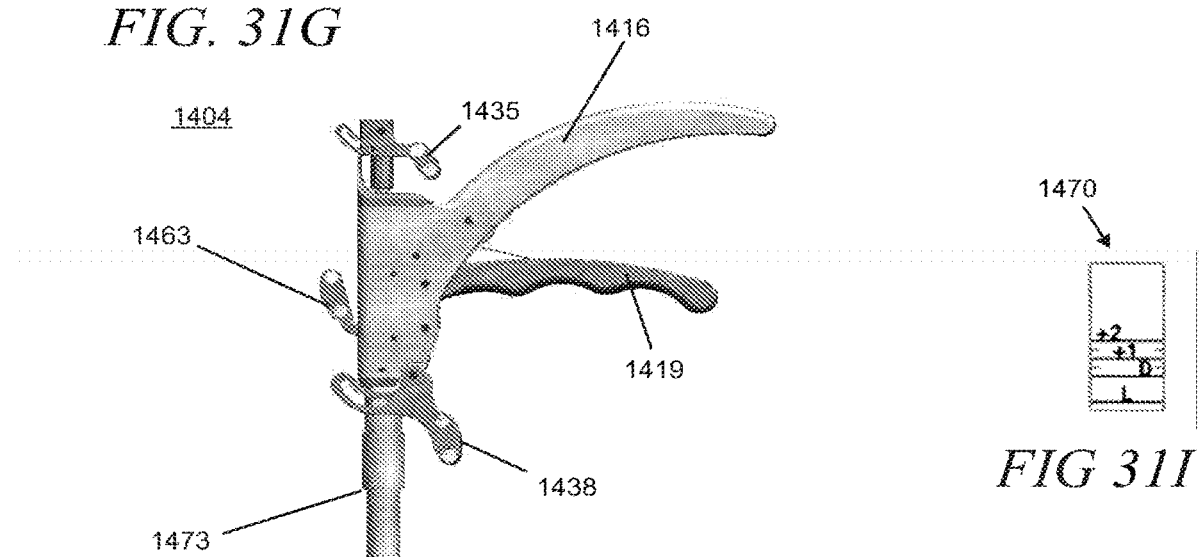
FIG. 31G
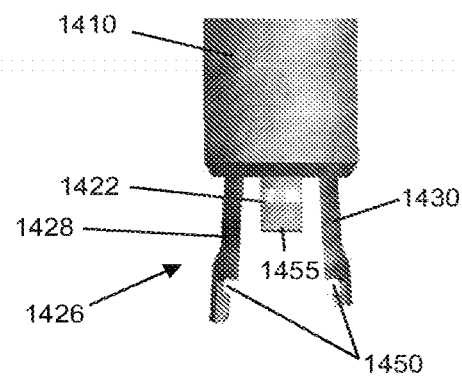
FIG. 31H
FIG. 31I
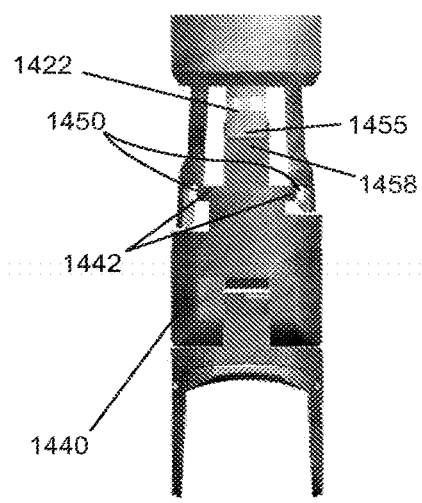
FIG. 31J
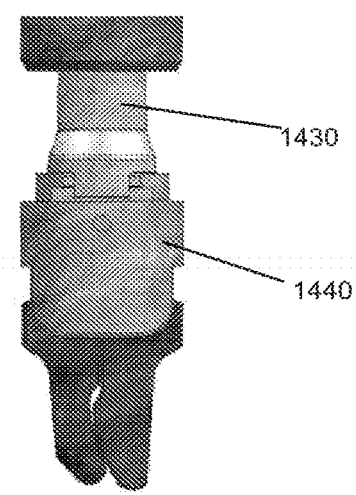
FIG. 31K

DEVICES AND METHODS FOR TREATING A PATIENT'S SPINE

CROSS-REFERENCE TO RELATED APPLICATIONS

This application is a continuation of U.S. patent application Ser. No. 16/116,735, now U.S. Pat. No. 11,076,893 entitled "METHODS FOR TREATING A PATIENT'S SPINE," filed on Aug. 29, 2018, which is a continuation of U.S. patent application Ser. No. 14/879,901, now U.S. Pat. No. 10,080,587, entitled "METHODS FOR TREATING A PATIENT'S SPINE," filed on Oct. 9, 2015, which is a continuation of Ser. No. 13/413,550, now U.S. Pat. No. 9,155,572, entitled "MINIMALLY INVASIVE TOOLING FOR DELIVERY OF INTERSPINOUS SPACER," filed on Mar. 6, 2012, which is a continuation of U.S. patent application Ser. No. 11/582,874, now U.S. Pat. No. 8,128,662, entitled "MINIMALLY INVASIVE TOOLING FOR DELIVERY OF INTERSPINOUS SPACER," filed on Oct. 18, 2006.

Other related patents and patent applications include U.S. patent application Ser. No. 11/314,712, now U.S. Pat. No. 8,152,837, entitled "SYSTEMS AND METHODS FOR POSTERIOR DYNAMIC STABILIZATION OF THE SPINE," filed on Dec. 20, 2005, which is a continuation-in-part of U.S. patent application Ser. No. 11/190,496, now U.S. Pat. No. 8,409,282, entitled "SYSTEMS AND METHODS FOR POSTERIOR DYNAMIC STABILIZATION OF THE SPINE," filed Jul. 26, 2005, which is a continuation-in-part of U.S. patent application Ser. No. 11/079,006, now U.S. Pat. No. 8,012,207, entitled "SYSTEMS AND METHODS FOR POSTERIOR DYNAMIC STABILIZATION OF THE SPINE," filed on Mar. 10, 2005, which is a continuation-in-part of U.S. patent application Ser. No. 11/052,002, now U.S. Pat. No. 8,317,864, entitled "SYSTEMS AND METHODS FOR POSTERIOR DYNAMIC STABILIZATION OF THE SPINE," filed Feb. 4, 2005, which is a continuation-in-part of U.S. patent application Ser. No. 11/006,502, now U.S. Pat. No. 8,123,807, entitled "SYSTEMS AND METHODS FOR POSTERIOR DYNAMIC STABILIZATION OF THE SPINE," filed on Dec. 6, 2004, which is a continuation-in-part of U.S. patent application Ser. No. 10/970,843, now U.S. Pat. No. 8,167,944, entitled "SYSTEMS AND METHODS FOR POSTERIOR DYNAMIC STABILIZATION OF THE SPINE," filed Oct. 20, 2004. All of the above-referenced applications and patents are hereby incorporated by reference in their entireties.

TECHNICAL FIELD

The present invention is related to treatment of spinal disorders and pain and, more particularly, to minimally invasive tooling for delivery of an interspinous spacer device.

BACKGROUND

FIGS. 1 and 2A illustrates a portion of the human spine having a superior vertebra 2 and an inferior vertebra 4, with an intervertebral disc 6 located in between the two vertebral bodies. The superior vertebra 2 has superior facet joints 8a and 8b, inferior facet joints 10a and 10b, and spinous process 18. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 10a and 10b and the spinous process 18 are laminal zones 5a and 5b, respectively. Similarly, inferior vertebra 4 has superior facet joints 12a and 12b, superior pedicles 9a and 9b, transverse processes 11a and 11b, inferior facet joints 14a and 14b, laminal zones 15a and 15b, and spinous process 22.

The superior vertebra with its inferior facets, the inferior vertebra with its superior facet joints, the intervertebral disc, and seven spinal ligaments (not shown) extending between the superior and inferior vertebrae together comprise a spinal motion segment or functional spine unit. Each spinal motion segment enables motion along three orthogonal axes, both in rotation and in translation. The various spinal motions are illustrated in FIGS. 2A-2C. In particular, FIG. 2A illustrates flexion and extension motions and axial loading, FIG. 2B illustrates lateral bending motion and FIG. 2C illustrates axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. It is one of the most common approaches to alleviating various types of spinal pain, particularly pain associated with one or more affected intervertebral discs. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments. Additionally, pseudarthrosis (resulting from an incomplete or ineffective fusion) may not provide the expected pain-relief for the patient. Also, the device(s) used for fusion, whether artificial or biological, may migrate out of the fusion site creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the mechanics of motion for the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or istlunic spondylotlisthesis, pinching the nerves that extend between the affected vertebrae.

Current interventions for the treatment of facet joint disorders have not been found to provide completely successful results. Facetectomy (removal of the facet joints)

may provide some pain relief; but as the facet joints help to support axial, torsional, and shear loads that act on the spinal column in addition to providing a sliding articulation and mechanism for load transmission, their removal inhibits natural spinal function. Laminectomy (removal of the lamina, including the spinal arch and the spinous process) may also provide pain relief associated with facet joint disorders; however, the spine is made less stable and subject to hypermobility. Problems with the facet joints can also complicate treatments associated with other portions of the spine. In fact, contraindications for disc replacement include arthritic facet joints, absent facet joints, severe facet joint tropism, or otherwise deformed facet joints due to the inability of the artificial disc (when used with compromised or missing facet joints) to properly restore the natural biomechanics of the spinal motion segment.

While various attempts have been made at facet joint replacement, they have been inadequate. This is due to the fact that prosthetic facet joints preserve existing bony structures and therefore do not address pathologies that affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facet joint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes) facet joint replacement is insufficient to treat the problem(s).

Most recently, surgical-based technologies, referred to as "dynamic posterior stabilization," have been developed to address spinal pain resulting from more than one disorder" when more than one structure of the spine have been compromised. An objective of such technologies is to provide the support of fusion-based implants while maximizing the natural biomechanics of the spine. Dynamic posterior stabilization systems typically fall into one of two general categories: posterior pedicle screw-based systems and interspinous spacers.

Examples of pedicle screw-based systems are disclosed in U.S. Pat. Nos. 5,015,247, 5,484,437, 5,489,308, 5,609,636, 5,658,337, 5,741,253, 6,080,155, 6,096,038, 6,264,656 and 6,270,498. These types of systems involve the use of screws that are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it does not effective in preserving the natural motion of the spinal segment into which it is implanted. Other pedicle screw-based systems employ articulating joints between the pedicle screws. Because these types of systems require the use of pedicle screws, implantation of the systems are often more invasive to implant than interspinous spacers.

Where the level of disability or pain to the affected spinal motion segments is not that severe or where the condition, such as an injury, is not chronic, the use of interspinous spacers are preferred over pedicle based systems as they require a less invasive implantation approach and less dissection of the surrounding tissue and ligaments. Examples of interspinous spacers are disclosed in U.S. Pat. Nos. Re. 36,211, 5,645,599, 6,149,642, 6,500178, 6,695,842, 6,716,245 and 6,761,720. The spacers, which are made of either a hard or compliant material, are placed in between adjacent spinous processes. The harder material spacers are fixed in place by means of the opposing force caused by distracting the affected spinal segment and/or by use of keels or screws that anchor into the spinous process. While slightly less invasive than the procedures required for implanting a pedicle screw-based dynamic stabilization system, implantation of hard or solid interspinous spacers still requires dissection of muscle tissue and of the supraspinous and interspinous ligaments. Additionally, these tend to facilitate spinal motion that is less analogous to the natural spinal motion than do the more compliant and flexible interspinous spacers. Another advantage of the compliant/flexible interspinous spacers is the ability to deliver them somewhat less invasively than those that are not compliant or flexible; however, their compliancy makes them more susceptible to displacement or migration over time. To obviate this risk, many of these spacers employ straps or the like that are wrapped around the spinous processes of the vertebrae above and below the level where the spacer is implanted. Of course, this requires some additional tissue and ligament dissection superior and inferior to the implant site, i.e., at least within the adjacent interspinous spaces.

With the limitations of current spine stabilization technologies, there is clearly a need for an improved means and method for dynamic posterior stabilization of the spine that address the drawbacks of prior devices and associated delivery procedures and tooling. In particular, it would be highly beneficial to have a dynamic stabilization system that relies upon an implantation procedure using minimally invasive tooling. It would be additionally advantageous if the implantation procedure were reversible.

SUMMARY

A plurality of individual tools is provided where each tool is uniquely configured to perform a step or a portion of a step in a novel procedure associated with the implantation of a stabilizing device (e.g., an interspinous spacer) for stabilizing at least one spinal motion segment. The tools are usable individually, or more preferably as a tooling system in which the tools are collectively employed to implant an interspinous spacer, generally in a minimally invasive manner. For example, each of the tools is arranged with coordinated markings and/or other features to ensure consistent depths of insertion, proper orientation of the tools with respect to each other or an anatomical feature of the patient, and precise delivery of the spacer to maintain safe positioning throughout the implantation procedure.

DESCRIPTION OF THE DRAWINGS

The invention is best understood from the following detailed description when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIGS. 3 and 3A are pictorial views of an illustrative target needle and inner puncher, respectively;

FIG. 4 is a pictorial view of an illustrative K-wire;

FIG. 4A is a detailed view of an circumferential notch forming a groove in an illustrative K-wire;

FIG. 4B is a detailed view of a circumferential band in an illustrative K-wire;

FIG. 5 is a pictorial view of an illustrative K-wire clamp;

FIG. 5A is a pictorial view of an illustrative K-wire clamp arranged with optional sensor and alarm functions;

FIG. 6 is a pictorial view of a first illustrative dilator;

FIG. 6A is a detailed view of the distal end of the first illustrative dilator shown in FIG. 6;

FIG. 7 is a pictorial view of a second illustrative dilator;

FIG. 7A is a detailed view of the distal end of the second illustrative dilator shown in FIG. 7;

FIG. 11 is a pictorial view of a first illustrative interspinous knife;

FIG. 11A is a detailed view of the distal end of the interspinous knife shown in FIG. 11;

FIG. 11B is a detailed view of the proximal end of the interspinous knife shown in FIG. 11;

FIG. 14 and 14A are pictorial views of a first illustrative insertion instrument;

FIG. 14B is a detailed view of the distal tip of the insertion instrument shown in FIGS. 14 and 14A;

FIG. 14C is a detailed view of the distal tip of the insertion instrument shown in FIGS. 14 and 14A in operative engagement with an interspinous spacer;

FIG. 14D shows a visual scale disposed in the insertion instrument shown in FIGS. 14 and 14A;

FIG. 14E illustrates the deployment positions of an interspinous spacer indicated by the visual scale shown in FIG. 14D;

FIG. 23 is a detailed view of the target needle as inserted to an appropriate depth;

FIG. 23A is a detailed view of the illustrative K-wire of FIG. 4 as inserted through the target needle;

FIG. 23B is a detailed view of the alignment of the K-wire to the target needle;

FIG. 26 is a pictorial view of the second illustrative dilator shown in FIG. 7 as inserted through the supraspinous ligament;

FIG. 26A is a detailed view of the second illustrative dilator as inserted through the supraspinous ligament to an appropriate depth;

FIG. 26B is a detailed view of the alignment of the first dilator to the second dilator;

FIG. 31G is a pictorial view of the insertion instrument of FIGS. 14, 14A, 14B, 14C, 14D showing operation of the handle which rotates a shaft in the elongated tube;

FIG. 31H is a detailed view of the distal end of the elongated tube of the insertion instrument with rotatable shaft;

FIG. 31I shows a visual scale disposed in the insertion instrument shown in FIGS. 31G and 31H;

FIGS. 31J and 31K are pictorial views of an illustrative interspinous spacer in operative engagement with the insertion instrument shown in FIGS. 31G and 31H;

DETAILED DESCRIPTION

Figure 1:
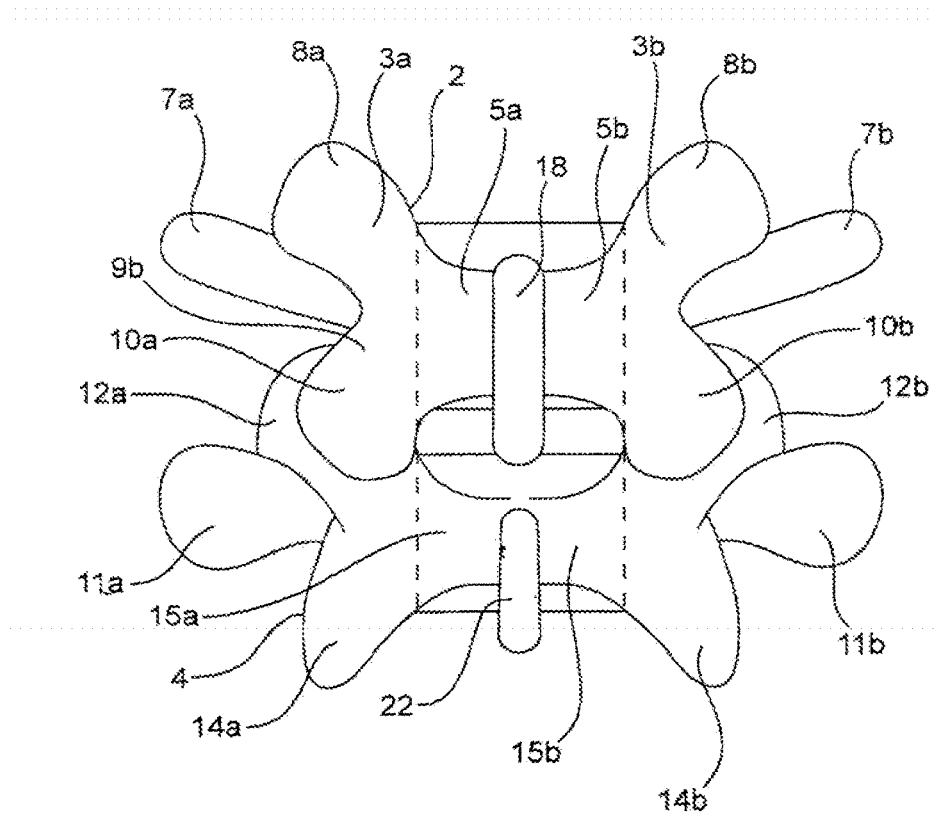
FIG. 1 is a perspective view of a portion of the human spine having two vertebral segments.
Figure 2A:
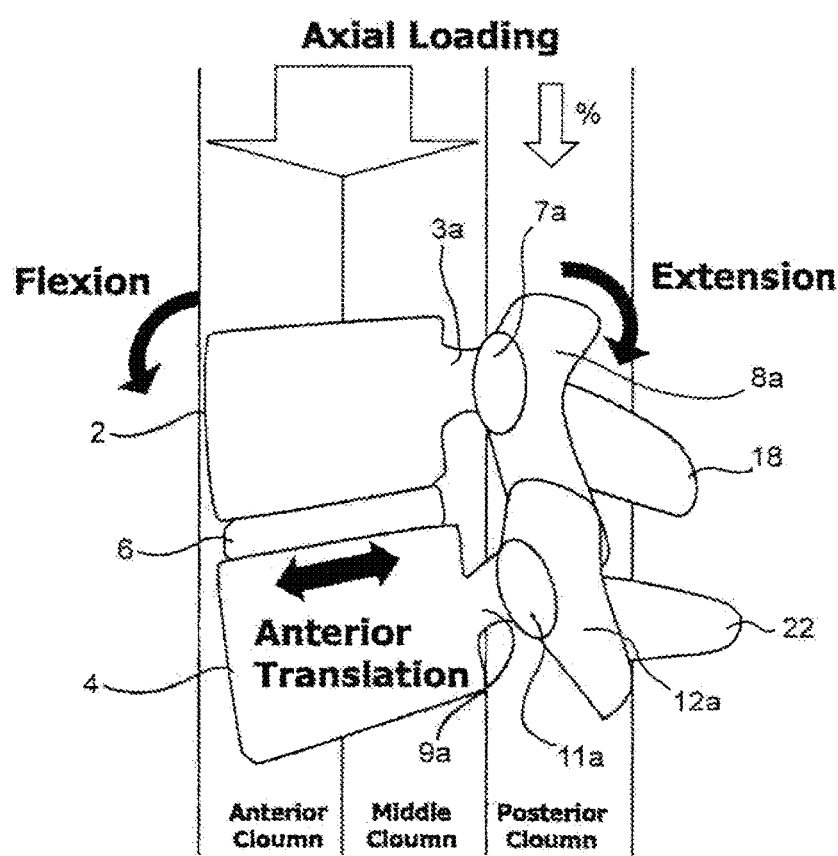
FIGS. 2A, 2B and 2C illustrate left side, dorsal and top views, respectively, of the spinal segments of FIG. 1 undergoing various motions.
Figure 2B:
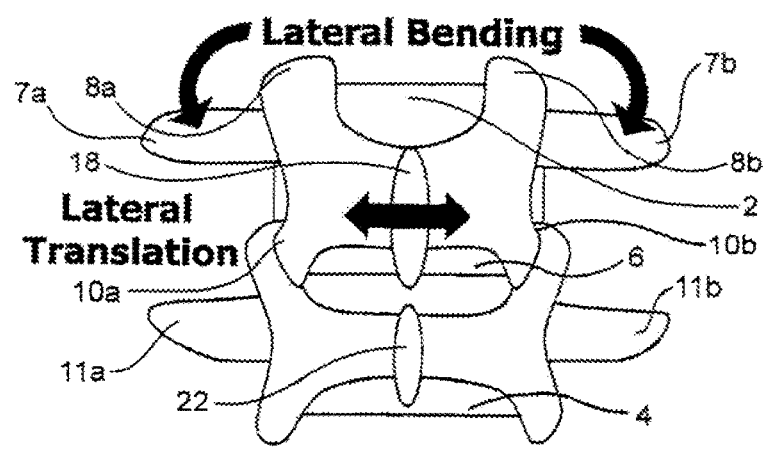
Figure 2C:
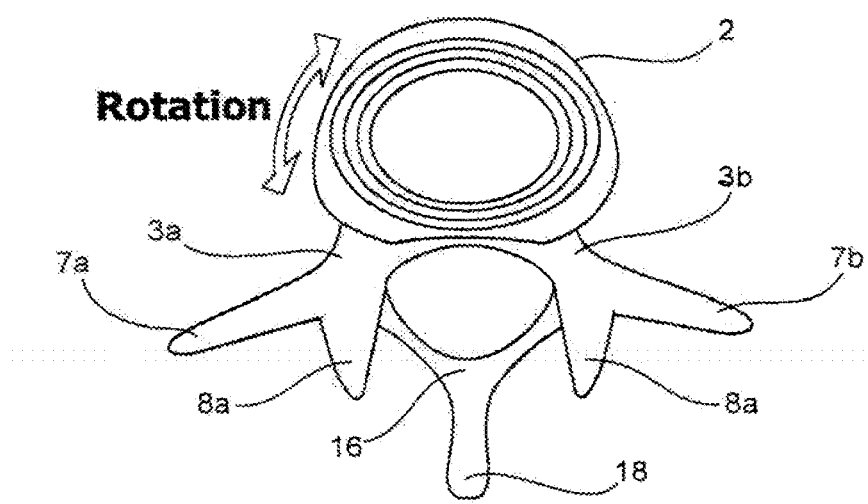

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinous process" may include a plurality of such spinous processes and reference to "the marker" includes reference to one or more markers and equivalents thereof known to those skilled in the art, and so forth.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in greater detail by way of the following description of exemplary embodiments and variations of the devices and methods of the present invention. The invention generally includes a group of tools arranged for the percutaneous implantation of an interspinous spacer using an inventive method. A key feature of the interspinous spacer device is that it is expandable from a low profile configuration to a higher profile or operative configuration. This design allows the device, when in the low profile condition, to be delivered percutaneously through use of the tooling without requiring the removal of any portion of the spinal motion segment into which the device is implanted.

Each of the tools shown in the FIGS. and described in the accompanying text are advantageously used as part of as a tooling system to perform the inventive method. That is, the tools are arranged to be used as a group—each tool in combination with others and/or sequentially as described in detail below. Accordingly, the tools generally are configured with coordinated markings and/or features to enable the tools to be used cooperatively and to ensure consistency of operation during the implantation procedure. For example, as noted above and without limiting the invention, each of the tools is arranged with coordinated markings and/or other features to ensure consistent depths of insertion, proper orientation of the tools with respect to each other or an anatomical feature of the patient, and precise delivery of the spacer to maintain safe positioning throughout the implantation procedure.

However, while use of the tools as a tooling system is preferable in some applications of the invention, it is emphasized that each tool may also be beneficially and advantageously utilized alone or in subset combination with other tools, but without using all of the tools in the tooling system. Thus while the utilization of the entire set of tools in the tooling system is often beneficial in many applications, it is not mandatory.

In addition, each of the tools shown in the FIGS. and described in the accompanying text are advantageously utilized to perform the inventive percutaneous spacer implantation in a minimally invasive manner so as to minimize the affect of the procedure on the patient's tissues and, in particular, the supraspinous ligament. Utilization of such minimally invasive techniques can shorten the procedure's time and speed recovery by the patient. However, the application of the tools in a minimally invasive manner is not a requirement in order to realize many of the benefits provided by the tooling.

Referring now to FIGS. 3 and 3A, pictorial views of an illustrative target needle 305 and inner puncher 312 are respectively provided. The target needle 305 and inner puncher 312, when assembled (e.g., locked) together, function to place a guidewire (e.g., a K-wire) through the patient's skin into an area which neighbors a vertebral segment of interest. Accordingly, target needle 305 and inner puncher 312 are configured to penetrate the supraspinous ligament and other tissue. Target needle 305 and inner puncher 312 are preferably disposable tools (i.e., arranged as single use instrumentalities in most applications of the invention).

Both the target needle 305 and inner puncher 312 are arranged with graspers on the proximal ends as indicated by reference numerals 318 and 321. Target needle 305 further includes wings 325 that are arranged to facilitate gripping of target needle 305 by an operator.

Target needle 305 includes a hollow needle portion 327 that is arranged to removably receive a needle portion 330 of the inner puncher 312, typically in a close-fitting manner. That is, the outside diameter of the needle portion 330 is sufficiently close in dimension to the inner diameter of the hollow needle portion 327 so that the inner puncher 312 is substantially radially fixedly positioned once needle portion 330 completes its slideable engagement with hollow needle portion 327. Both the hollow needle portion of target needle 305 and the needle portion 330 of inner puncher 312 are preferably composed of stainless steel for most applications of the invention and are thus configured to be visible using fluoroscopy to assist insertion to the desire depth. The inner diameter of target needle 305 is further selected to allow the removable insertion of a guidewire.

Target needle 305 and inner puncher 312, in this illustrative example, are further configured with a positive attachment comprising a threaded-type connection or, as shown in FIGS. 3 and 3A, a rotatably engagable bayonet-type lock. In this arrangement, a pin 321 radially extends from a distal portion of the target needle 305. Pin 321 rotatably lockably engages with a mating slot 336 disposed in a lower portion of the grasper 321 when the inner puncher 312 is fully inserted through the needle portion 327 of target needle 305. When thus locked, the inner punch 312 is substantially fixedly radially and axially located within target needle 305. By anti-rotating the inner punch 312 with respect to the target needle 305, the inner punch 312 is unlocked so it can be removed from the target needle 305.

Inner puncher 312 includes a sharpened portion 335 at the distal end of the needle portion 330 as shown. The needle portion 330 of inner puncher 312 is configured (i.e., has sufficient length) so that the sharpened portion 335 is exposed when the inner puncher 312 is inserted into the hollow needle portion 327 of the target needle 305 and locked into position.

In an optional arrangement for the target needle 305, an energy delivery functionality is provided whereby an energy delivery unit (not shown) such as an RF (radio frequency) unit is operatively coupled to the distal end of the target needle 305 and/or inner puncher 312. Such energy delivery functionality may be utilized to assist with skin or other tissue penetration or blood coagulation, for example.

In another optional arrangement, target needle 305 and/or inner puncher 312 are arranged with one or more markers such as ultrasonic, magnetic, or other types of markers. Use of such markers may advantageously reduce or eliminate the need for fluoroscopic imaging in some applications of the invention.

FIG. 4 is a pictorial view of an illustrative K-wire 402 that is arranged to be inserted through the target needle 305 (FIG. 3) after the inner punch 312 (FIG. 3) is unlocked and removed. K-wire 402 functions to allow one or more devices to be placed over it to a particular anatomical location. K-wire 402 includes a groove 406 which is also shown in the detailed view of FIG. 4A. Groove 406 is arranged as a circumferential notch in most applications of the invention and provides for depth placement on a matched basis among the one or more devices. Accordingly, groove 406 is spaced at a specific depth relative to the end of the target needle 305.

K-wire 402 is constructed from stainless steel in a similar manner to conventional guidewires. K-wire 402 may alternatively include other depth markings such as circumferential markers (not shown) or be arranged to be radiopaque (i.e., not allow X ray or other radiation to penetrate) or include radiopaque sections. K-wire 402 is preferably arranged as a disposable or single-use tool.

In an optional arrangement for K-wire 402, a circumferential band 412 is disposed along its length as shown in FIG. 4B. Circumferential band 412 provides for depth placement in a similar manner as groove 406, and may also be utilized to perform as a mechanical stop to limit the advancement of the K-wire 402 through the target needle 305.

In another optional arrangement, K-wire 402 is arranged with one or more markers such as ultrasonic, magnetic markers or other marker types, for example, to avoid the need for fluoroscopy.

FIG. 5 is a pictorial view of an illustrative K-wire clamp 505 that, when placed by an operator on a guidewire such as K-wire 402 (FIG. 4) near the tissue entry site, functions to stabilize the guidewire. Such stabilization may be helpful to prevent further insertion of the guidewire beyond a desired depth and unwanted inadvertent movement of the guidewire.

K-wire clamp 505 is generally configured in a hinged clamp arrangement in most applications of the invention in which each clamp portion is biased with a spring (e.g., a torsional spring) to provide a desired level of clamping pressure on the guidewire. K-wire clamp 505 is preferably arranged as a disposable or single-use tool.

In an optional arrangement for K-wire clamp 505A, a slip sensor 510 and/or alarm transducer 517 are disposed along portions of the K-wire clamp 505 as shown in FIG. 5A. If slippage (i.e., relative movement between the K-wire clamp 505 and the guidewire) beyond a predetermined threshold is detected by slip sensor 510, then a signal over signal path 522 triggers the alarm transducer 517 to transmit an alarm to an alarm receiving location or alarm monitor (not shown). In such optional arrangement, K-wire clamp 505A provides a positive indication such as a visual indicator (e.g., activation of a light source such as a light emitting diode) or audible alarm (e.g., activation of a tone generator or buzzer) in the event that the K-wire clamp is inadvertently opened (either completely or partially) or the guidewire slips. Slip sensor 510 is alternatively arranged as a magnetic sensor or electrical/resistance-sensing sensor, for example.

Referring to FIGS. 6, 6A, 7 and 7A, pictorial and detailed views of two illustrative dilators are shown. FIG. 6 is a pictorial view of a first illustrative dilator 605 that is arranged with a through channel that slidably engages with a guidewire such as K-wire 402 (FIG. 4) and is inserted through the supraspinous ligament. When used alone or in combination with the second illustrative dilator 705 shown in FIGS. 7 and 7A, dilator 605 progressively (or sequentially) dilates tissue to thereby enable insertion of devices through the dilated opening.

Dilators 605 and 705 are preferably radiopaque and arranged as disposable, single use tools in most applications of the invention. Dilators 605 and 705 are typically constructed from stainless steel, titanium or similar materials. Dilator 605 includes a grip portion 607 at the proximal end, which in this illustrative example, is arranged as series of rings that alternate with recessed portions. Dilator 705 is arranged with a similar grip portion 707. A grip portion employing knurling or other material texturing may be alternatively utilized with either or both dilators 605 and 705 in some applications of the invention.

Dilator 605 includes a groove 611, for example a circumferential notch, that functions as a visible depth marker. Dilator 705 is similarly arranged with a groove 711. Dilators 605 and 705 may optionally include other markers such as ultrasonic, magnetic or other markers, for example, to avoid the need for fluoroscopy.

Dilator 605 is arranged, in this illustrative example, with a mid-line/orientation indicator such as a longitudinal groove 615 that is disposed substantially along the entire length of the dilator (i.e., from the proximal to distal end). Such mid-line/orientation indicator provides a visual marker that assists proper insertion of the dilator 605. Dilator 705 is also arranged with a longitudinal groove 715 in a similar manner.

Dilators 605 and 705 share similar construction and features but differ in size, notably inside and outside diameters (ID and OD, respectively). The respective diameters are selected such that dilator 605 and 705 are mateably and slidably engagable (i.e., in a telescoping manner). In this illustrative example, the OD of dilator 605 is 5 mm and the OD of dilator 705 is 9.3 mm.

Dilator 605 includes a tapered portion 621 at its distal end in which a spinous process channel 626 is disposed. The spinous process channel 626 is configured to align and/or mateably engage with a spinous process to thereby maintain a desired mid-line position of the dilator 605. In addition, the spinous process channel may be utilized to distract tissue whereby a forward force is applied. A scalloped leading edge 630 is optionally disposed at the tapered portion 621 of dilator 605 which is arranged to facilitate insertion of the dilator through the tissue while minimizing tissue trauma.

Dilator 705 also includes a tapered portion 721 and a spinous process channel 726 that are each configured in a similar manner as those corresponding features in dilator 605. A scalloped leading edge 730 is preferably included along the far distal end of dilator 705.

The tapered portions 621 and 721 of dilators 605 and 705, respectively, are preferably sized, when inserted, to end on the anterior side of the supraspinous ligament (which can be verified under fluoroscopy or other visualization means such as ultrasound). Such arrangement is intended to minimize damage to the supraspinous ligament since any trauma to underlying tissue is less consequential. Table 1 below provides illustrative key dimensions for dilators 605 and 705.

TABLE 1

| | Taper Length | Taper Angle | Spinous Process Channel Length | Channel Taper |
|---|---|---|---|---|
| Dilator 605 | 0.250 in. | 27 degrees | 0.225 in. | 27 degrees |
| Dilator 705 | 0.570 in. | 17 degrees | 0.530 in. | 15 degrees |

Dilators 605 and 705 are each optionally arranged to include an energy delivery functionality using an operatively coupled energy delivery unit (not shown) such as an RF (radio frequency) unit. In most applications, the energy is delivered through the sip of the dilator to assist with tissue penetration or coagulation.

In an alternative arrangement, a third dilator (not shown) is also utilized. Such third dilator is intermediately-sized between dilator 605 and dilator 705. Accordingly, the third dilator is configured with appropriate inside and outside diameter dimensions to be slidably engaged over the OD of dilator 605 and slidably inserted into the ID of dilator 705, typically in a close-fitting arrangement.

In a second alternative arrangement, a longitudinally oriented, relatively narrow opening such as a slit (not shown) is disposed substantially along the length of dilator 605 and/or dilator 705. Such a feature enables the dilator to be removed from the guidewire without requiring the retraction of the full length of the guidewire. For example, the dilator can be simply removed by passing the guidewire through the longitudinal opening to thereby clear an object or device at the proximal end of the guidewire.

FIGS. 8, 8A, 8B and 8C show pictorial views of an illustrative mounting bracket 802 in various alternative arrangements. Mounting bracket 802 functions to create a stable working platform by holding an elongated device such as a cannula in a fixed position. Mounting bracket 802 is generally positioned over the dilator 705 (FIG. 7) prior to the insertion of a cannula. Alternatively, mounting bracket 802 may be positioned after the insertion of the cannula.

Figure 8:
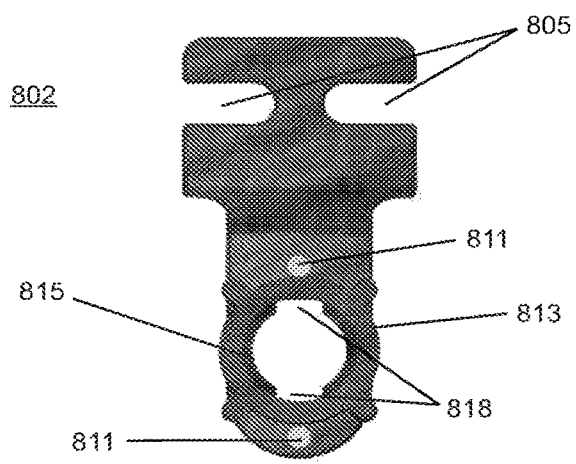
FIGS. 8, 8A, 8B and 8C show various pictorial views of an illustrative mounting bracket in various alternative arrangements.

Mounting bracket 802 is typically further attached to a stabilizing device (such as that shown in FIG. 10) using a dual mounting slot arrangement 805 as shown in FIG. 8, or a single mounting slot 807 in base 809. The alternative mounting slot arrangements enable such a stabilizing device to be attached to the superior or inferior ends of mounting bracket 802 (using slot arrangement 805) or laterally (i.e., left or right, using the mounting slot 807). The other end of the stabilizing device is typically fixedly attached to a table or other immobile object. In addition to slots, mounting through-holes are alternatively utilizable for some applications. In alternative arrangements, mounting bracket 802 is configured for attachment directly to the patient (instead of, for example, a table-mounted stabilizing device) through use of adhesives or sutures for skin-mounting or via screws or other mechanical fasteners for bone-mounting.

Base 809 may be optionally arranged to include unique markings which, in this illustrative example, are arranged as dots 811. For example, radiopaque markings or conventional visible markings are usable to assist with alignment, depth control, or mating with other discrete devices or tools. Alternatively, the markings may be arranged using ultrasonic, magnetic or other marker-types, for example, to avoid the need for fluoroscopy.

Mounting bracket 802 thus facilitates the alignment of the cannula with the spine so that an operator may select a desired trajectory and orientation of the cannula into the tissue. That is, mounting bracket 802 with the associated stabilizing device provides positive control of axial, sagittal and coronal positioning of the interspinous spacer as implanted by the present procedure and tooling.

Figure 8A:
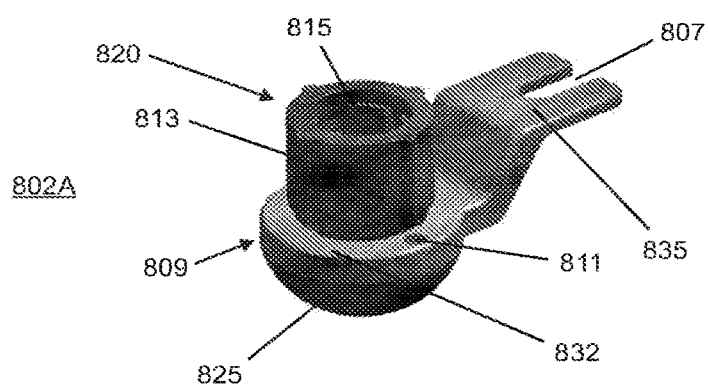

As shown in FIG. 8A, mounting bracket 802A includes a single threaded nut 813 that is rotatably coupled to an externally threaded cylinder 815 having a cylindrically shaped passageway through which the tool is inserted. Cylinder 815 includes one or more longitudinally oriented slots 818 (FIG. 8) that enable the walls of the cylinder 815 to move slightly radially inward to thereby provide a clamping force against the inserted tool when the nut 813 is tightened on the threads of the cylinder 815. The inner walls of the cylinder are optionally configured with projections or texturing to enhance the grip on the tool. Accordingly, nut 813 and cylinder 815 combine to form a receiving tube 820 that surrounds and clamps a portion of the tool's elongated element (which is generally a tubular element).

Figure 8B:
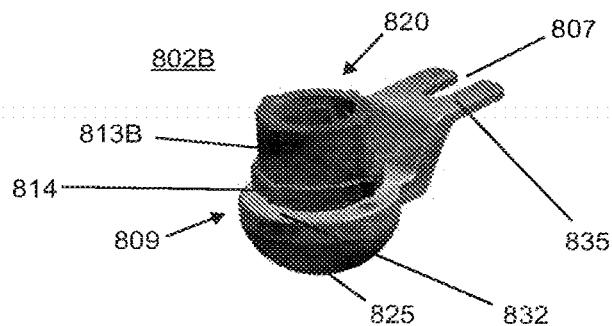

In FIG. 8B, mounting bracket 802B includes an alternative dual nut design using a primary threaded nut 813B and a secondary locking threaded nut 814. Primary nut 813B is first tightened to fixedly clamp the tool's elongated element in the receiving tube 820. Secondary nut 814 is then tightened to thereby lock the primary nut 813B in place. Other locking-type arrangements are also usable in some applications. For example, a nylon or other plastic insert (not shown) is disposed around the inner threaded portion of nut 813 to provide anti-rotation capabilities. A clutch-type mechanism (not shown) that slips upon teaching a predetermined torque or engagement travel may also be incorporated into the nut/cylinder arrangement. In addition, a positive locking arrangement such as push-to-turn or lift-to-turn (as commonly used in child-proof medicine containers) may be employed in the nut/cylinder mechanism in those applications where a positive lock and unlock feature is desirable.

Mounting bracket 802 is typically arranged, in most applications of the invention, with a semi-spherical projection 825 that is disposed on a bottom surface of the base 809 so that the spherical portion of the projection 825 projects substantially downward when mounting bracket 802 is oriented as shown in the FIGS. 8A and 8B. Projection 825 functions to substantially fill the area between the base 809 and the patient's tissue to thereby assist with stabilization of the mounting bracket 802. The semi-spherical shape of projection 825 provides for such stabilization while simultaneously allowing rotation about three axes (i.e., yaw, pitch and roll) to facilitate setting of the trajectory of a coupled tool such as a cannula.

Base 809 of mounting bracket 802 is arranged in a stepped, or dual plane, configuration in the illustrative example shown in FIGS. 8, 8A and 8B. Base 809 includes a planar portion 832 from which receiving tube 820 upwardly projects and a planar portion 835 in which the one or more mounting slots are disposed. Planar portions 832 and 835 are substantially parallel while being offset to thereby enable mounting bracket 802 to be aligned with the patient's body particularly when using a non-orthogonal tool trajectory. The combination of the dual plane configuration with use of the projection 825 is particularly advantageous in many applications of the invention to provide stability for the mounting bracket 802 over a range of tool trajectories.

Figure 8C:
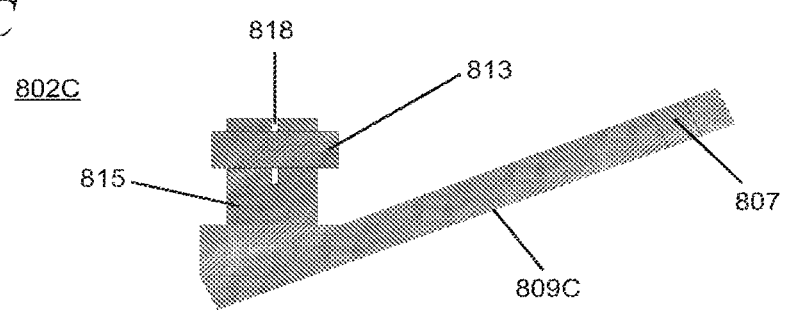

An alternative configuration for the mounting bracket is shown in FIG. 8C. There, mounting bracket 802C employs an angled base 809C that may provide additional flexibility for aligning mounting bracket 802C with the body in some applications of the invention.

Mounting bracket 802 is preferably radiopaque and arranged as a disposable, single use tool in most applications of the invention. Mounting bracket 802 is generally preferred to be of rigid construction to provide for stable orientation of the coupled tool. In most applications of the invention, base 809 is constructed of aluminum with the nut 813 and cylinder 815 being formed from radiopaque plastic such as polyphenylsulfone thermoplastic (sold under the brand Radel® R). Markers 811, when arranged as radiopaque markers, are formed using stainless steel.

In an alternative arrangement, mounting bracket 802 is configured with more than one receiving rube 820 (i.e., more than one nut/cylinder combinations). The other receiving tubes (not shown) may fixedly clamp other tools, instruments or devices such as a laparoscopic camera or light. The other receiving tubes may be oriented with the same trajectory as receiving tube 820, or be oriented orthogonally or at some other trajectory with respect to receiving tube 820.

Figure 8D:
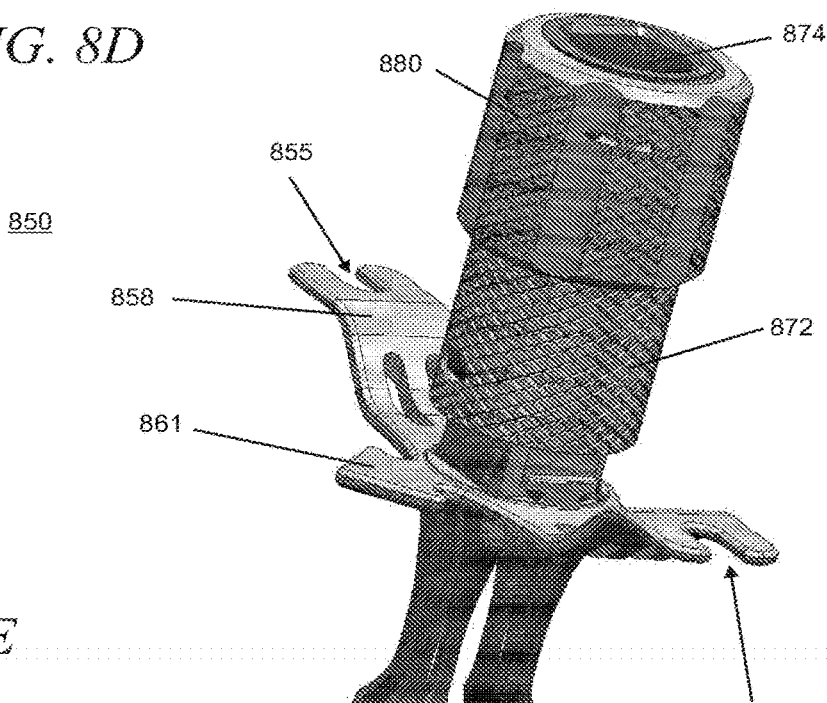
FIGS. 8D-L show various pictorial views of an illustrative mounting tower.
Figure 8E:
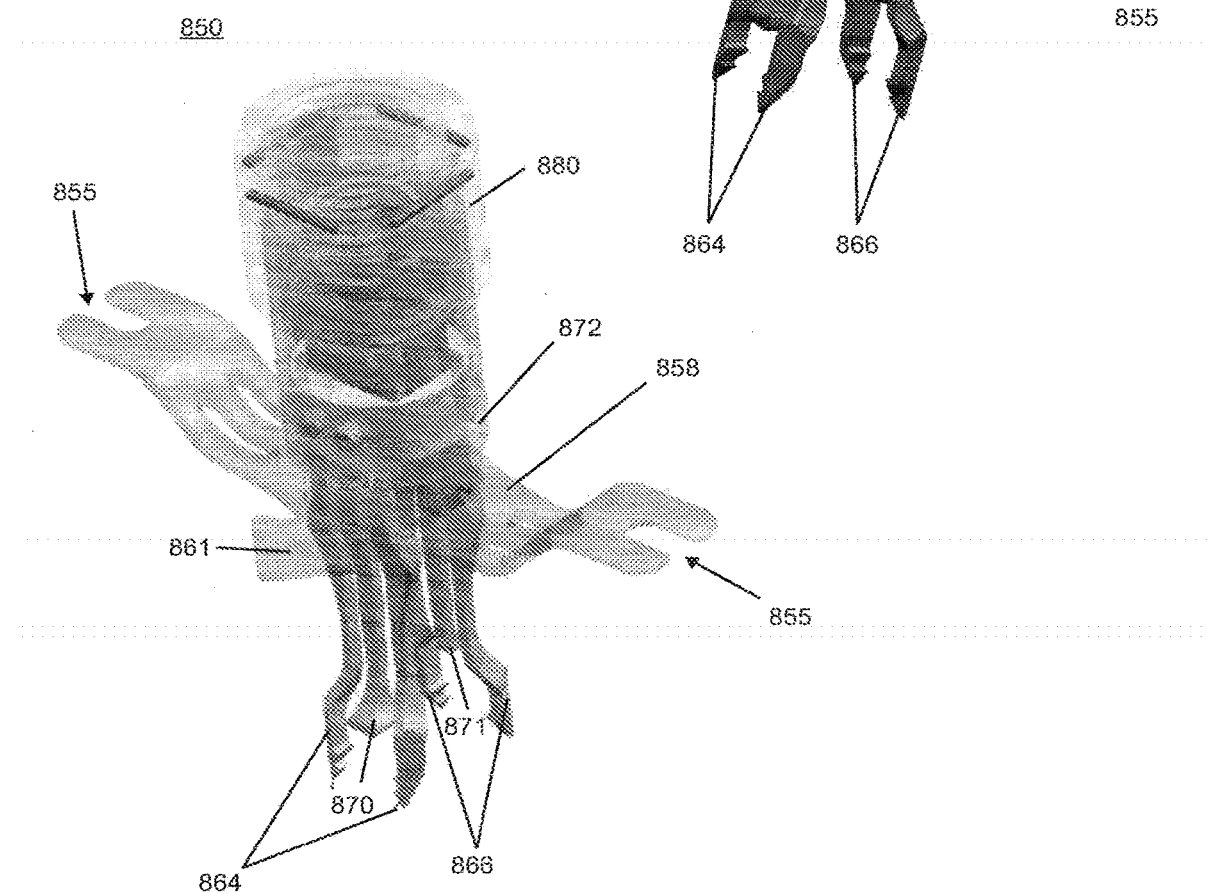
Figure 8F:
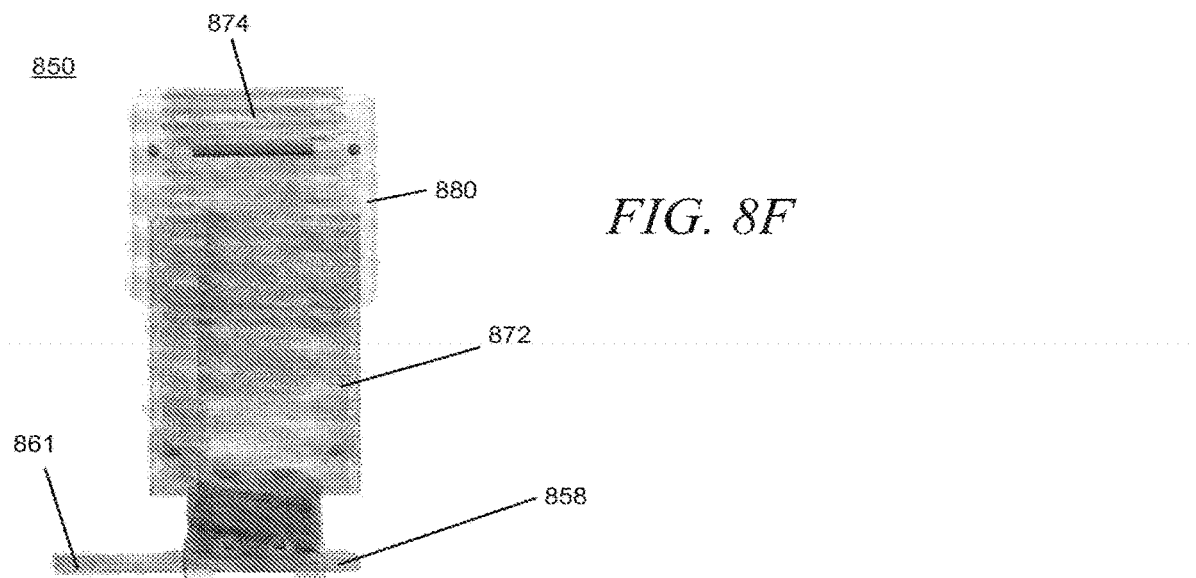

FIGS. 8D and 8E show pictorial views of an illustrative mounting tower 850. Mounting tower 850 is used as an alternative to mounting bracket 802 and similarly functions to create a stable working platform by holding an elongated device such as a cannula in a fixed position. Mounting tower 850 is generally positioned over the dilator 705 (FIG. 7) prior to the insertion of a cannula.

Mounting tower 850 is typically further attached to a stabilizing device (such as that shown in FIG. 10) using a dual mounting slot arrangement 855 in a base 858 as shown in FIGS. 8D and 8E, or alternatively using a single mounting slot or a plurality of mounting slots, i.e., three or more (not shown). The alternative mounting slot arrangements enable such a stabilizing device to be attached to the superior or inferior ends of mounting tower 850 (using slot arrangement 855) or laterally (i.e., left or right, using a mounting slot 855). The other end of the stabilizing device is typically fixedly attached to a table or other immobile object, in addition to slots, mounting through holes are alternatively utilizable for some applications. In alternative arrangements, mounting tower 850 is configured for attachment directly to the patient (instead of, for example, a table-mounted stabilizing device) through use of adhesives or sutures for skin-mounting or via screws or other mechanical fasteners for bone-mounting.

Mounting tower 850 includes a pointing arrow 861 (such as a Cephalad indicator) that, in this illustrative example, is integrally formed with and laterally extending from base 858.

Figure 8G:
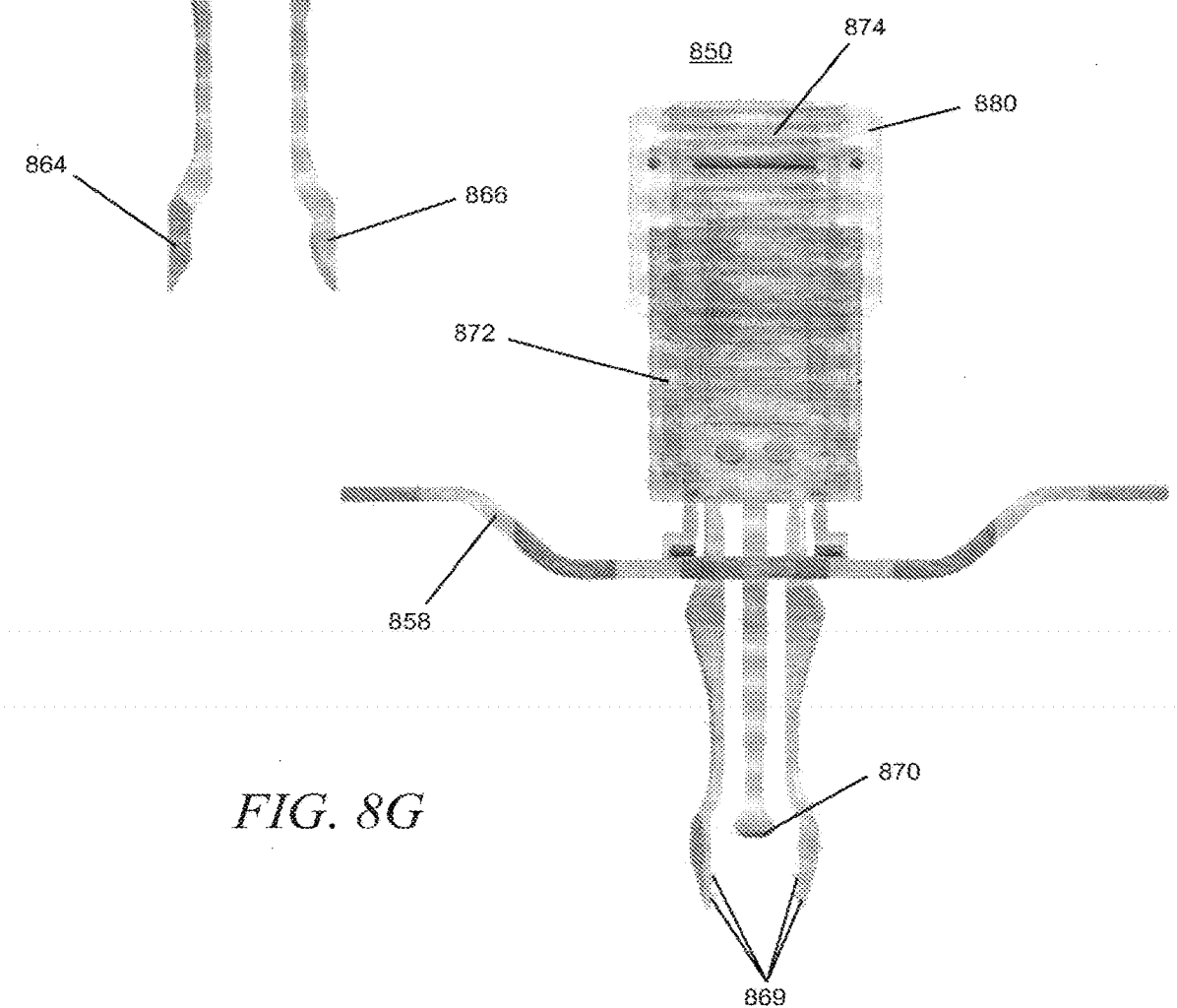

Mounting tower 850 is arranged with two pairs of spinous process grippers indicated by reference numerals 864 and 866 in FIGS. 8D and 8E. Each spinous process gripper pair comprises two longitudinally extending, opposing, pivotally-mounted legs. Opposing gripping surfaces are disposed at the distal ends of the legs and are arranged with a plurality of laterally inwardly extending serrated edges 869 in FIG. 8G. When the mounting tower 850 is in a fully deployed condition, spinous process grippers 864 are arranged to clamp to the superior spinous process and spinous process grippers 866 clamp to the inferior spinous process.

Mounting tower 850 further includes a superior depth post 870 and an inferior depth post 871 which project axially downward from the base 858. Superior depth post 870 is disposed substantially between the legs of spinous process gripper 864. Inferior depth post 871 is disposed substantially between the legs of spinous process gripper 866. Posts 870 and 871 function as depth stops. Thus, posts 870 and 871 are arranged to interface with the posterior side of the supraspinous ligament so as to thereby limit the travel of the mounting tower 850 and position the spinous process grippers 864 and 866 in an appropriate orientation with respect to the spinous processes. In this illustrative example, inferior depth post 871 is shorter than superior depth post 870 so as to provide some angular freedom of motion in the plane including the longitudinal axis of the supraspinous ligament.

Mounting tower 850 thus facilitates the alignment of the cannula and subsequently utilized tools or devices with the spine so that an operator may select a desired trajectory and orientation of the cannula into the tissue. That is, mounting tower 850 with the associated stabilizing device provides positive control of axial, sagittal and coronal positioning of the interspinous spacer as implanted by the present procedure and tooling.

Mounting tower 850 includes a rotatably-mounted lower cylindrically-shaped collar 872 that extends axially upwards from base 858. Collar 872 rotates about a spindle 873 having a receiving tube (i.e., lumen) therethrough. Collar 872 is operatively coupled using a linkage that is internally disposed in mounting tower 850 to the spinous process grippers 864 and 866. Collar 872 is biased against an internally disposed spring to hold the collar 872 against an internally disposed stop. The stop prevents rotation of the collar 872 until the collar 872 is pushed axially downward against the spring bias to thereby disengage from the stop and rotate freely.

Collar 872 includes surface features, for example knurling, to enhance the operator's grip on the collar 872 when being manipulated.

Figure 8H:
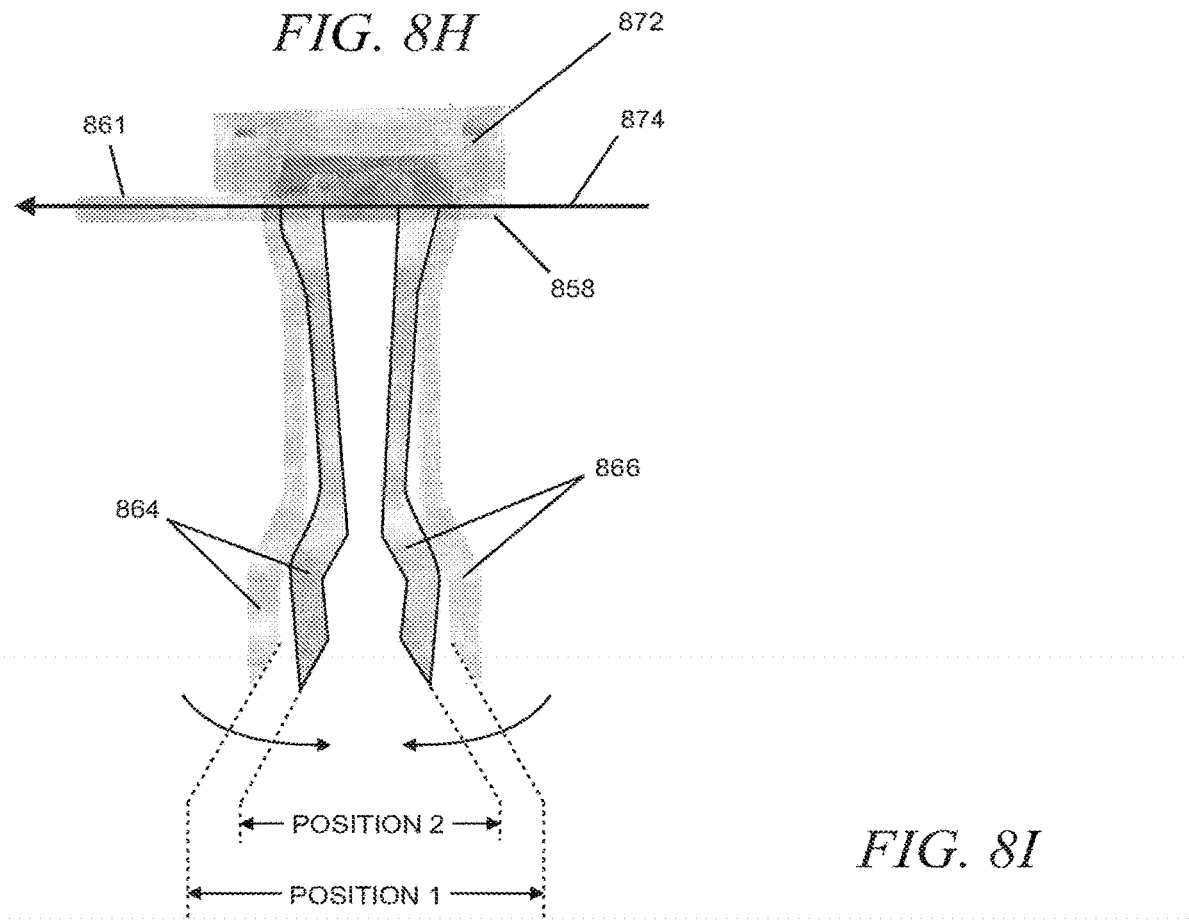

An internally disposed spring normally biases the spinous process grippers 864 and 866 outwardly as indicated by Position 1 in FIG. 8H. The internal linkage is arranged so that rotation of the collar 872 causes movement of the spinous process grippers 864 and 866. In particular, clockwise rotation (when looking axially downward from the orientation of the mounting tower 850 shown in the figures) of collar 872 causes relative inward motion of spinous process grippers 864 with respect to spinous process grippers 866 as indicated by the arrows in FIG. 8H until the spinous process grippers 864 and 866 reach Position 2. As shown, the direction of motion of the spinous process grippers 864 and 866 are in planes which are substantially parallel to the line 874 defined by the longitudinal axis of pointing arrow 861 (i.e., Cephalad indicator).

Figure 8I:
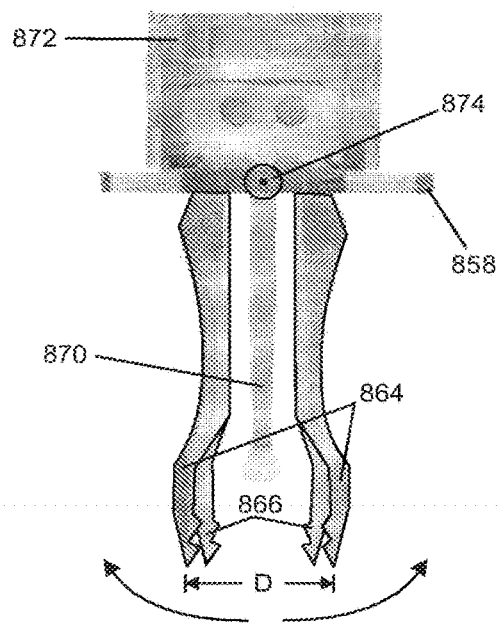

Clockwise rotation of collar 872 further causes relative outward motion of the opposing legs in each pair of the spinous process grippers 864 and 866 as indicated by the arrows in FIG. 8I. As shown, the direction of motion of each of the opposing legs are in planes that are substantially perpendicular to the line 874 which is defined by the longitudinal axis of pointing arrow 861 (i.e., Cephalad indicator).

Typically, collar 872 is rotated clockwise to place the pairs of spinous process grippers 864 and 866 into a "ready" position prior to deployment. That is, the above-described inward motion of the spinous process grippers 864 and 866 reduces the size of the incision required to pass the spinous process grippers 864 and 866 into the operative position with respect to the spinous processes. In addition, the above-described outward motion of the legs in each pair of spinous process grippers 864 and 866 ensures that a sufficient distance "D," as indicated in FIG. 8I, is obtained for the legs to pass over the entire width of the supraspinous ligament as is required to clamp to the spinous processes.

Figure 8J:
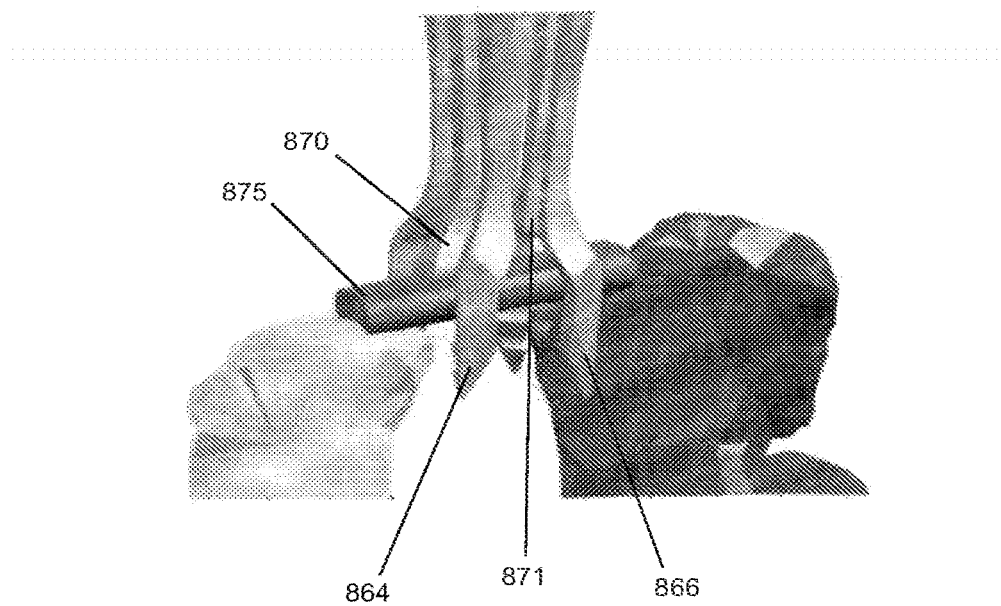
Figure 8K:
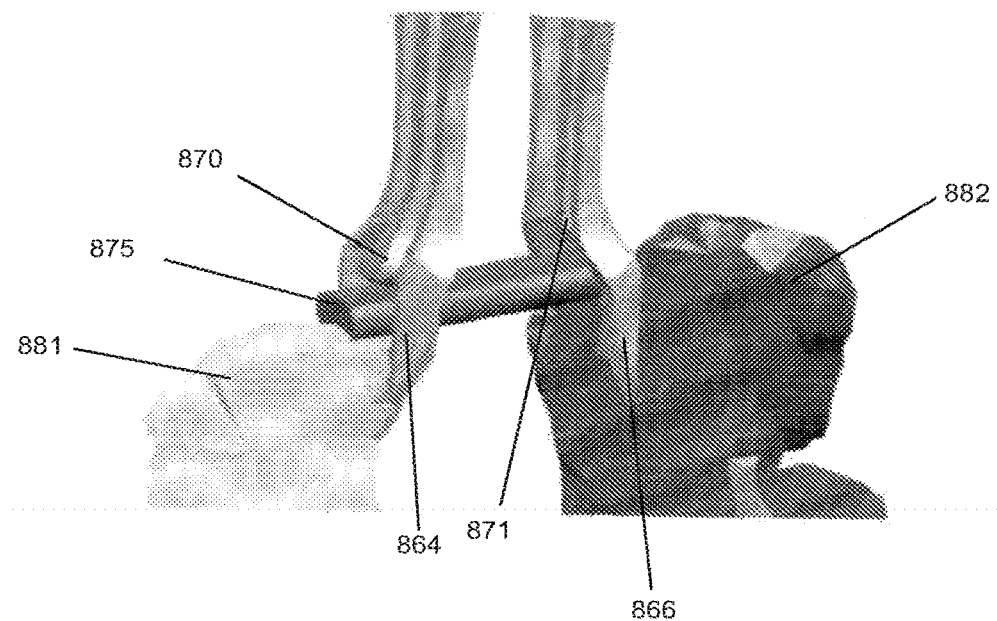

FIG. 8J shows the position of the spinous process grippers 864 and 866 as placed in the ready position through clockwise rotation of collar 872 and positioned over the supraspinous ligament 875. Rotation of the collar 872 in a counterclockwise direction allows the spinous process grippers 864 and 866 to return to their normal outwardly-disposed position as shown in FIG. 8K.

Mounting tower 850 further includes a rotatably-mounted upper cylindrically-shaped collar 880 as shown in FIGS. 8D-G and FIG. 8L that is axially disposed above collar 872. In this illustrative example, the upper collar 880 is arranged to have a slightly larger diameter than lower collar 875 to thereby allow the upper collar 880 to be disposed in a partially overlapping annular manner with respect to the lower collar 875. Collar 880 is arranged in a similar manner as collar 872 with surface features, such as knurling, to enhance gripping by the operator.

Figure 8L:
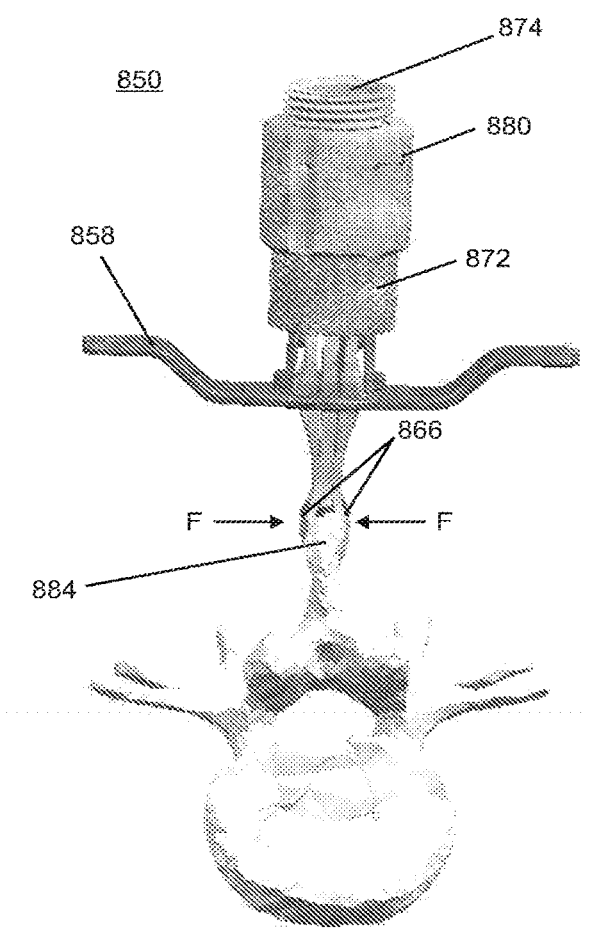

Collar 880 is threadedly engaged with the spindle 873 Clockwise rotation of collar 880 thus causes the spindle 873 to move axially upwards with respect to the collar 880. An internally disposed linkage couples spindle 873 to the spinous process grippers 864 and 866 and is configured so that the axial upward motion of the spindle 873 causes the opposing legs in each spinous process gripper to move inwards and clamp the spinous processes, i.e., the superior spinous process 881 and inferior spinous process 882. Continued clockwise rotation of collar 880 by the operator functions to put sufficient clamping force "F" as shown in FIG. 8L, on the spinous processes (collectively designated by reference numeral 884) by the spinous process grippers 864 and 866 to thereby hold the mounting tower 850 securely to the patient's spine.

In alternative arrangements, mounting tower 850 may be arranged with a single set of spinous process grippers or more than two pairs of spinous process grippers. In addition, while rotatably-configured actuation is often preferable, other mechanisms including levers and other linear-type actuators are also usable. Mounting tower arrangements using multiple receiving tubes are also contemplated as being desirable in some applications.

Mounting tower 850 is beneficially arranged, in most applications, as a reusable, or multiple-use tool. Mounting tower 850 is generally preferred to be of rigid construction to provide for stable orientation of the coupled tool. In most applications, mounting tower 850 utilizes metal construction.

Mounting tower 850 may be optionally arranged to include unique markings. For example, radiopaque markings or conventional visible markings are usable to assist with alignment, depth control, or mating with other discrete devices or tools. Alternatively, the markings may be arranged using ultrasonic, magnetic or other marker-types, for example, to avoid the need for fluoroscopy.

Figure 9:
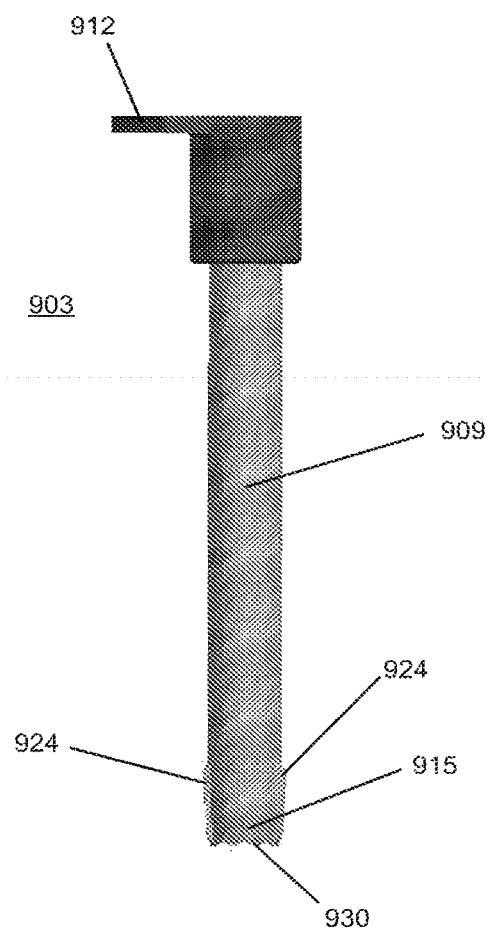
FIGS. 9, 9A and 9B are a side, and two perspective views, respectively, of an illustrative cannula.
Figure 9A:
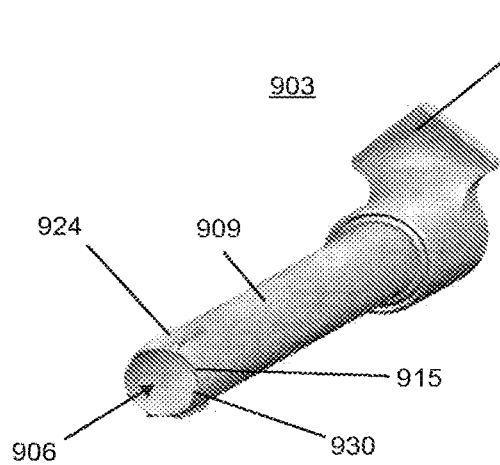
Figure 9B:
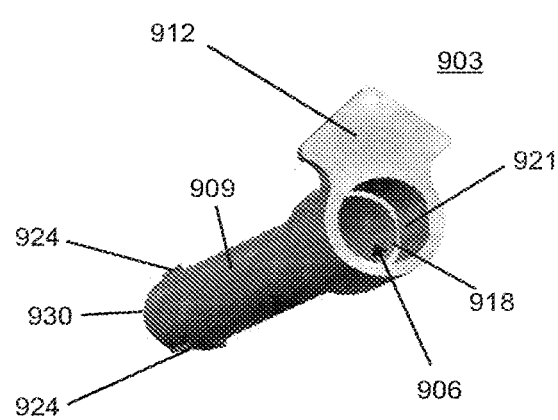

FIGS. 9, 9A and 9B are side, and two perspective views, respectively, of an illustrative cannula 903. Cannula 903 is arranged to be fixedly attached (i.e., clamped) in mounting bracket 802 (FIG. 8) to ensure proper orientation of the cannula 903 and delivery of the interspinous spacer in a desired manner. An internal lumen 906 in cannula 903 allows implants such as the interspinous spacer to pass through and is further configured in diameter and length to mate with devices and the present tools. Such mating may be performed in a fixed arrangement using a clamp or other removably coupling device (not shown). Cannula 903 thereby provides alignment and depth control, for example, via mechanical surfaces, visual markers and other indicators as described below. Cannula 903 may also be used, in some applications of the invention, to distract (i.e., push forward) the spinous processes or tissue. It is noted that the ID of the cannula 903 will typically vary according to the size of the interspinous spacer being implanted.

Cannula 903 is preferably arranged as a disposable, single use tool in most applications of the invention. Cannula 903 is typically constructed from a metal elongated tube 909 and includes a pointing arrow 912 (such as a Cephalad indicator) at the proximal end that provides a reference orientation along the mid-line towards the head. Cannula 903 includes a tapered tip 915 at the distal end.

The proximal end further includes a counterbore 918 that extends partially longitudinally inward (towards the distal end of cannula 903) and a flat 921 disposed on the inside wall of cannula 903 formed by the counterbore 918. Counterbore 918 and flat 921 are examples of mechanical surfaces disposed on or within cannula 903 that function to provide visual or mechanical alignment. For example, counterbore 918 and flat 921 provide alignment for devices or tools that are subsequently inserted into cannula 903 and/or provide a fixed insertion depth.

Tapered tip 915 includes one or more tapered spinous process channels 924 which are configured to align and/or mateably engage with a spinous process to thereby maintain a desire position of the cannula 903. In addition, the spinous process channels 924 may be utilized to distract tissue whereby a forward force is applied. A scalloped leading edge 930 is preferably disposed at the tapered tip 915 which is arranged to facilitate insertion of the cannula 903 through the tissue while minimizing tissue trauma. In particular, the scalloped leading edge 930 may help to part the supraspinous ligament, for example, using a rotating motion of cannula 903. Table 2 below provides illustrative key dimensions for cannula 903.

TABLE 2

| | Taper Length | Taper Angle | Spinous Process Channel Length | Channel Taper |
|---|---|---|---|---|
| Cannula 903 | 0.100 in. | 24 degrees | 0.475 in. | 6 degrees |

Tapered tip 915 may be optionally arranged with an energy delivery functionality using an operatively coupled energy delivery unit (not shown) such as an RF (radio frequency) unit. In most applications, the energy is delivered through the tapered tip 915 of cannula 903 to assist with tissue penetration or coagulation.

As an alternative to the pointing arrow 912 noted above, cannula 903 may include a longitudinal groove or marking that is disposed along the length, or a portion of the length of the elongated tube 909. In addition, cannula 903 is generally arranged to include unique markings, for example, radiopaque markings or conventional visible markings that are usable to assist with alignment, depth control, or mating with other discrete devices or tools. Alternatively, the markings may be arranged using ultrasonic, magnetic or other marker-types, for example, to avoid the need for fluoroscopy.

Figure 10:
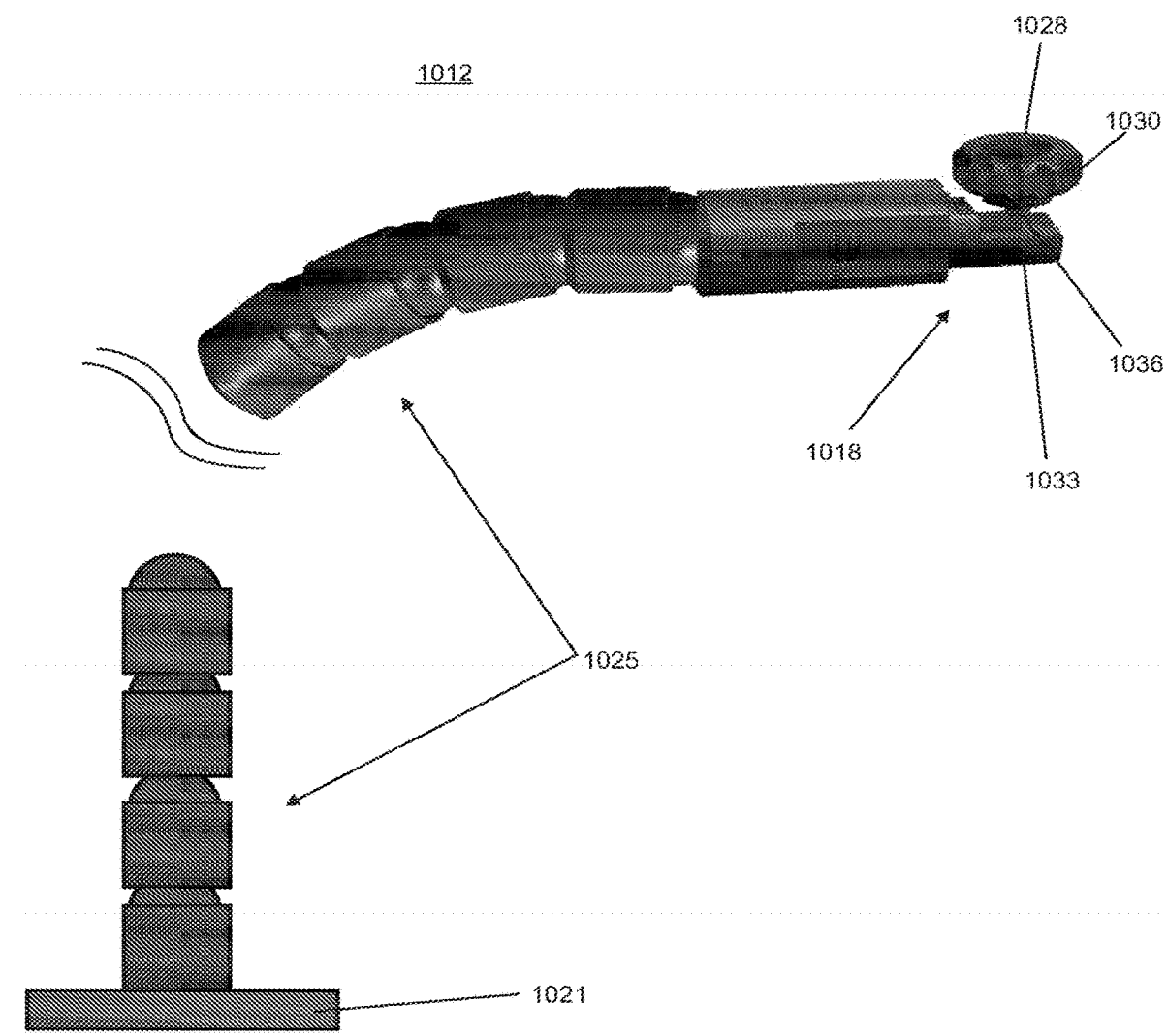
FIG. 10 is a pictorial view of an illustrative flexible stabilizing arm.

FIG. 10 is a pictorial view of an illustrative flexible stabilizing arm 1012. Stabilizing arm 1012 functions to stabilize one or more devices or tools with respect, for example, to the patient or operating table. Stabilizing arm 1012 further enables an operator to make adjustments to the position and trajectory of coupled devices or tools. The stabilizing arm 1012 is preferably arranged as a reusable, or multiple-use tool.

Stabilizing arm 1012 includes a first attachment element 1018 and a second attachment element 1021 as shown in FIG. 10. A flexible (i.e., articulating) portion 1025 couples the first and second attachment elements 1018 and 1021, respectively. As shown in FIG. 10, flexible portion 1025 comprises a plurality of individual ball and socket type elements that enable stabilizing arm 1012 to be manipulated by the operator into a variety of shapes and configurations that are maintained through friction between such elements. While other types of stabilizing arms (e.g., those having fewer degrees of freedom of motion) are also usable in many applications of the invention, a flexible stabilizing arm such as that, shown in FIG. 10 is generally preferred.

First attachment element 1018 is arranged to be removably coupled to a tool or device holding device such as mounting bracket 802 (FIG. 8). As shown in FIG. 10, first attachment element 1018 comprises a threaded screw 1028 having a plurality of gripping ridges 1030 extending radially outward to facilitate threaded screw 1028 to be tightened by hand (i.e., without requiring the use of tools) into the screw receiving portion 1033 of first attachment element 1018. Screw shank 1036 is arranged to engage with a slot or through-hole in mounting bracket 802 to thereby fixedly and removably hold the mounting bracket 802 to the stabilizing arm 1012 when the screw 1028 is tightened.

Second attachment element 1021 is configured for removably or non-removably coupling to a fixture such as an operating table, bed or other fixed or relatively immobile object. For example, second attachment element 1021 is attached to an operating table using mechanical fasteners such as screws or bolts inserted through holes or slots (not shown) in second attachment element 1021. In an alternative arrangement, second attachment element 1021 is configured for attachment directly to the patient (instead of the operating table as provided in the example above) through use of adhesives or sutures for skin-mounting or via screws or other mechanical fasteners for bone-mounting.

In another alternative arrangement, a third attachment element (not shown) is utilized. The third attachment element is disposed between the first attachment element 1018 and second attachment element 1021. Or, the second attachment element 1021 may be disposed between the first attachment element 1018 and the third attachment element. Such a third attachment element advantageously enables, for example, two mounting brackets (such as mounting bracket 903 in FIG. 9) to be presented on a single stabilizing arm.

FIG. 11 is a pictorial view of a first illustrative interspinous knife 1102 which functions to cut through tissue to enable the percutaneous access associated with the subsequent implantation of an interspinous spacer. Interspinous knife 1102 provides a plunge cut-type action through the mechanical manipulation of a plunger 1107 by the operator in a pushing motion, typically by depressing the plunger 1107 with the thumb while gripping the handle portions 1109 with the fingers. The plunge depth is both controlled and adjustable in this illustrative example as described below.

As shown in the detailed view of FIG. 11A, the plunger includes an elongated inner tube 1110 which is rotatably located in the elongated outer tube 1115 of interspinous knife 1102 to thereby enable the operator to make rotations of the cutting blades 1117 disposed at the distal end of the inner tube 1110. As shown, blades 1117 are configured in an "X" pattern, but other blade counts (including a single blade) and patterns are usable depending on the specific requirements of an application of the invention.

Inner tube 1110 is arranged for slideable excursion through the outer tube 115 to effectuate the plunge cutting action, in various alternative arrangements, plunger 1107 is biased against a spring force provided by a spring element (not shown) or is provided with a linear actuator such as a pneumatic actuator or spring loaded actuator. In another alternative arrangement, the plunge cut action is supplied with a mechanical advantage to increase cutting force. For example, a cam or lever type mechanism (not shown) may be utilized to increase the force applied by the blades 1117 by having the operator manipulate an actuating portion of the plunger through an increased distance.

A depth setting slide 1120 is disposed along a top surface of the handle portions 1109 of interspinous knife 1102 as shown in FIGS. 11 and 11B. Depth setting slide 1120 is arranged to move laterally in a sliding motion from a first position as shown in FIG. 11 to a second position as shown in FIG. 11B. When the depth setting slide 1120 is in the first position, the plunge depth of the plunger 1107 is limited to nominally 15 mm. When the depth setting slide 1120 is in the second position, the plunge depth of the plunger 1107 is limited to nominally 20 mm. It is emphasized that such plunge depth settings are illustrative and other plunge depths may be selected according to the specific requirements of an application of the invention.

Interspinous knife 1102 is preferably arranged as a disposable, single use tool in most applications of the invention. Blades 1117 are constructed from stainless steel in most applications of the invention. The remaining components of interspinous knife 1102—including inner tube 1110, outer tube 1115, plunger 1107 and depth setting slide 1120—are generally formed from a polymeric material (i.e. plastic) such as a biocompatible plastic.

In the illustrative example shown in FIGS. 11, 11A and 11B, the inner tube 1110 is arranged to be rotated in an indexed manner. That is, the magnitude of rotation angles and the number of rotated positions of the inner tube 1110 are constrained with respect to outer tube 1115. In other applications, an infinitely rotatable inner tube 1110 is utilizable. It may be particularly beneficial in some applications for an initial plunge cut to be performed followed by a second plunge cut after the blades 1117 are rotated at an angle of 45 degrees to the initial plunge cut.

Interspinous knife 1102 includes a widened shoulder feature 1121 that is configured to engage with the counterbore 918 and flat 921 in cannula 903 (FIG. 9) when the interspinous knife 1102 is inserted through the lumen 906. Such engagement between the shoulder feature and counterbore/flat thereby locates and aligns the interspinous knife 1102 at the proper depth and orientation with respect to the cannula 903 and the spine.

Interspinous knife 1102 is typically arranged with radiopaque or conventional visible markings that are usable to assist with alignment, depth control, or mating with other discrete devices or tools. For example, such markings can be used to indicate the longitudinal position (i.e., plunge depth) or orientation (i.e., rotation angle) of the blades 1117. Alternatively, the markings may be arranged using ultrasonic, magnetic or other marker-types, for example, to avoid the need for fluoroscopy.

Interspinous knife 1102 may be optionally arranged with an energy delivery functionality using an operatively coupled energy delivery unit (not shown) such as an RF (radio frequency) unit. In most applications, the energy is delivered through the blades 1117 to assist with tissue penetration or coagulation.

Figure 11C:
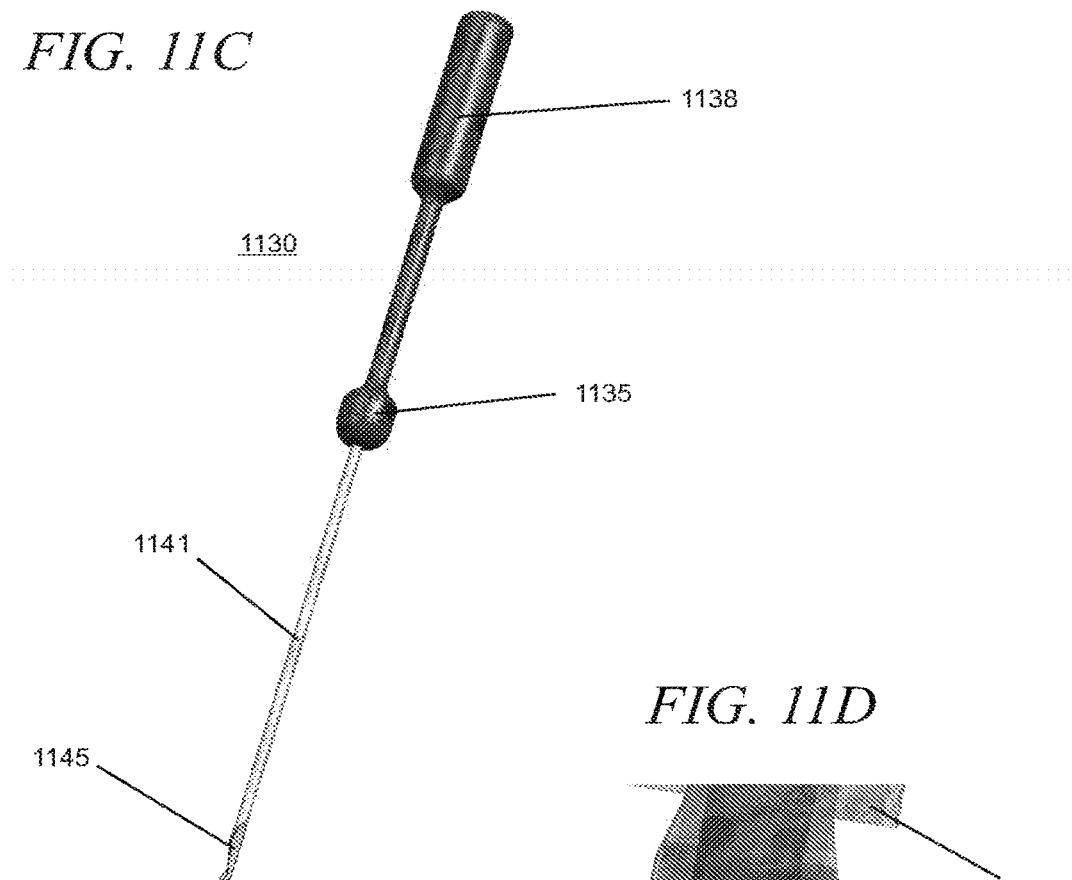
FIG. 11C is a pictorial view of a second illustrative interspinous knife.

FIG. 11C is a pictorial view of a second illustrative interspinous knife 1130 which functions to cut through tissue to enable the percutaneous access associated with the subsequent implantation of an interspinous spacer. Interspinous knife 1130 is usable to supplement interspinous knife 1102 (FIG. 11) or as an alternative to interspinous knife 1102.

Figure 11D:
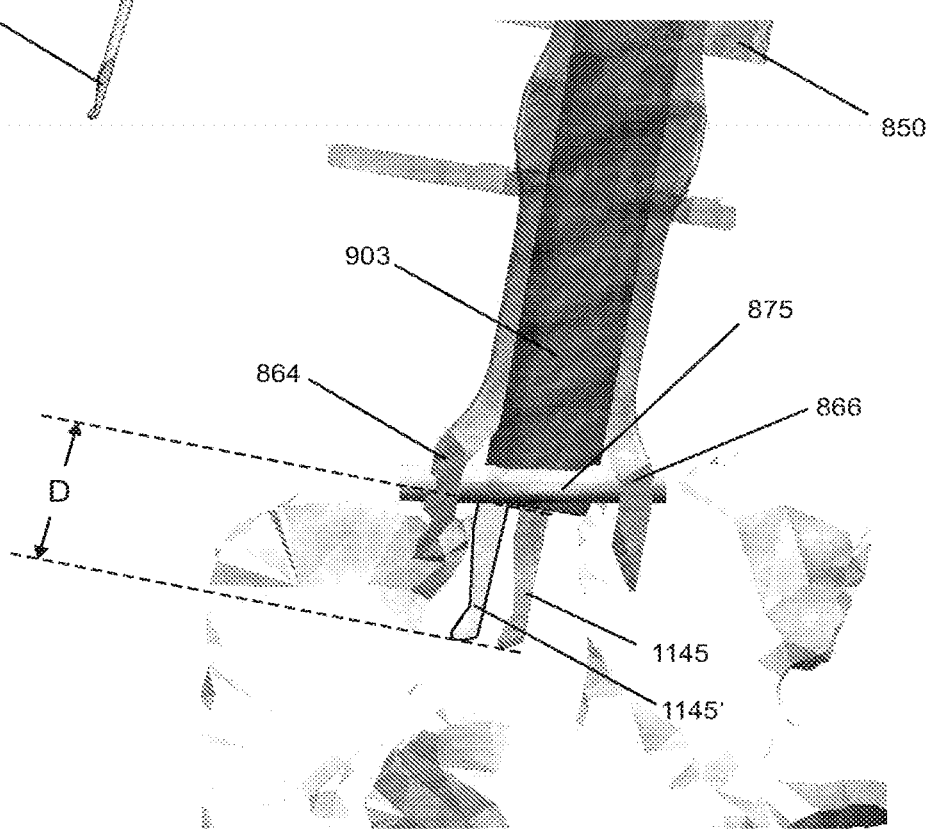
FIG. 11D is a detailed view of the distal end of the interspinous knife shown in FIG. 11C as inserted through a cannula and into the interspinous space.

Interspinous knife 1130 includes a semi-spherical depth stop 1135 that is integrally disposed in a handle 1138. Depth stop 1135 is sized and arranged to interface with the counterbore 918 (FIG. 9) in cannula 903 to thereby limit the cutting depth of interspinous knife 1130. Shaft 1141 is sized in length to place the cutting blade 1145 at a predetermined distance from the depth stop 1135. Shaft 1141 is sized so that cutting blade 1145 cuts to a nominal depth "D" of 15 mm, as indicated in FIG. 11D, from the anterior side of the supraspinous ligament 875. Alternatively, shaft 1141 is sized so that cutting blade 1145 cuts to a nominal depth of 20 mm.

Operation of the interspinous knife 1130 includes articulation of interspinous knife 1130 in cannula 903. In addition to a plunge-type cut that is depth controlled by the depth stop 1135, interspinous tissue is also cut by levering the handle 1138 so that the interspinous knife pivotally rotates about the semi-spherically shaped depth stop as a fulcrum. The distal end of the interspinous knife thus sweeps through an arc so that the cutting blade 1145 is movable through a range of positions including that indicated by 1145' in FIG. 11D.

Interspinous knife 1130 is preferably arranged as a disposable, single use tool in most applications of the invention. Cutting blade 1145 and shaft 1141 are constructed from stainless steel in most applications of the invention. The depth stop 1135 and handle 1138 of interspinous knife 1130 are generally formed from plastic such as a biocompatible plastic.

FIGS. 12, 12A, 12B and 12C show various views and features of a first illustrative interspinous reamer 1201 and its constituent components. Interspinous reamer 1201 is an optionally utilized tool in the tooling set described herein and functions to create a channel through which an interspinous spacer is inserted by removing bone and other tissue when required. Interspinous reamer 1201 is configured to remove both tough tissues including bone, as well as soft tissues. Interspinous reamer 1201 enables percutaneous access in combination, for example, with the mounting bracket 802 (FIG. 8) and cannula 903 (FIG. 9).

Interspinous reamer 1201 is configured to perform a tissue removal with a fixed diameter to thereby minimize damage to non-targeted tissue. Such diameter is preferably selected according to the size of the interspinous spacer being utilized. Interspinous reamer 1201 is further configured for controlled depth of penetration as described below.

Figure 12:
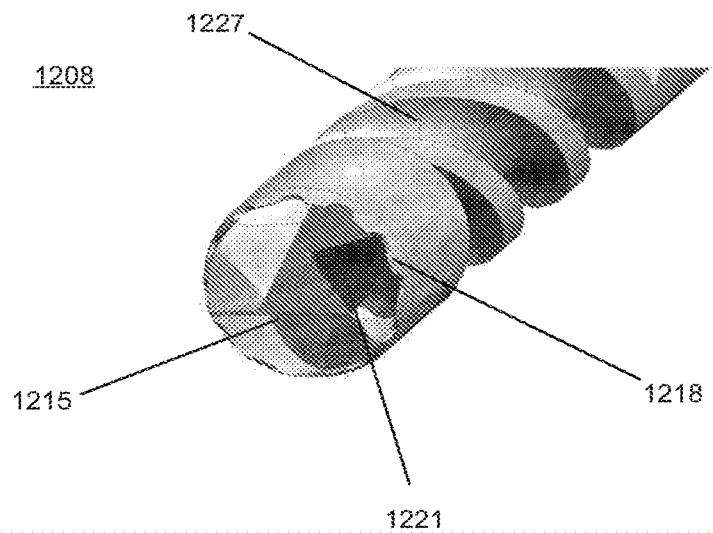
FIG. 12 is a pictorial view of a core cutting portion of a first illustrative interspinous reamer.
Figure 12A:
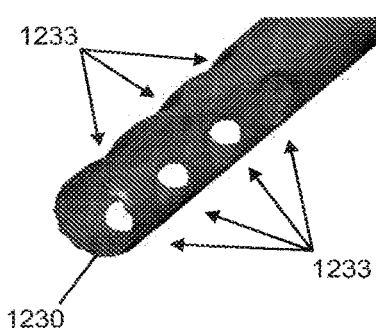
FIG. 12A is pictorial view of a hole cutting portion of the first illustrative interspinous reamer.
Figure 12B:
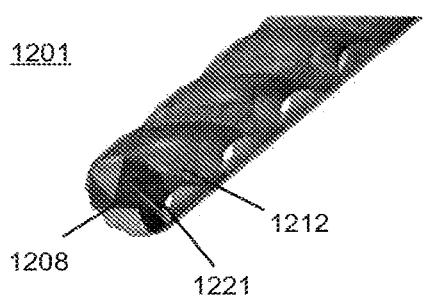
FIG. 12B is a pictorial view of the hole cutting and core cutting portions of the first illustrative interspinous reamer in operative engagement for performing a hole cutting process.
Figure 12C:
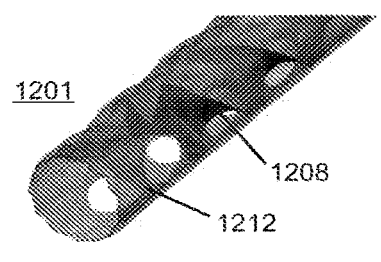
FIG. 12C is a pictorial view of the hole cutting and core cutting portions of the first illustrative interspinous reamer in operative engagement for performing a core cutting process.

Interspinous reamer 1201 uses a two-piece construction comprising a core cutter 1208, as shown in FIG. 12, and a hole cutter 1212, as shown in FIG. 12A. Core cutter 1208 is inserted into hole cutter 1212 to thereby form the interspinous reamer 1201 as shown in FIGS. 12B and 12C. FIG. 12B shows the core cutter 1208 being fully inserted into hole cutter 1212, while FIG. 12C shows the core cutter 1208 being partially inserted into the hole cutter 1212.

The interspinous reamer 1201 is generally operated in a two-step process. A hole cut is made into the target tissue using hole cutter 1212 which is followed by a core cut by the core cutter 1208 which evacuates the tissue from the tube of the hole cutter 1212.

Core cutter 1208 is comprised of a flat bottom drill bit having a sharpened tip 1215 and a forward serrated circumferential edge 1218. An evacuation port 1221 is disposed on the face of core cutter 1208. A spiral evacuation channel 1227 is disposed at the exit of the evacuation port 1221 for transporting removed tissue away from the working channel in the tissue when the interspinous reamer 1201 is coupled to a drill (such as a conventional bone drill, not shown) and rotated. Interspinous reamer 1201 is alternatively arranged to have an integrally incorporated drill or to be coupled to a drill in a conventional manner.

Hole cutter 1212 is arranged as an elongated tube having a sharpened distal end, for example, arranged as a forward serrated circumferential edge 1230, as shown in FIG. 12A A plurality of laterally disposed holes 1233 are arranged along the elongated tube of hole cutter 1212 to enable cleaning or evacuation of removed tissue into a cannula.

Core cutter 1208 and/or hole cutter 1212 are typically marked to allow for controlled penetration depth. Alternatively, core cutter 1208 and/or hole cutter 1212 can be constructed to include a mechanical lock or positive stop to physically limit or control penetration depth. For example, core cutter 1208 and/or hole cutter 1212 may include a lateral projection that positively engages with the counterbore 918 (FIG. 9B) in cannula 903 (FIG. 9) to function as a stop to limit penetration beyond a predetermined depth.

Interspinous reamer 1201 is typically arranged with radiopaque or conventional visible markings that are usable to assist with alignment, depth control, or mating with other discrete devices or tools. Alternatively, the markings may be arranged using ultrasonic, magnetic or other marker-types, for example, to avoid the need for fluoroscopy.

Interspinous reamer 1201 may be optionally arranged with an energy delivery functionality using an operatively coupled energy delivery unit (not shown) such as an RF (radio frequency) unit. In most applications, the energy is delivered through the distal ends of core cutter 1208 and/or hole cutter 1212 to assist with tissue penetration or coagulation. In an alternative arrangement, interspinous reamer 1201 is configured as an over-the-wire tool using a centrally disposed lumen in the core cutter 1208.

In most applications, interspinous reamer 1201 is beneficially arranged as a reusable, or multiple-use tool.

Figure 12D:
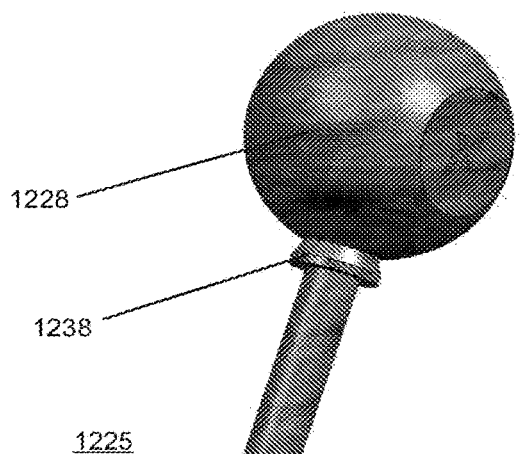
FIG. 12D is pictorial view of a second illustrative interspinous reamer.

FIG. 12D is a pictorial view of a second illustrative interspinous reamer 1225. As with the first illustrative interspinous reamer 1201 shown in FIGS. 12, 12A, 12B and 12C, interspinous reamer 1225 is an optionally utilized tool in the tooling set described herein and functions to create a channel through which an interspinous spacer is inserted by removing bone and other tissue when required. Interspinous reamer 1225 is configured to remove both tough tissues including bone, as well as soft tissues. Interspinous reamer 1225 is usable to supplement interspinous reamer 1201 (FIGS. 12 and 12A-C) or as an alternative to the interspinous reamer 1201.

Figure 12E:
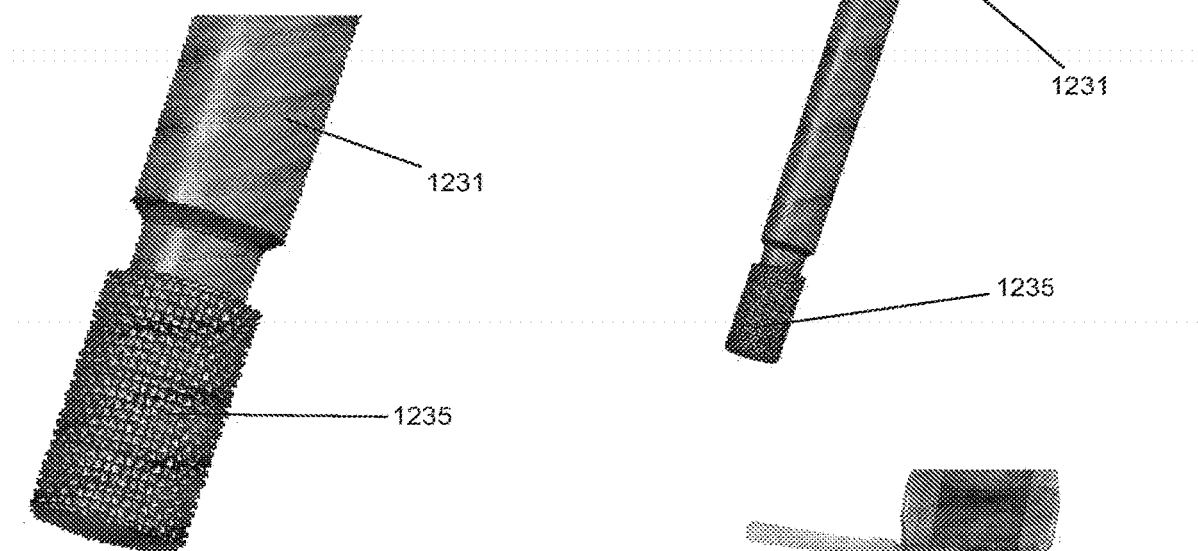
FIG. 12E is a detailed view of the distal end of the interspinous reamer shown in FIG. 12D.

Interspinous reamer 1225 includes a substantially spherically-shaped handle 1228 that is disposed at the proximal end of an elongated shaft 1231. At the shaft's distal end, a substantially cylindrically-shaped cutting element 1235 is disposed. Cutting element 1235 includes a plurality of radially outwardly projecting teeth disposed around the cylinder's surface in multiple rows as shown in the detailed view of FIG. 12E.

Figure 12F:
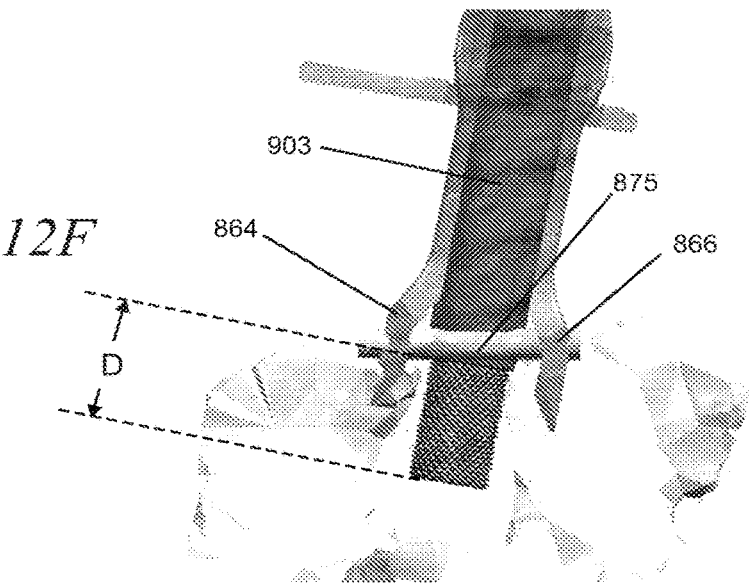
FIG. 12F is a detailed view of the distal end of the interspinous reamer shown in FIG. 12D as inserted through a cannula and into the interspinous space.

Interspinous reamer 1225 includes semi-disc-shaped depth stop 1238 that is disposed between the handle 1228 and the proximal end of the shaft 1231. Depth stop 1238 is sized and arranged to interface with the counterbore 918 (FIG. 9) in cannula 903 to thereby limit the cutting depth of interspinous reamer 1225. Shaft 1231 is sized in length to place the cutting element 1235 at a predetermined distance from the depth stop 1238. Shaft 1231 is sized so that cutting element 1235 cuts to a nominal depth "D" of 15 mm, as indicated in FIG. 12F, from the anterior side of the supraspinous ligament 875.

Interspinous reamer 1225 is typically arranged with radiopaque or conventional visible markings that are usable to assist with alignment, depth control, or mating with other discrete devices or tools. Alternatively, the markings may be arranged using ultrasonic, magnetic or other marker-types, for example, to avoid the need for fluoroscopy.

Interspinous reamer 1225 may be optionally arranged with an energy delivery functionality using an operatively coupled energy delivery unit (not shown) such as an RF (radio frequency) unit. In most applications, the energy is delivered through the distal end of the cutting element 1235 to assist with tissue penetration or coagulation. In an alternative arrangement, interspinous reamer 1225 is configured with a centrally disposed lumen and utilized as an over-the-wire tool.

In most applications, interspinous reamer 1225 is beneficially arranged as a reusable, or multiple-use tool. Handle 1228 is generally preferred to be formed from a polymeric material (i.e., plastic) such as a biocompatible plastic. Shaft 1231, depth stop 1238 and cutting element 1235 are typically formed from stainless steel.

Figure 13:
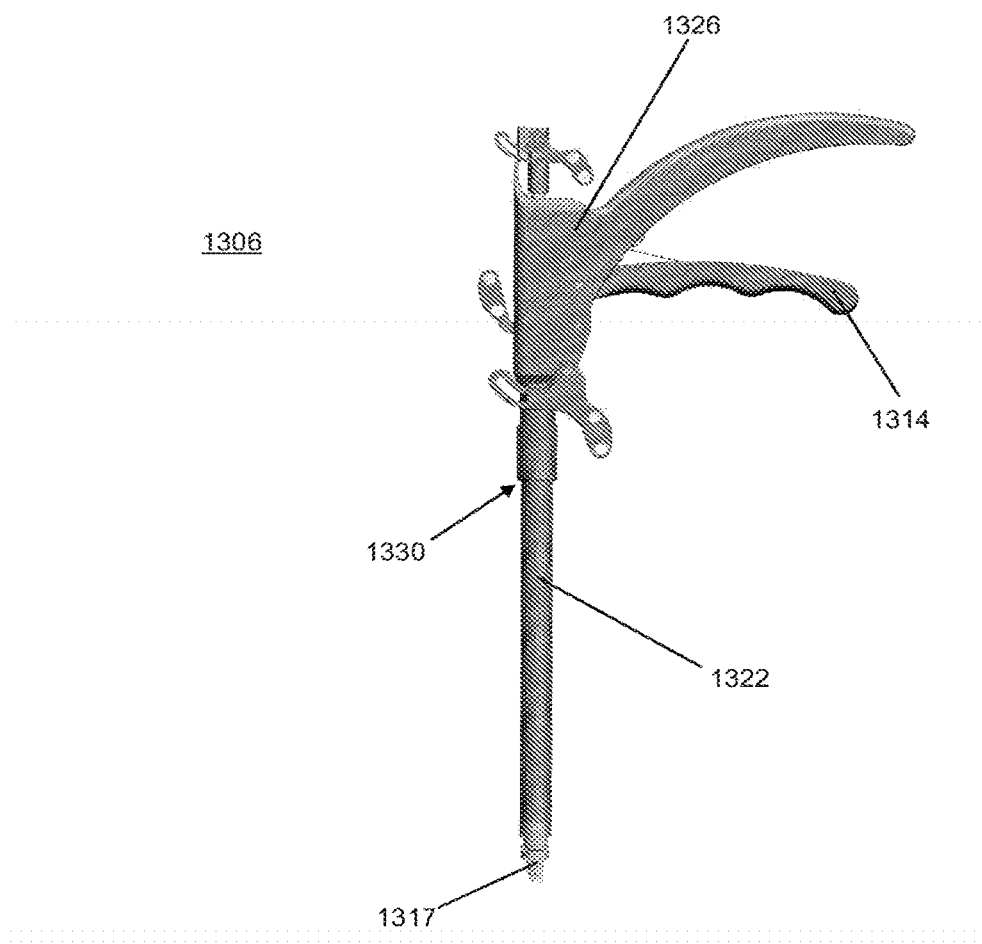
FIG. 13 is a pictorial view of a first illustrative interspinous gauge.
Figure 13A:
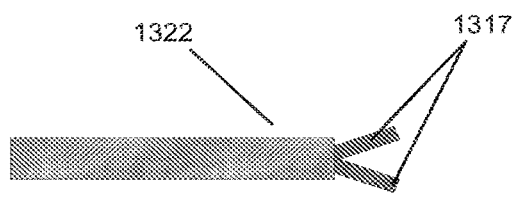
FIG. 13A is a detailed view of the distal end of an elongated tube in the interspinous gauge shown in FIG. 13.

FIG. 13 is a pictorial view of a first illustrative interspinous gauge 1306 which primarily functions to measure the distance between two adjacent spinous processes at an intended insertion point for the interspinous spacer. An operator manipulates control lever 1314 to deploy feelers 1317 from the distal end of an elongated barrel 1322 as shown in FIG. 13A. A gauge (not shown) on the handle 1326 provides a visual indication of the separation distance between the feelers 1317.

In the illustrative example of FIG. 13, a pair of feelers are shown in a deployed position. In other arrangements, other numbers of feelers are usable. In addition, in some applications it may be useful to employ an arrangement where only one feeler is movable while the others remain fixed in position.

The gauge may be selected, for example, from a mechanical type gauge using a needle or pointer on a scale, or an electronic type gauge with a numerical readout using an LCD (liquid crystal display) or LED (light emitting diode) array to indicate the distance between the feelers. In this latter case, the display typically is arranged to receive a signal from one or more sensors disposed on the feelers 1317. The sensor is generally selected from one of stain gauge, force-sensing resistor, potentiometer (e.g., linear potentiometer), magnetic sensor, rotational encoder (where the angle of rotation is correlated to distance) or optical sensor (e.g., phototransistor). Alternatively, in addition to being transmitted to the gauge, the sensor signal may be transmitted to a separate or standalone read-out device or display.

In typical applications, interspinous gauge 1306 is arranged with radiopaque or conventional visible markings that are usable to assist with alignment, depth control, or mating with other discrete devices or tools. Alternatively, the markings may be arranged using ultrasonic, magnetic or other marker-types, for example, to avoid the need for fluoroscopy. In another alternative arrangement, the markings include an indication of the interspinous spacer size or spacer catalog number to be used with the interspinous gauge 1306 (where interspinous spacer sizing is typically rounded, for example, to indicate an optimal or "best" size or catalog number). Instructions-for-use applicable to the interspinous gauge 1306 may also be included in the markings in such alternative arrangement.

Data provided to the operator on the gauge or via the markings is selected, for example, from one or more of position or orientation of the interspinous gauge 1306, deployment or distraction force being applied at the tool's distal end (e.g., through feelers 1317), deployment depth or level of the interspinous gauge 1306, or position and orientation of the interspinous spacer.

Interspinous gauge 1306 is preferably arranged as a reusable, multi-use tool in most applications. Interspinous gauge 1306 further includes a widened shoulder feature 1330 that is configured to engage with the counterbore 918 and flat 921 in cannula 903 (FIG. 9B) when the interspinous gauge 1306 is inserted through the lumen 906 of cannula 903. Such engagement between the shoulder feature and counterbore/flat thereby locates and aligns the interspinous gauge 1306 at the proper depth and orientation with respect to the cannula 903 and the spine.

Interspinous gauge 1306 is alternatively arranged to perform a variety of optional functions including:

1) Measure distraction force. Interspinous gauge 1306 includes force measuring components, such as sensors, that are disposed on the movable feelers 1317 in this alternative arrangement.

2) Distract spinous processes. In this alternative arrangement, the operator manipulates control lever 1314 to deploy feelers 1317 to perform the distraction function. In an optional configuration, the control lever 1314 or other structures in the interspinous gauge 1306 are equipped with distraction force-limiting or distraction distance-limiting features.

3) Determine "Go" or "No Go" status for interspinous spacer implantation. In this alternative arrangement, there are several scenarios, for example, that interspinous gauge 1306 may be used to address: a) evaluation of poor bone quality result in bone deformation instead of distraction; b) identification and/or treatment (e.g., smooth and/or remove) osteophytes that neighbor the point of contact, c) determination of inadequate spinous process thickness for interspinous spacer implantation, and d) other anatomical abnormalities that may be incompatible with the interspinous spacer or the tooling and/or procedures used to implant it.

The osteophytes are treatable using directed energy such as an RF energy source coupled to the feelers 1317, for example. Alternatively, mechanical abrasion may be applied through the feelers 1317. Feelers 1317 are generally provided with an abrasive surface and further configured to oscillate through operation of the control level 1314.

Figure 14F:
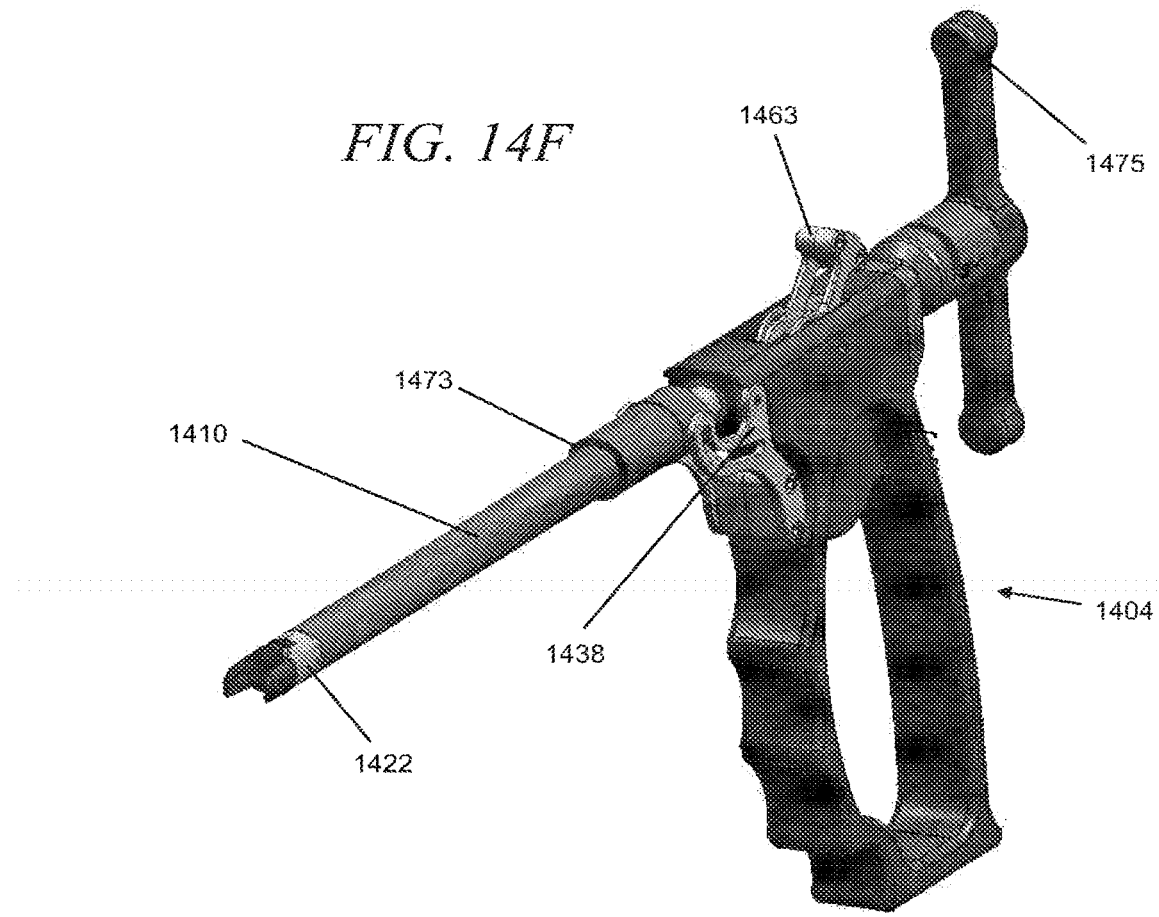
FIG. 14F is a pictorial view of a second illustrative insertion instrument.
Figure 14G:
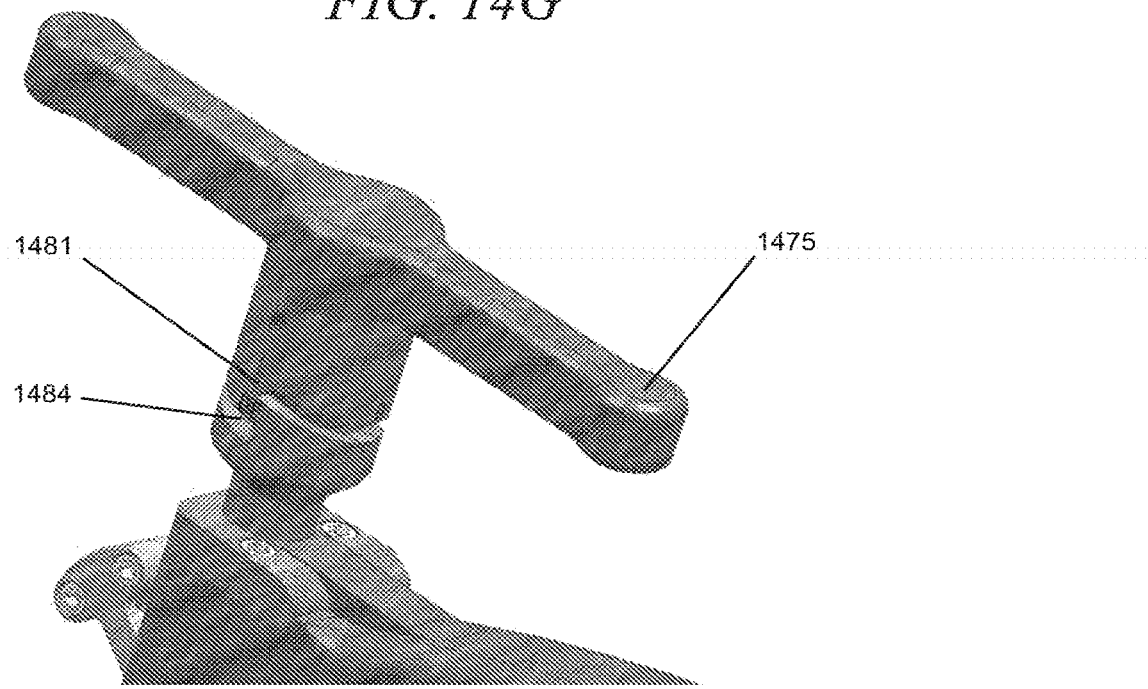
FIG. 14G is a detailed view of a load/deploy indicator disposed in the insertion instrument shown in FIG. 14F.

In some applications of the invention, interspinous gauge 1306 may also be arranged to include functionalities provided by the insertion instrument shown in FIG. 14 and described in the accompanying text.

Figure 13B:
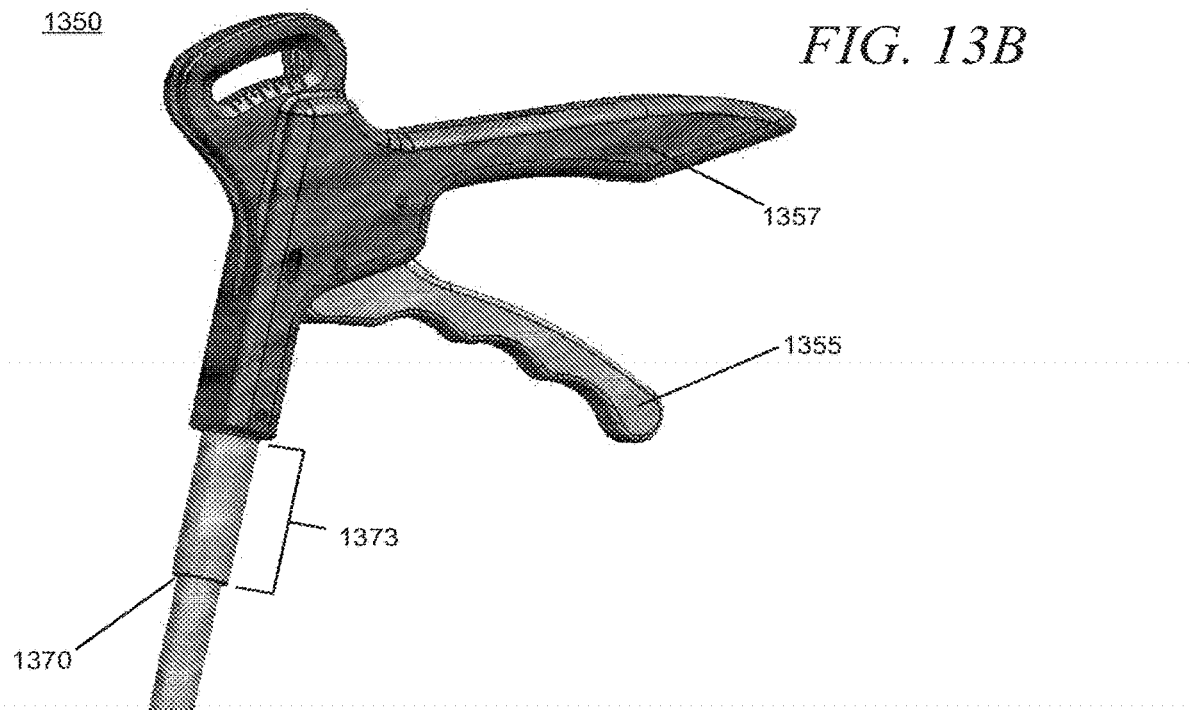
FIG. 13B is a pictorial view of a second illustrative interspinous gauge.

FIG. 13B is a pictorial view of a second illustrative interspinous gauge 1350 that is alternatively used in place of the interspinous gauge 1306 shown in FIGS. 13 and 13A. Interspinous gauge 1350 functions in a similar manner to the interspinous gauge 1306 in that it measures the distance between two adjacent spinous processes at an intended insertion point for the interspinous spacer.

Figure 13C:
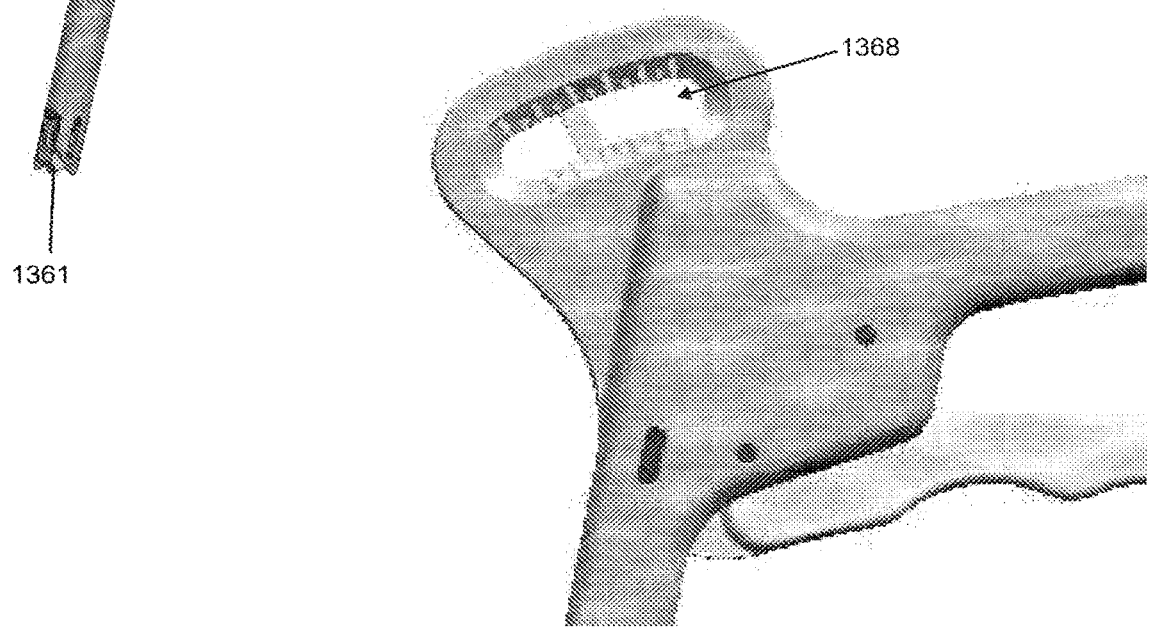
FIG. 13C is a detailed view of a sizing scale disposed in interspinous gauge shown in FIG. 13B.
Figure 13D:
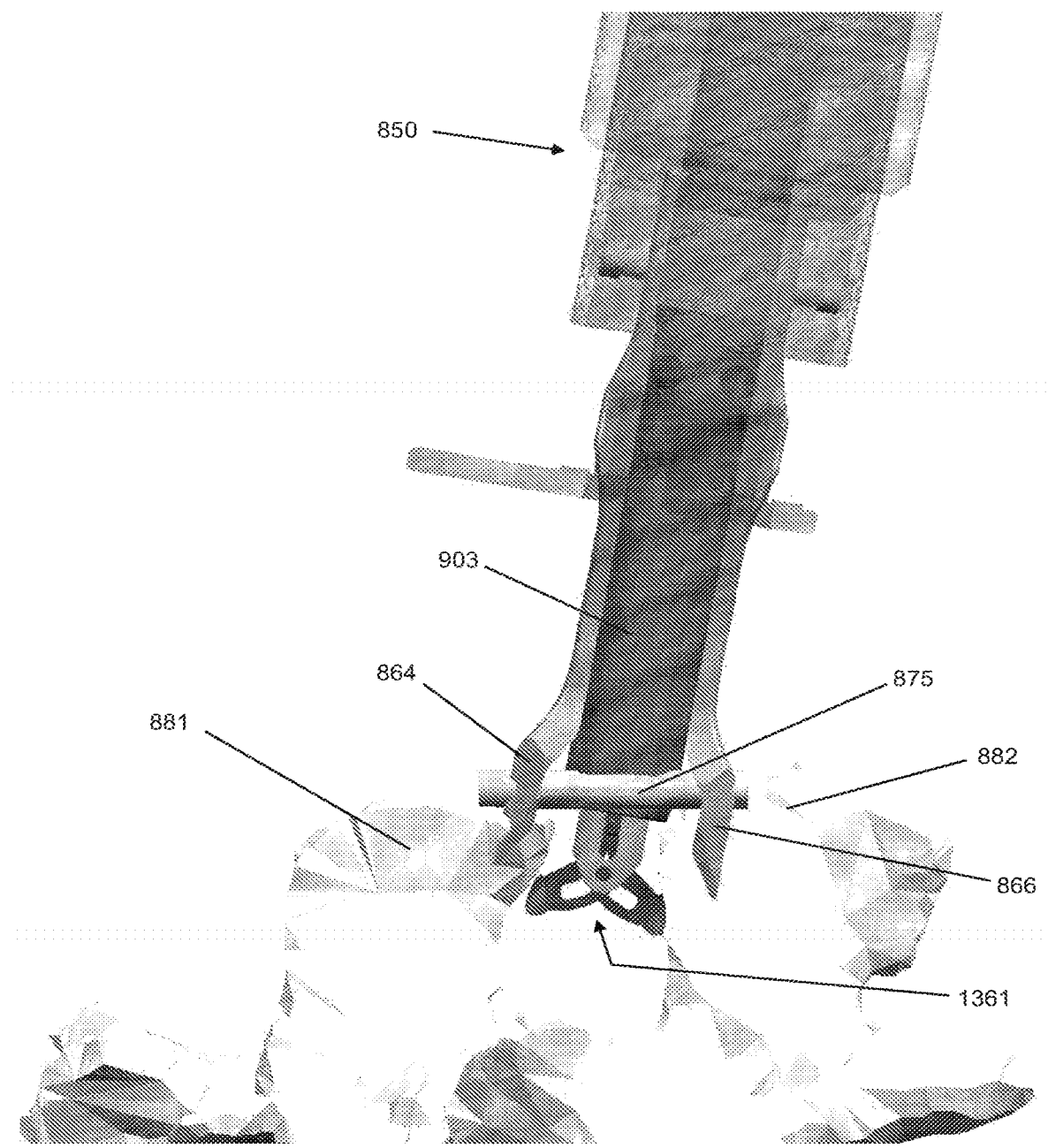
FIG. 13D is a view of the distal end of the interspinous gauge shown in FIG. 13B.

An operator manipulates control lever 1355 by squeezing towards handle 1357 to deploy feelers 1361 from the distal end of the elongated barrel 1365. A gauge 1368, as shown in the detailed view of FIG. 13C, provides a visual indication of the separation distance between the feelers 1361. FIG. 13D shows the feelers 1361 in the deployed position in the interspinous space formed between the superior spinous process 881 and inferior spinous process 882.

Interspinous gauge 1350 includes a widened shoulder feature 1370 that is configured to engage with the counterbore 918 and flat 921 in cannula 903 (FIG. 9) when the interspinous gauge 1350 is inserted through the lumen 906 of cannula 903. Such engagement between the shoulder feature and counterbore/flat thereby locates and aligns the interspinous gauge 1350 at the proper depth and orientation with respect to the cannula 903 and the spine.

Extending axially upward towards the handle 1357 from the widened shoulder 1370 is a marker area 1373 that is arranged to include one or more markers to assist with depth control of the interspinous gauge into the cannula 903. In typical applications, the markings are selected from radiopaque or conventional visible markings. Alternatively, the markings may be arranged using ultrasonic, magnetic or other marker-types, for example, to avoid the need for fluoroscopy.

Interspinous gauge 1350 is alternatively arranged to perform the optional functions discussed above in the description of interspinous gauge 1306. Interspinous gauge 1350 is preferably arranged as a reusable, multi-use tool in most applications.

FIG. 14 and 14A are pictorial views of an illustrative insertion instrument 1404. Insertion instrument 1404 functions to engage with, insert and deploy an interspinous spacer. Illustrative examples of interspinous spacers that are compatible with the insertion instrument 1404 are described in applicant's co-pending U.S. patent application Ser. No. 11/314,712, entitled "Systems and Methods for Posterior Dynamic Stabilization of the Spine" filed Dec. 20, 2005, the disclosure of which is incorporated by reference herein. In the illustrative example shown in FIGS. 14 and 14A, the depicted interspinous spacer uses a deployment mechanism which is activated by translation and/or rotation.

Insertion instrument 1404 uses the working channel that is preferably created by use of tools shown in FIGS. 3-13 and described above including, for example, target needle 305, K-wire 402, dilators 605 and 705, mounting bracket 802, cannula 903, stabilizing arm 1012, interspinous knife 1102, optionally utilized interspinous reamer 1201, and interspinous gauge 1306. Insertion instrument 1404 is typically inserted through cannula 903 (FIG. 9) in mounting bracket 802 which provides alignment and depth control and, in particular, precise control of the optimal axial, sagittal and coronal implant positioning.

Insertion instrument 1404 includes an elongated barrel 1410 that extends from a handle 1416 to which deployment lever 1419 is pivotally disposed. Deployment lever 1419 is operatively coupled to extend and/or rotate an inner shaft 1422 that is disposed within barrel 1410 and extends just beyond the distal end of barrel 1410. In this illustrative example, when the insertion instrument 1404 is engaged to an interspinous spacer, translation, and/or rotation of the inner shaft 1422 expands the movably extendable elements of the interspinous spacer to thereby place it into a deployed condition. Reversal of the translation or rotation places the interspinous spacer back into a collapsed, un-deployed condition through the use of retraction lever 1463.

The deployment lever is alternatively arranged as a T-handle 1475 that is disposed at the proximal end of insertion instrument 1404 and coupled to inner shaft 1422 as shown in FIG. 14F. In this alternative arrangement, rotation of the T-handle 1475 expands the interspinous spacer to thereby deploy it. In this alternative example, the T-handle 1475 rotates in an indexed fashion through use of a laterally projecting pin 1481 from the T-handle axle that travels through a spiral track 1484 to thereby create several discrete positions corresponding to varying deployment positions for the interspinous spacer. These positions "L", "D", and "DE" are visually indicated on the insertion instrument 1404 corresponding to interspinous spacer states Load, Deployed, and Deployed Extended which are described below in the text accompanying FIGS. 31A-F.

It is emphasized that other interspinous spacer types and designs (i.e., those that use other deployment mechanisms than that described above) are also usable with insertion instrument 1404. In addition, the interspinous spacer is optionally pre-attached (typically by the manufacturer) to the insertion instrument 1404.

In most applications, insertion instrument 1404 is beneficially arranged as a reusable, or multiple-use tool. In some applications of the invention, it may also be desirable to combine the functionalities provided by insertion instrument 1404 with those provided by interspinous gauge 1306 (FIG. 13) into a single instrumentality or tool.

An outer clamping mechanism 1426 is also disposed at the distal end of barrel 1410 and extends outwardly. As shown in FIG. 14B, outer clamping mechanism 1426 includes an extended tang 1428 and a non-extended tang 1430. Outer clamping mechanism 1426 is operatively coupled to a first operating lever 1435 as shown in FIG. 14. Operation of the first operating lever 1435 causes the outer clamping mechanism 1426 to lock to interspinous spacer 1440 and, in particular, by the engagement of lateral ribs 1442 on the proximal end of interspinous spacer 1440 into corresponding slots 1450 in extended tang 1428 and non-extended tang 1430, as shown in FIG. 14C.

A second operating lever 1438 is operatively coupled to the distal end of inner shaft 1422 to which an inner clamping mechanism 1455 is disposed. Inner clamping mechanism 1455 is comprised of opposing jaws (not shown) that are arranged to grasp a mating projection 1458 extending normally rearward from the proximal end of the interspinous spacer 1440. Translation and/or rotation of mating projection 1458 operates the deployment mechanism of the interspinous spacer 1440. Operation of the second operating lever 1438 causes the inner clamping mechanism to lock to projection 1458 on interspinous spacer 1440.

First and second operating levers 1435 and 1438 are each arranged to include both locking and unlocking functionality through forward and reverse operation of the levers, respectively. Accordingly, insertion instrument 1404 is configured to both engage and disengage interspinous spacer 1440 through operation of the operating levers 1435 and 1438 by the operator. Insertion instrument 1404 is further preferably configured to re-engage with interspinous spacer 1440, for example, for further distraction if required or to remove the interspinous spacer.

In typical applications, insertion instrument 1404 includes a variety of markings, for example, to indicate various status conditions of the tool and the associated interspinous spacer 1440. In an alternative arrangement, the markings are selected as conventional visible markings or may be radiopaque. Insertion instrument 1404 may also be optionally arranged with one or more markers selected, for example, from ultrasonic, magnetic markers or other marker types to advantageously avoid the need for fluoroscopy.

A visual scale 1470 as shown in FIG. 14D is provided as one example of markings to indicate the amount of interspinous spacer deployment and/or the engagement condition (i.e., locked, unlocked, degree of lock etc.) of the interspinous spacer 1440 to the insertion instrument 1404. Visual scale 1470 thus provides quantitative feedback to the operator including "Go" or No Go" deployment status. FIG. 14E illustrates the deployment positions of the interspinous spacer 1440 indicated by the visual scale 1470.

A zero depth indicator is provided by a widened shoulder feature 1473 on insertion instrument 1404 that is configured to engage with the counterbore 918 and flat 921 in cannula 903 (FIG. 9) when the insertion instrument 1404 is inserted through the lumen 906 of cannula 903. Such engagement between the shoulder feature and counterbore/flat thereby locates and aligns the insertion instrument 1404 at the proper depth and orientation with respect to the cannula 903 and the spine.

Insertion instrument 1404 may be optionally arranged with an energy delivery functionality using an operatively coupled energy delivery unit (not shown) such as an RF (radio frequency) unit. In most applications, the energy is delivered through the distal end of barrel 1426 (e.g., through clamping outer mechanism 1426, the distal end of inner shaft 1422, or inner clamping mechanism 1455) or via the coupled interspinous spacer 1440 to assist with tissue penetration or coagulation.

Figure 15:
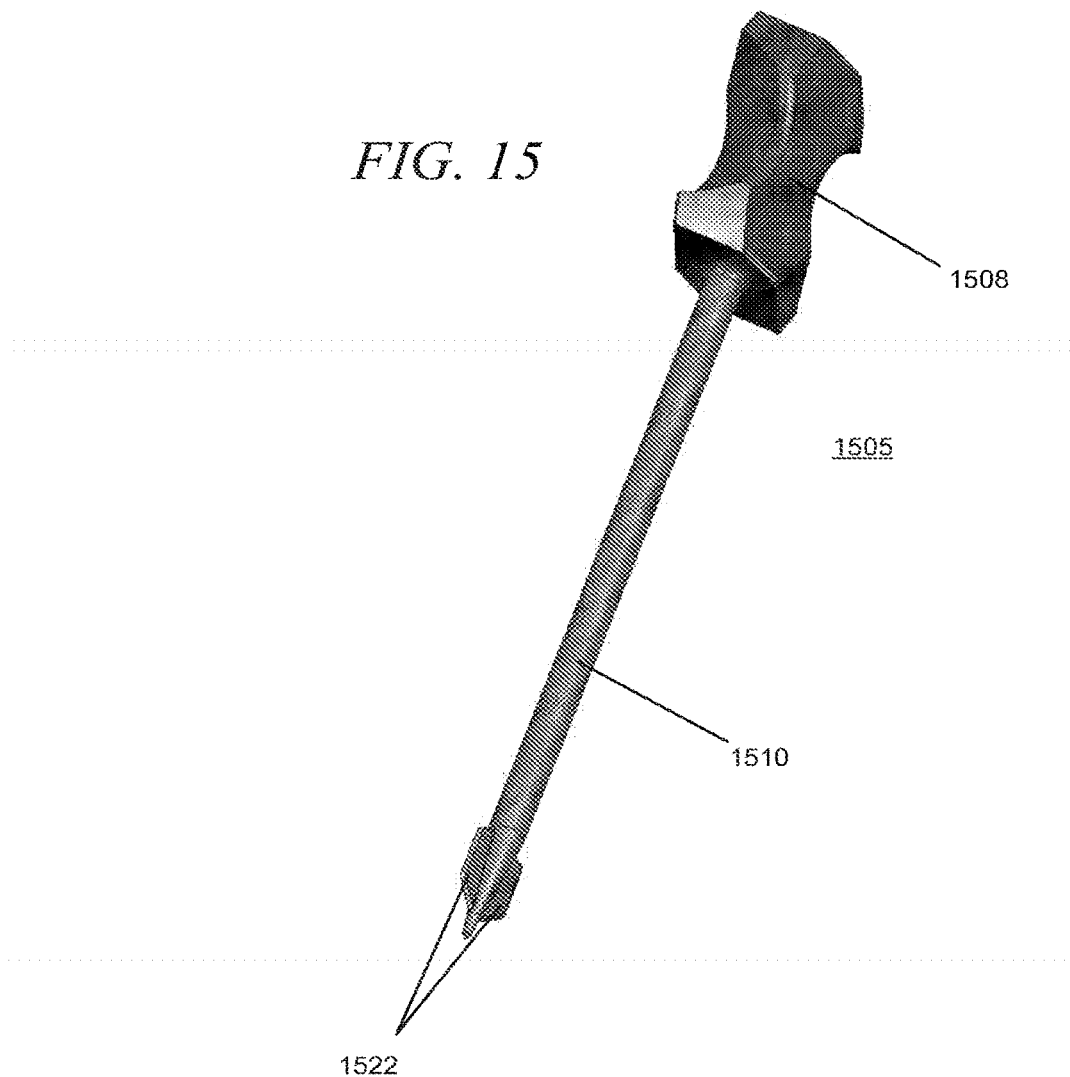
FIG. 15 is a pictorial view of an illustrative ligament splitter.

FIG. 15 is a pictorial view of an illustrative ligament splitter 1505 that functions to split or part ligaments, such as the supraspinous ligament, or other tissues. Ligament splitter 1505 is intended for use in the beginning steps of interspinous spacer implantation or during subsequent steps, i.e., one or more times, as required. The ligament is typically separated with ligament splitter 1505 along ligamentous strands to minimize tearing, trauma, or other damage to the ligament. Such separation eases insertion of other devices, instrumentalities or tools (e.g., dilators 605 and 705 in FIGS. 6 and 7, and cannula 903 in FIG. 9). Separation is generally performed along a posterior, mid-line approach through the supraspinous ligament, although alternative approaches are also usable to thereby atraumatically part tissue.

Ligament splitter 1505 is beneficially arranged as a reusable, or multiple-use tool in most applications of the invention.

Figure 15A:
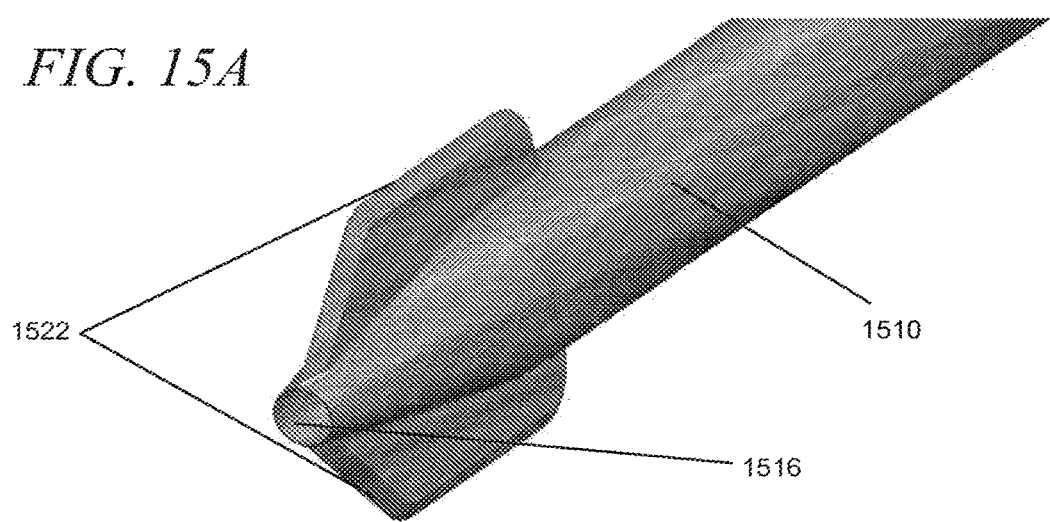
FIG. 15A is a detailed view of the distal end of the ligament splitter shown in FIG. 15.

Ligament splitter 1505 is constructed from an elongated tube 1510 with an internally disposed lumen 1516 through which a guidewire such as K-wire 402 (FIG. 4) is passed. The proximal end includes a handle 1508 that is typically formed from a polymeric material (i.e., plastic) such as a biocompatible plastic. The distal end of ligament splitter 1505, as shown in FIG. 15A, includes cutting blades 1522, which in this illustrative example, are arranged as a pair of blades. In alternative arrangements, other blade counts may be used as required by a particular application of the invention. Cuttings blades 1522 are illustratively arranged with forward cutting surfaces and side cutting surfaces.

The distal end of ligament splitter 1505 is generally tapered, and in one preferred arrangement, the taper length is nominally 0.550 inches with a nominal taper angle of 12 degrees.

The handle 1508 at the proximal end of ligament splitter 1505 is optionally utilized. Such handle may be used to assist with the insertion of ligament splitter 1505 in some applications. When thus equipped, the lumen 1516 is arranged to pass through the handle 1508. The optional handle is further arranged to include one or more markings to indicate an orientation of the handle and/or ligament splitter 1505. Such markings are typically visible markings, but may also be configured as radiopaque in some applications.

Ligament splitter 1505 may be optionally arranged with an energy delivery functionality using an operatively coupled energy delivery unit (not shown) such as an RF (radio frequency) unit. In most applications, the energy is delivered through the cutting blades 1522.

Ligament splitter 1505 is arranged, in most typical applications, to include a variety of markings, for example, to indicate orientation and/or depth of the ligament splitter 1505 when in use. In an alternative arrangement, the markings are selected as radiopaque markers to provide one or more depth markers to thereby assist with the splitting of the ligament. Ligament splitter 1505 may also be optionally arranged with one or more markers selected, for example, from ultrasonic, magnetic markers or other marker types to advantageously avoid the need for fluoroscopy.

In an alternative arrangement that may be particularly useful in some applications of the invention, two or more ligament splitters are utilized. Such ligament splitters share the above-described features and benefits of ligament splitter 1505, but are sized sequentially larger (i.e., in diameter and/or length).

Referring now to FIGS. 16-20, several illustrations are presented which show various anatomical locations having relevance to the present tooling and an inventive procedure for implanting an interspinous spacer such as interspinous spacer 1440 in FIG. 14C.

The procedure is generally intended to be performed in an operating room with the use of fluoroscopy. However, in an alternative arrangement, ultrasound may be used instead of fluoroscopy to thereby allow the procedure to be performed in a doctor's or clinician's office.

Figure 16:
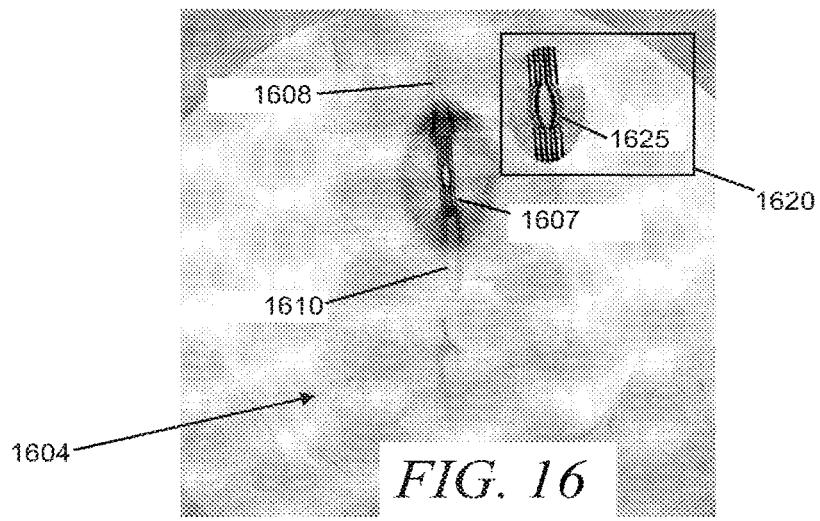
FIGS. 16, 17, 18, 19 and 20 are illustrations which show various anatomical locations having relevance to the present tooling and procedure for implanting an interspinous spacer.
Figure 17:
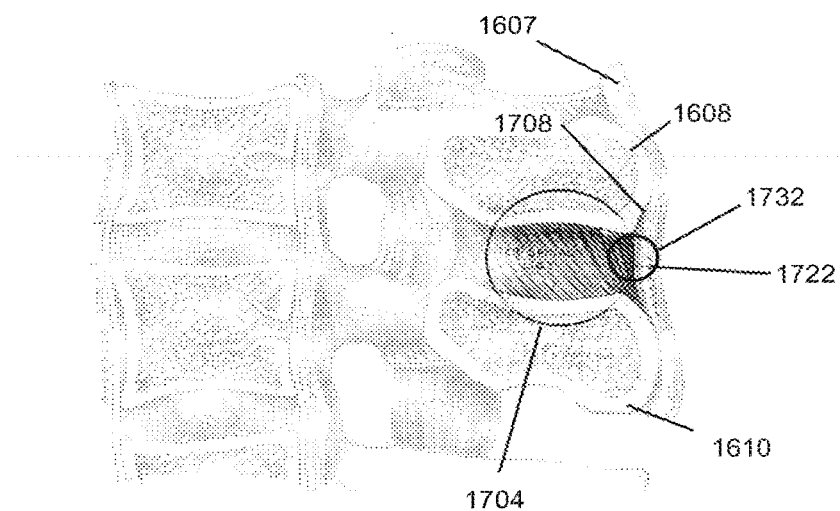

FIG. 16 provides an anteroposterior (AP) view of a lumbar spine 1604 and FIG. 17 provides a side view. Shown are the supraspinous ligament 1607 (with ligamentous strands), superior spinous process 1608 and inferior spinous process 1610. The inset illustration—indicated by reference numeral 1620—shows a dilated portion 1625 of supraspinous ligament 1607. FIG. 17 also shows approach angle 1722 and zero point 1732.

Figure 18:
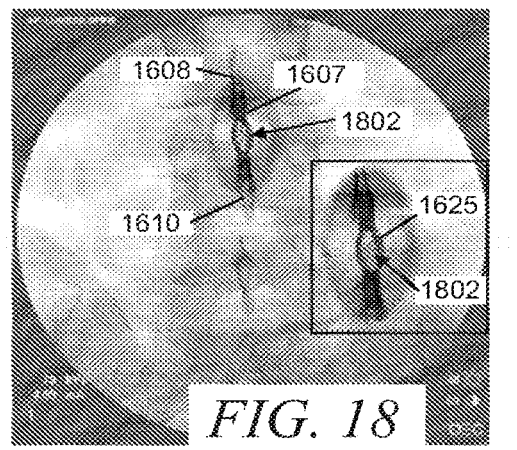
Figure 19:
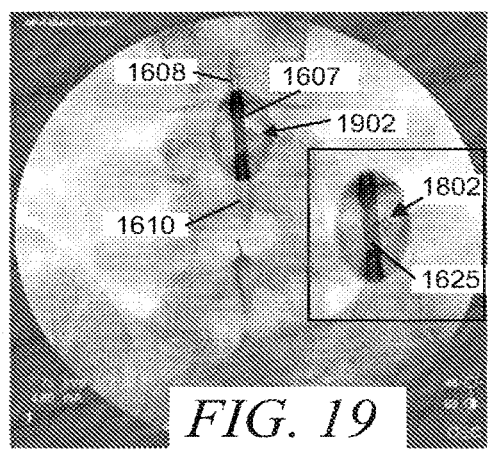
Figure 20:
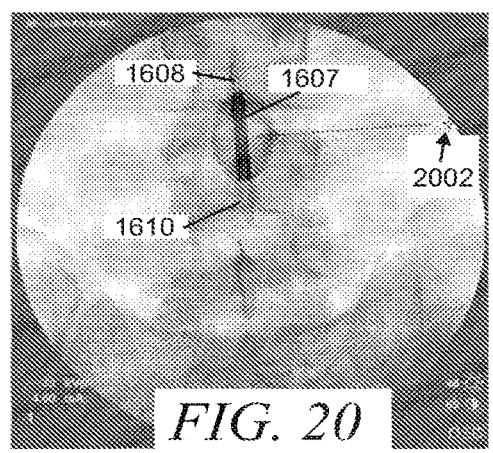

A posterior mid-line approach (designated by reference numeral 1802) through the supraspinous ligament 1607, as illustrated in the AP view of FIG. 18, is generally preferred. However, non-mid-line approaches are also usable. For example, an approach 1902 just lateral of the supraspinous ligament is shown in the AP view of FIG. 19. A pure lateral approach 2002 is shown in the AP view of FIG. 20. In such alternative non-mid-line approaches, the same tooling is often utilizable as with the mid-line approach. In some cases, however, similar tooling is utilized with modifications to make the tooling longer, if necessary. The interspinous spacer implantation is alternatively performed using percutaneous or minimally invasive surgical approaches, or using traditional open surgery.

The procedure for implantation of the interspinous spacer preferably includes the creation of a working channel through dilation of tissue (including ligaments) using the tooling system shown in FIGS. 3 to 15 and described in the accompanying text including, for example, target needle 305, K-wire 402, dilators 605 and 705, mounting bracket 802, cannula 903, stabilizing arm 1012, interspinous knife 1102, optionally utilized interspinous reamer 1201, and ligament splitter 1505. The procedure overall is relatively rapid and enables a shortened recovery period. Advantageously, the procedure is completely reversible at each step.

The interspinous spacer 1440 is preferably deployed into an un-distracted working space 1704 (FIG. 17) adjacent to the anterior wall 1708 of supraspinous ligament 1607. However, interspinous spacer 1440 is alternatively deployed in a pre-distracted, or partially distracted space.

Figure 21:
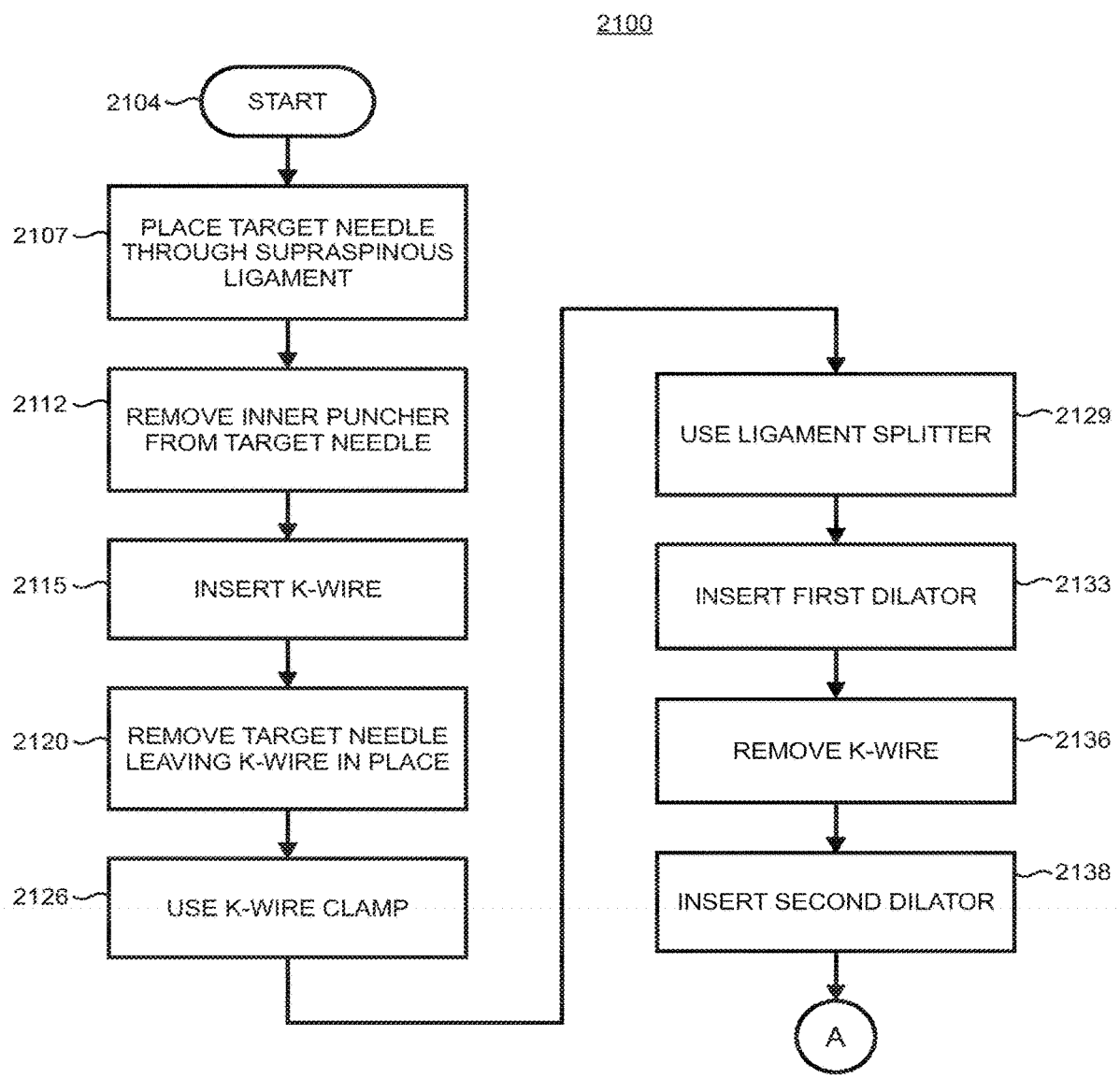
FIGS. 21 and 21A comprise a flowchart of an illustrative procedure for implanting an interspinous spacer using the tooling shown in FIGS. 3 to 15.
Figure 21A:
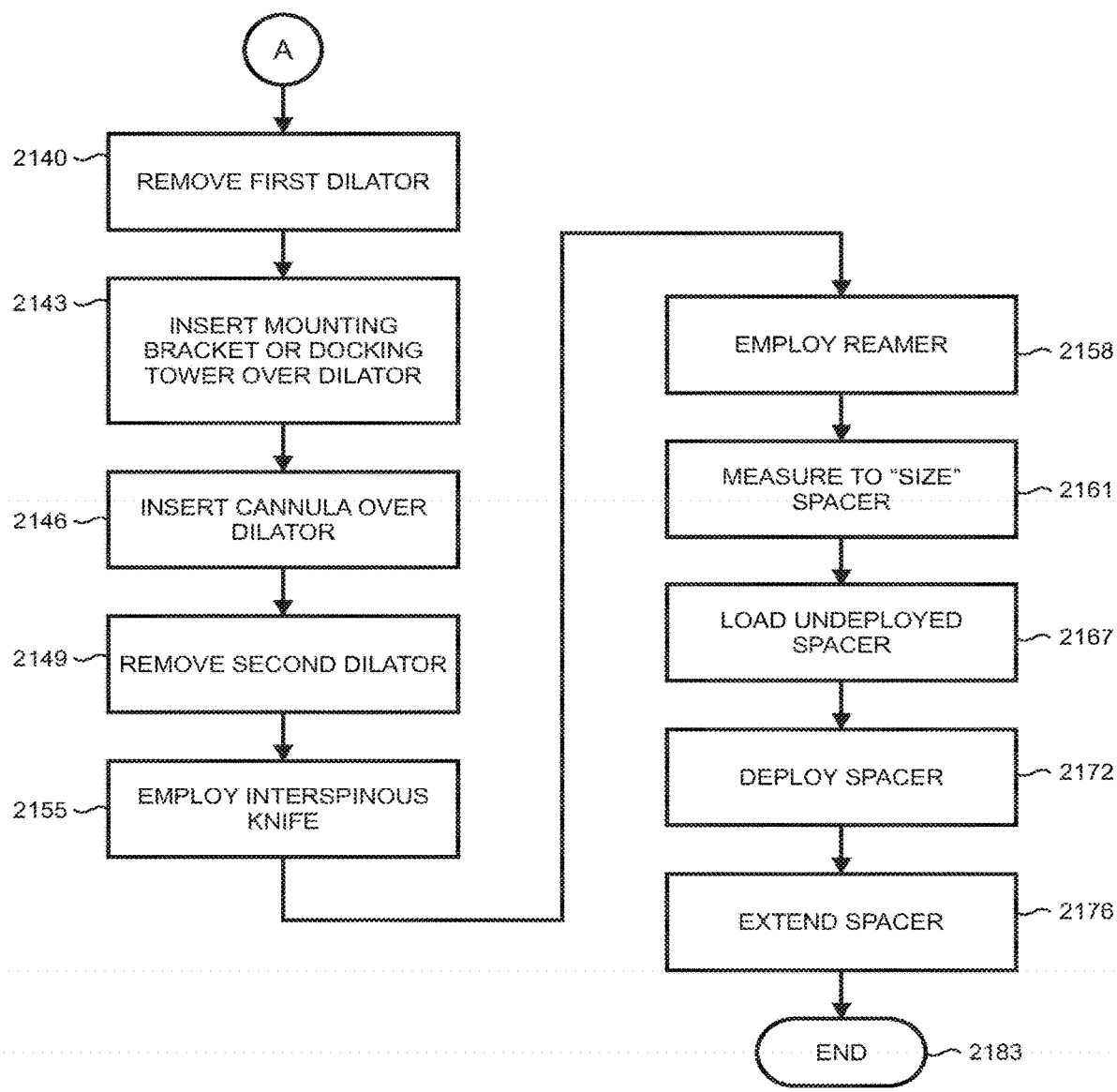

FIGS. 21 and 21A show a flowchart of an illustrative procedure for implanting an interspinous spacer using the tooling shown in FIGS. 3 to 15. The description of the flowchart that follows makes reference to a number of illustrations shown in FIGS. 22 to 33 below. The illustrative procedure starts at block 2104.

Figure 22:
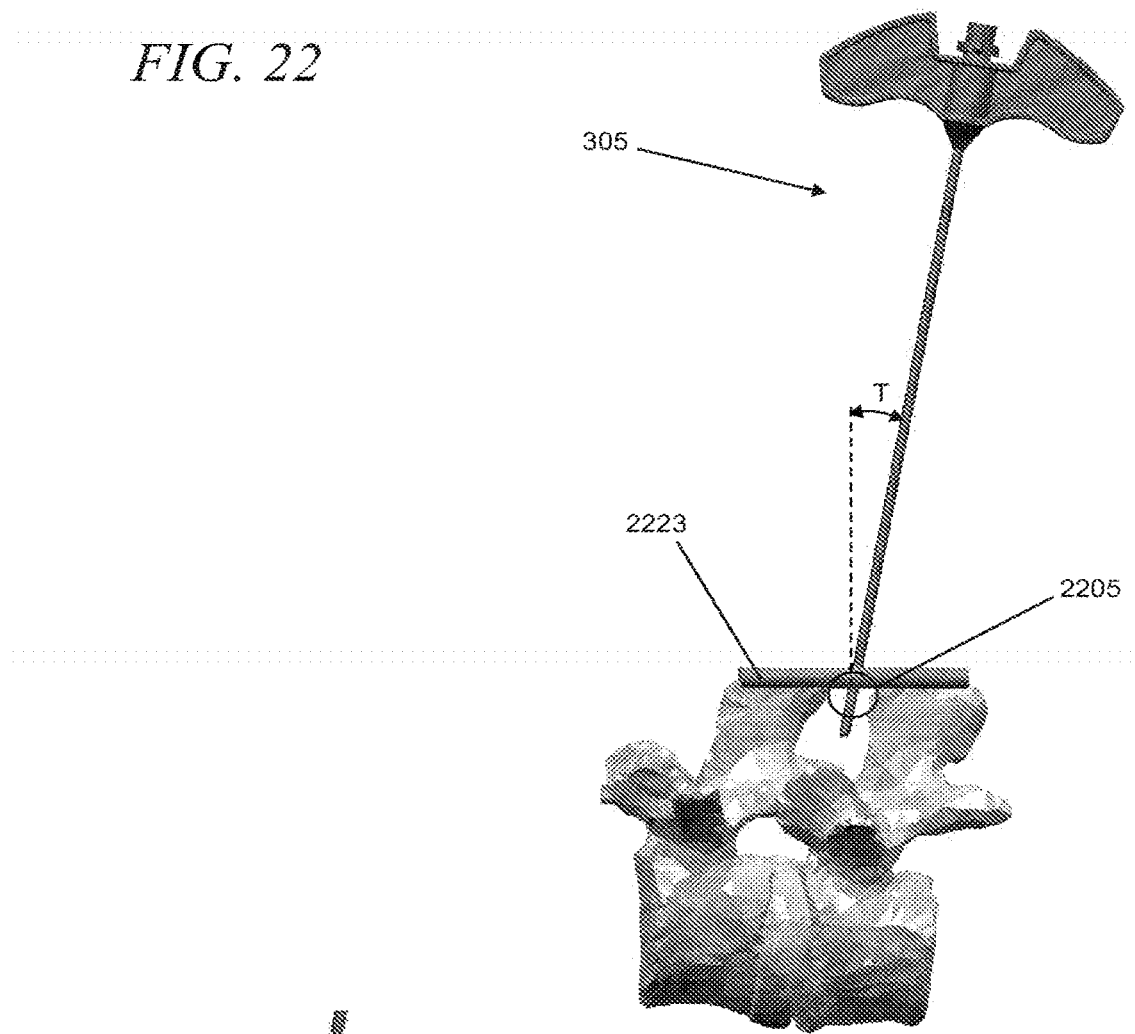
FIG. 22 is a pictorial view of the illustrative target needle of FIGS. 3 and 3A as inserted through the supraspinous ligament.
Figure 22A:
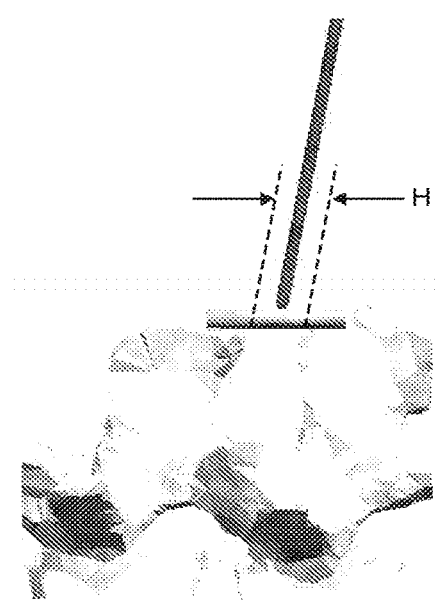
FIG. 22A is a detailed view of the distal end of the target needle showing its approximately centralized position between the superior and inferior spinous processes.

Blocks 2107 and 2112 include Step 1 in the illustrative procedure. As indicated in block 2107, the target needle 305 (FIG. 3) is inserted through the supraspinous ligament 2223 (FIG. 22) to an appropriate point beyond its anterior side as confirmed through the use of fluoroscopy. As indicated in block 2112, the inner puncher 321 (FIG. 3) is then removed. The result is illustrated in FIG. 22 where the target needle 305 is shown inserted to an appropriate depth past the zero point 2205 (which is defined as the anterior side of the supraspinous ligament 2223). FIG. 22 also shows that the inner puncher 321 is removed from the target needle 305.

Block 2115 in FIG. 21 includes Step 2 in the illustrative procedure in which the K-wire 402 (FIG. 4) is inserted through the hollow needle portion 327 of target needle 305. FIG. 23 shows the hollow needle portion 327 in cross section and the K-wire 402 inserted therethrough to zero point 2205. As shown in FIGS. 23A and 23B, K-wire 402 is inserted to an appropriate depth by aligning the groove 406 to the top of the wing 325. Alternatively, the appropriate depth may be determined using fluoroscopy.

As indicated by block 2120 in FIG. 21, the target needle 305 is next removed, leaving the K-wire 402 in place.

Block 2126 in FIG. 21 shows an optional Step 3A in the illustrative procedure. K-wire clamp 505 (FIG. 5) is optionally utilized to prevent inadvertent advancement of K-wire 402 while an operator determines the proper orientation of other devices that are installed over the K-wire 402. Once such determination is completed, K-wire clamp 505 is typically removed.

Figure 24:
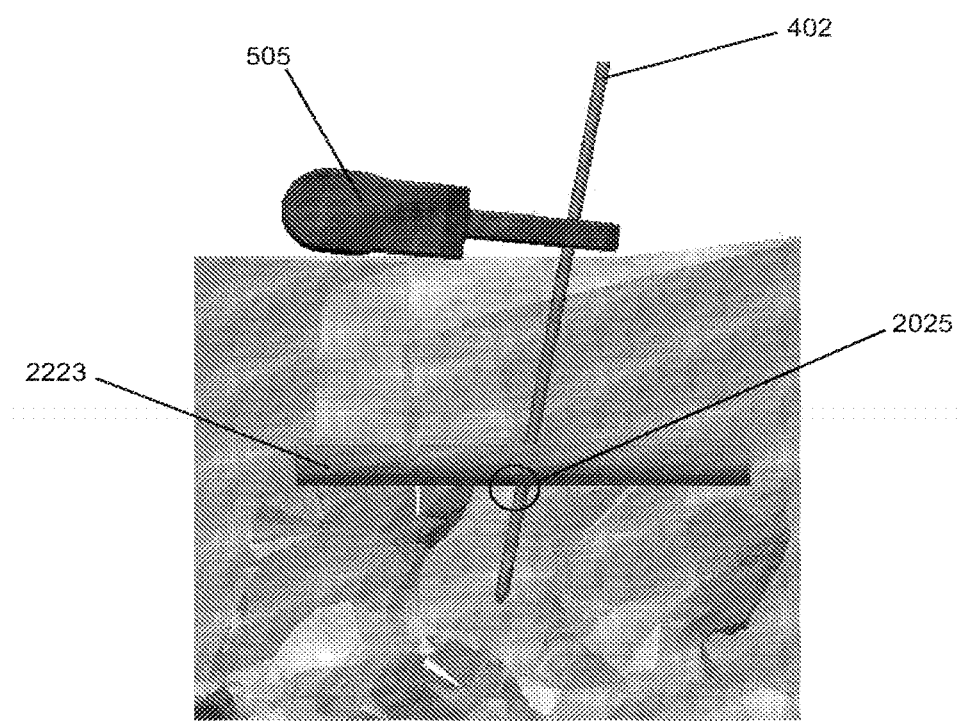
FIG. 24 is a pictorial view of an optional use of the illustrative K-wire clamp of FIG. 5 during positioning of the K-wire.

FIG. 24 shows K-wire clamp 505 being utilized on K-wire 402 to hold it at the zero point 2025 in supraspinous ligament 2223 (FIG. 22).

Block 2129 in FIG. 21 shows an optional Step 3B in the illustrative procedure where the ligament splitter 1505 (FIG. 15) is inserted over the K-wire 402 (FIG. 4). Ligament splitter 1505 is optionally utilized to split supraspinous ligament 2223 (FIG. 22) and/or other tissue (e.g., nonligament tissue when utilizing a lateral approach). Typically, the blades 1522 of ligament splitter 1505 are aligned with the superior and inferior spinous processes 1608 and 1610 (FIG. 16) to thereby be parallel with the ligamentous strands of the supraspinous ligament 2223 (FIG. 22). A minimal amount of axial force is then imparted through ligament splitter 1505 to thereby part (i.e., split) the supraspinous ligament 2223. Subsequent tools in the tooling system of the present invention may then be placed through such parted tissue.

In alternative arrangements, ligament splitter 1505 is utilized in non-posterior mid-line approaches such as those encountered with lateral procedures and open surgeries (i.e., non-minimally-invasive surgeries). In addition, it is noted that ligament splitter 1505 may be beneficially used repeatedly, as required, in subsequent steps in the illustrative procedure described herein, or used solely in procedural steps that occur after the initial penetration of the supraspinous ligament.

Block 2133 in FIG. 21 indicates Step 4 in the illustrative procedure in which dilation of tissue is started. Here, the first illustrative dilator 605 (FIG. 6) is passed over the K-wire 402 to an appropriate depth which is, typically, determined using fluoroscopy so that the tapered end portion 621 of dilator 605 is located just past the anterior side of the supraspinous ligament 2223 (FIG. 22). In some applications of the invention, it may be helpful for the operator to rotate or rock the dilator 605 using a back and forth motion as it is being inserted through the tissue. Markers, such as circumferential groove 611 and longitudinal groove 615, described above, generally provide alignment and/or proper depth control of dilator 605. In addition, the spinous process channel 626 on dilator 605, which is also described above, helps to maintain a desired mid-line positioning of dilator 605 with respect to the supraspinous ligament 2223.

In alternative arrangements, dilator 605 is usable to distract the spinous processes (e.g., spinous processes 1608 and 1610 in FIG. 16). Either the spinous process channel 626 or tapered end portion 621 may be used in such cases.

Figure 25:
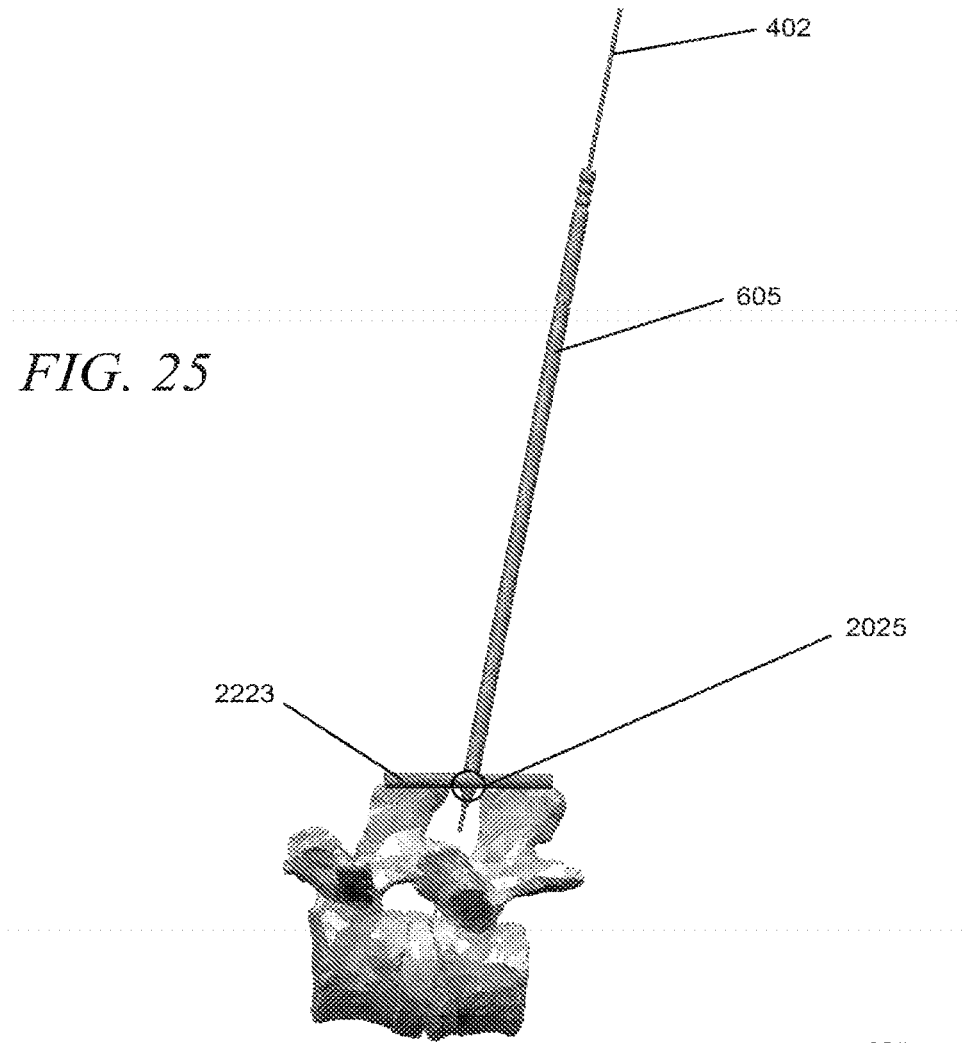
FIG. 25 is a pictorial view of the first illustrative dilator shown in FIG. 6 as inserted through the supraspinous ligament.
Figure 25A:
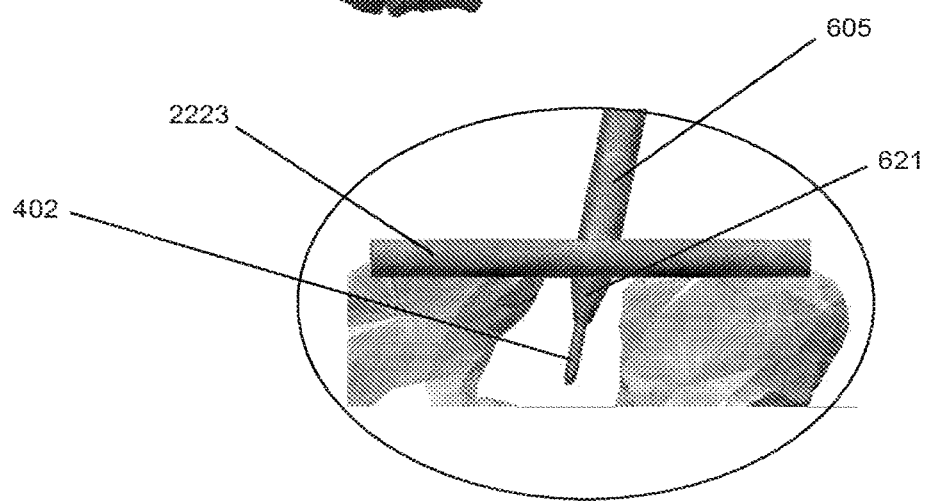
FIG. 25a is a detailed view of the first illustrative dilator as inserted through the supraspinous ligament to an appropriate depth.

FIG. 25 shows dilator 605 placed over K-wire 402 and inserted through the supraspinous ligament 2223 at the zero point 2025. FIG. 25A is an enlarged view which shows the tapered end portion 621 of dilator 605 located just past the anterior side of the supraspinous ligament 2223.

After the insertion of the first dilator to start the tissue dilation in Step 4 of the illustrative procedure, the K-wire is removed. This is indicated by block 2136 in FIG. 21.

Block 2138 in FIG. 21 indicates Step 5 in the illustrative procedure in which dilation of tissue is continued. Here, the second illustrative dilator 705 (FIG. 7) is inserted over the first illustrative dilator 605 to an appropriate depth so that the tapered end portion 721 of dilator 705 is located just past the anterior side of the supraspinous ligament 2223 (FIG. 22). The appropriate depth is determined using fluoroscopy, or alternatively, by aligning the proximal end of dilator 705 with the groove 611 in dilator 605. In some applications of the invention, it may be helpful for the operator to rotate or rock the dilator 705 using a back and forth motion as it is being inserted through the tissue. Markers, such as circumferential groove 711 and longitudinal groove 715, described above, generally provide alignment and/or proper depth control of dilator 705. In addition, the spinous process channel 726 on dilator 705, which is also described above, helps to maintain a desired mid-line positioning of dilator 705 with respect to the supraspinous ligament 2223.

In alternative arrangements, a third dilator (not shown) may be utilized. Such third dilator may be arranged to be; a) smaller in diameter than dilator 605; b) intermediately-sized between dilator 605 and dilator 705; or c) larger in diameter than dilator 705. Use of such a third dilator is optional in most applications, but may be helpful to minimize tissue trauma.

FIG. 26 shows dilator 705 placed over dilator 605 and inserted through the supraspinous ligament 2223 at the zero point 2025. FIG. 26A is an enlarged view which shows the tapered end portion 721 of dilator 705 located just past the anterior side of the supraspinous ligament 2223. FIG. 26B shows the alignment of circumferential notch 611 with the top of the proximal end of dilator 705 as a means of assuring proper depth control of dilator 705 with respect to dilator 605, zero point 2025, and supraspinous ligament 2223.

After dilator 705 is positioned over dilator 605 to the appropriate depth, as described above, dilator 605 is removed. Such removal is indicated by block 2140 in FIG. 21A.

Block 2143 in FIG. 21A indicates an optional Step 6 in the illustrative procedure in which the mounting bracket 802 (FIG. 8) is placed over the second illustrative dilator 705 (FIG. 7). Mounting bracket 802 is preferably oriented in-line with the spine along the mid-line of the supraspinous ligament. Such alignment may be achieved using fluoroscopy and/or using the visual and/or radiopaque markings described above in the text accompanying FIG. 8.

In alternative arrangements where a lateral approach to the supraspinous ligament is taken, the mounting bracket 802 is positioned with respect to the spine to enable such lateral approach.

Figure 27:
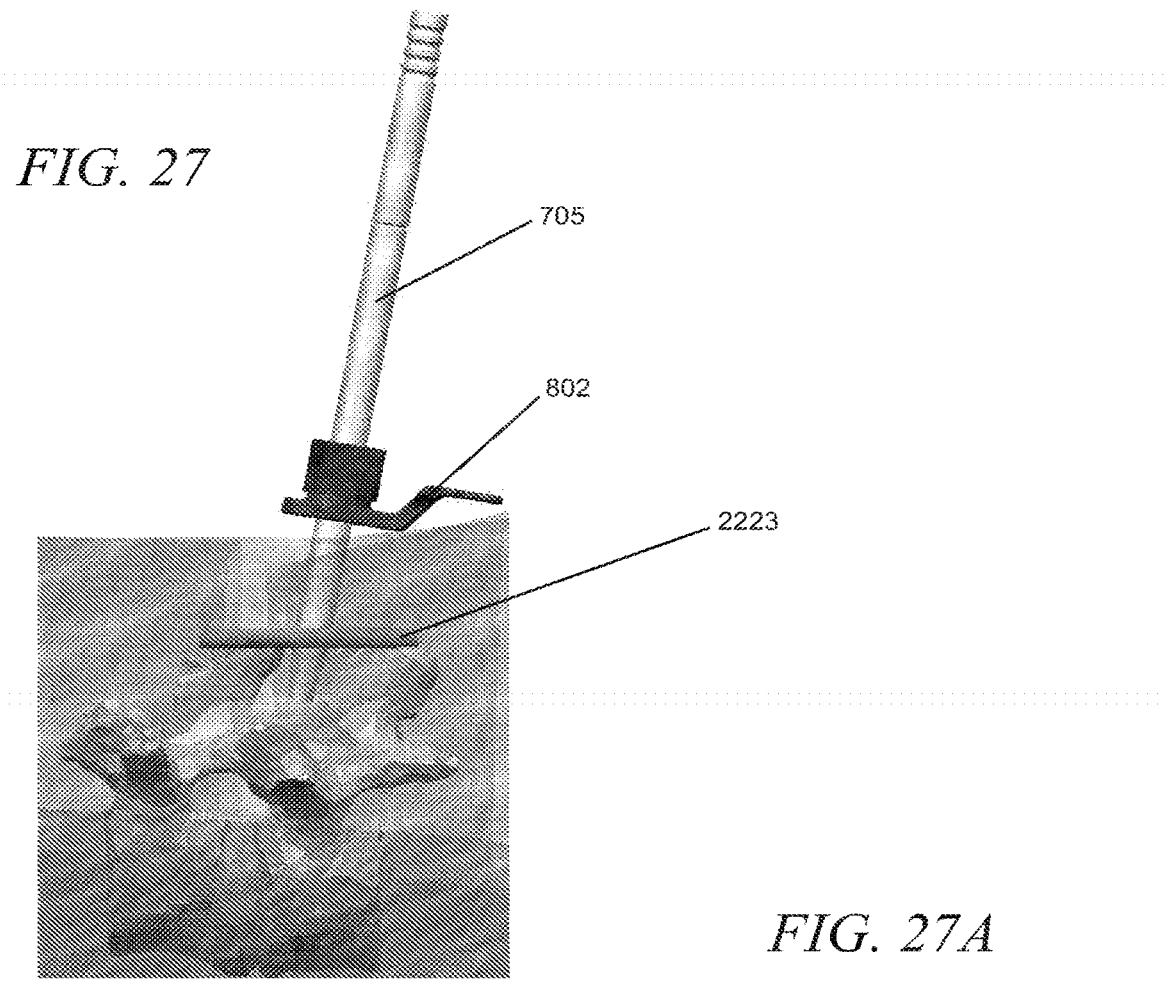
FIG. 27 is a pictorial side view of the mounting bracket shown in FIGS. 8, 8A, 8B and 8C as inserted over the second dilator.
Figure 27A:
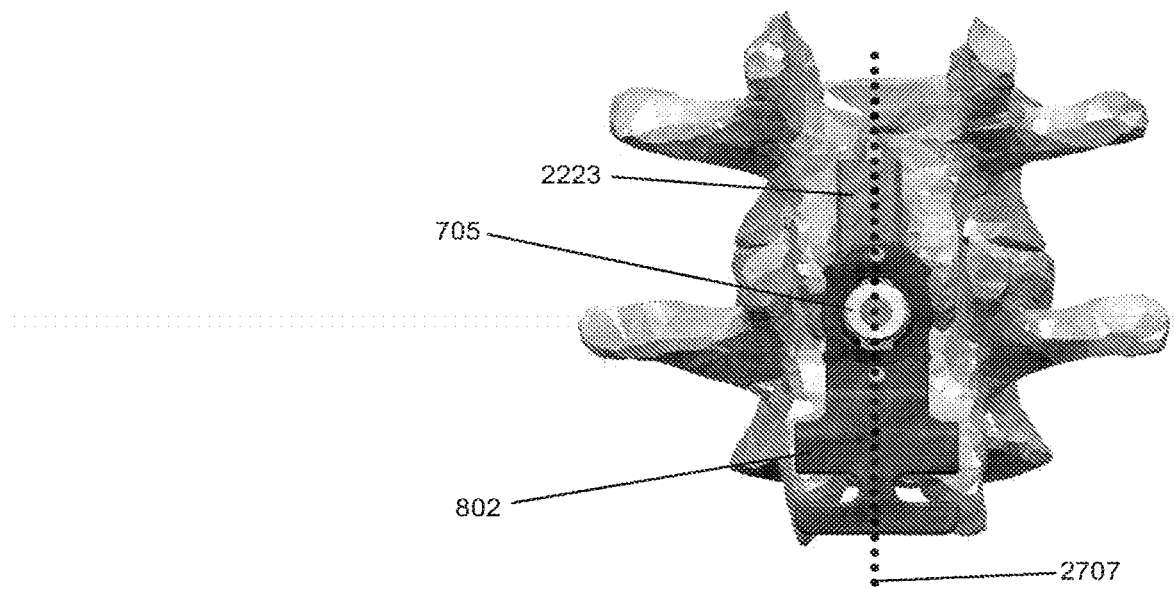
FIG. 27A is top view of the mounting bracket and dilator with respect to the mid-line of the spine.

FIG. 27 shows mounting bracket 802 placed over dilator 705. FIG. 27A shows the orientation of the mounting bracket 802 with respect to the mid-line 2707 of supraspinous ligament 2223.

Block 2143 in FIG. 21A further indicates an alternative optional approach in the illustrative procedure in which the mounting tower 850 (FIG. 8D) is used instead of the mounting bracket 802. Here, the mounting tower 850 is typically placed over the first illustrative dilator 605 (FIG. 6) after being placed into the "ready" position through manipulation of the lower collar 872 in a clockwise rotation as described above. The operator may wish to grasp the base 858 as necessary to provide a counter-torque when rotating the collar 872, if necessary.

Figure 27B:
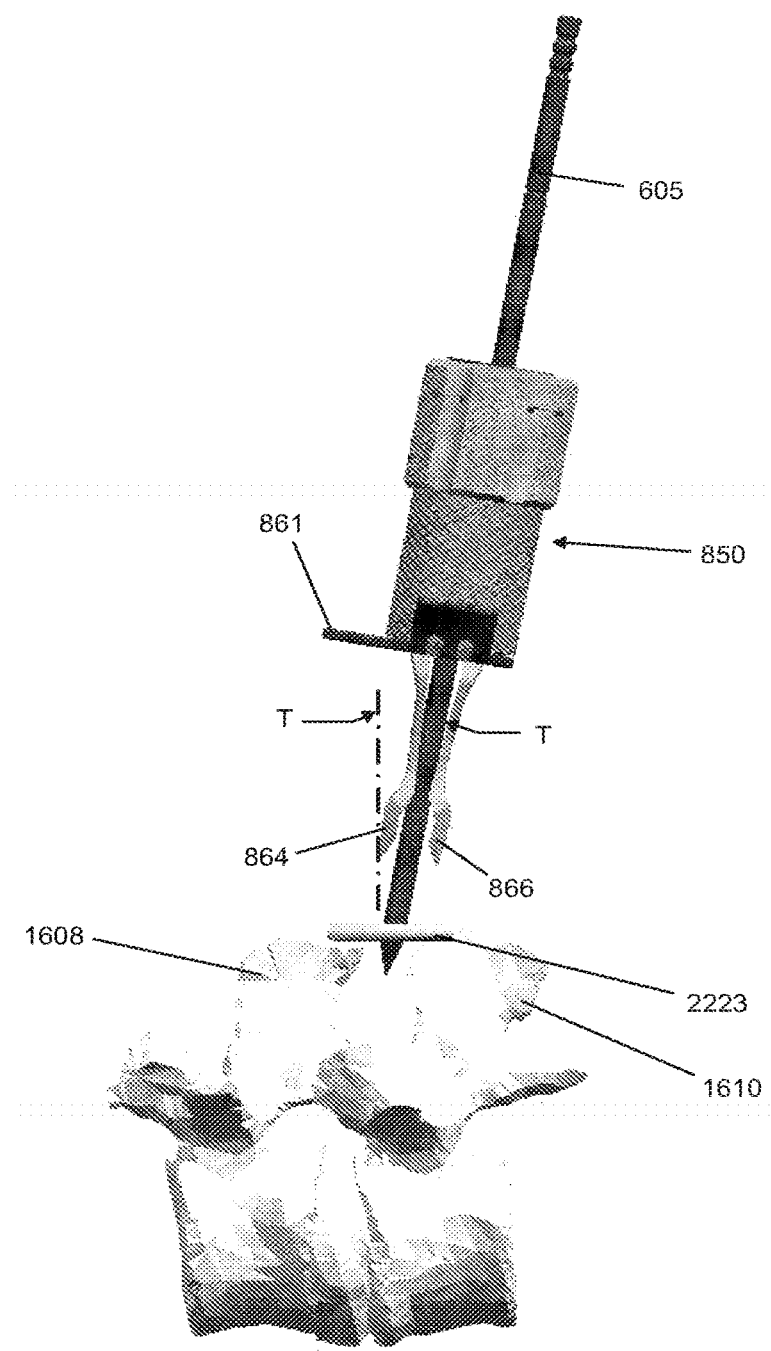
FIG. 27B is a pictorial view of an illustrative docking tower being loaded over the dilator.
Figure 27C:
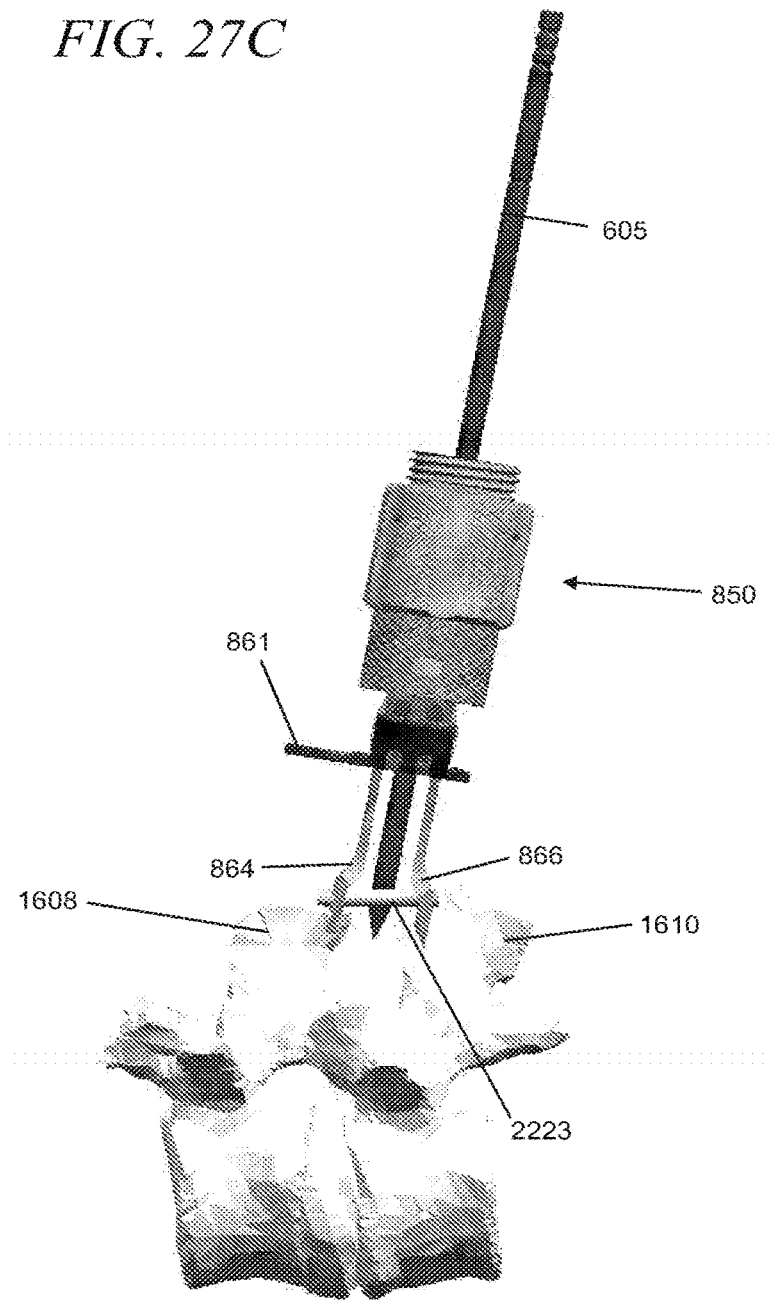
FIG. 27C is a side view of the docking tower and dilator showing a preferred trajectory with respect to the supraspinous ligament and spinous processes.
Figure 27D:
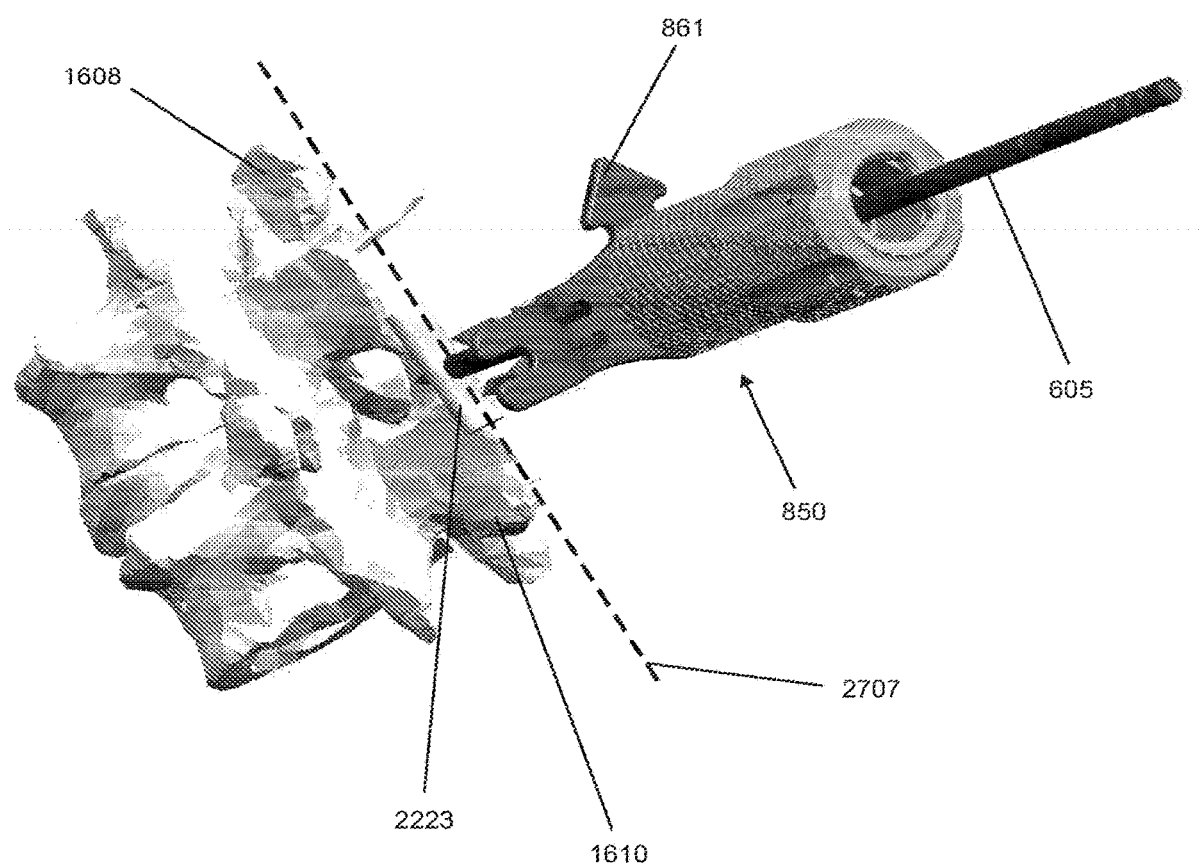
FIG. 27D is a view of the docking tower and dilator with respect to the mid-line of the supraspinous ligament.

The pointing arrow 861 of mounting tower 850 is oriented superiorly and lowered over the proximal end of the dilator 605 while maintaining the existing trajectory "T" effectuated by the dilator 605 as shown in FIG. 27B and mid-line orientation as shown in FIG. 27D. Preferably, dilator 605 is not further advanced into the interspinous space as the mounting tower 850 is positioned.

Once the distal tips of the spinous process grippers 864 and 866 are inserted through the incision, the operator begins to de-rotate the collar 872 in a counterclockwise direction to allow the distal tips to be inserted through the fascia just lateral of the supraspinous ligament 2223. Mounting tower 850 is lowered until the superior depth post 870 contacts the supraspinous ligament 2223. The operator should recheck that the mid-line orientation and trajectory are satisfactorily maintained.

Figure 27E:
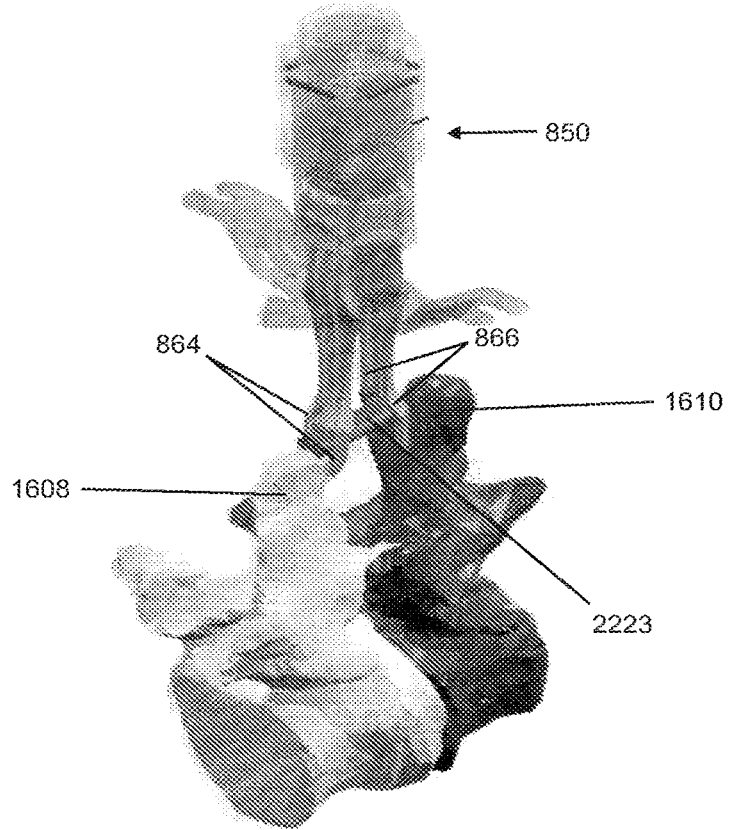
FIG. 27E is a view of the docking tower in a deployed position.

Collar 872 is then fully de-rotated to enable the spinous process grippers 864 and 866 to fully extend, as shown in FIG. 27E. The upper collar 880 is then rotated clockwise to tighten the spinous process grippers 864 and 866 and clamp the superior spinous process 1608 and inferior spinous process 1610, respectively. The operator should verify that the mounting tower 850 is firmly clamped to the spinous processes. If adjustment is required, collar 880 is de-rotated counterclockwise and then subsequently retightened.

Figure 27F:
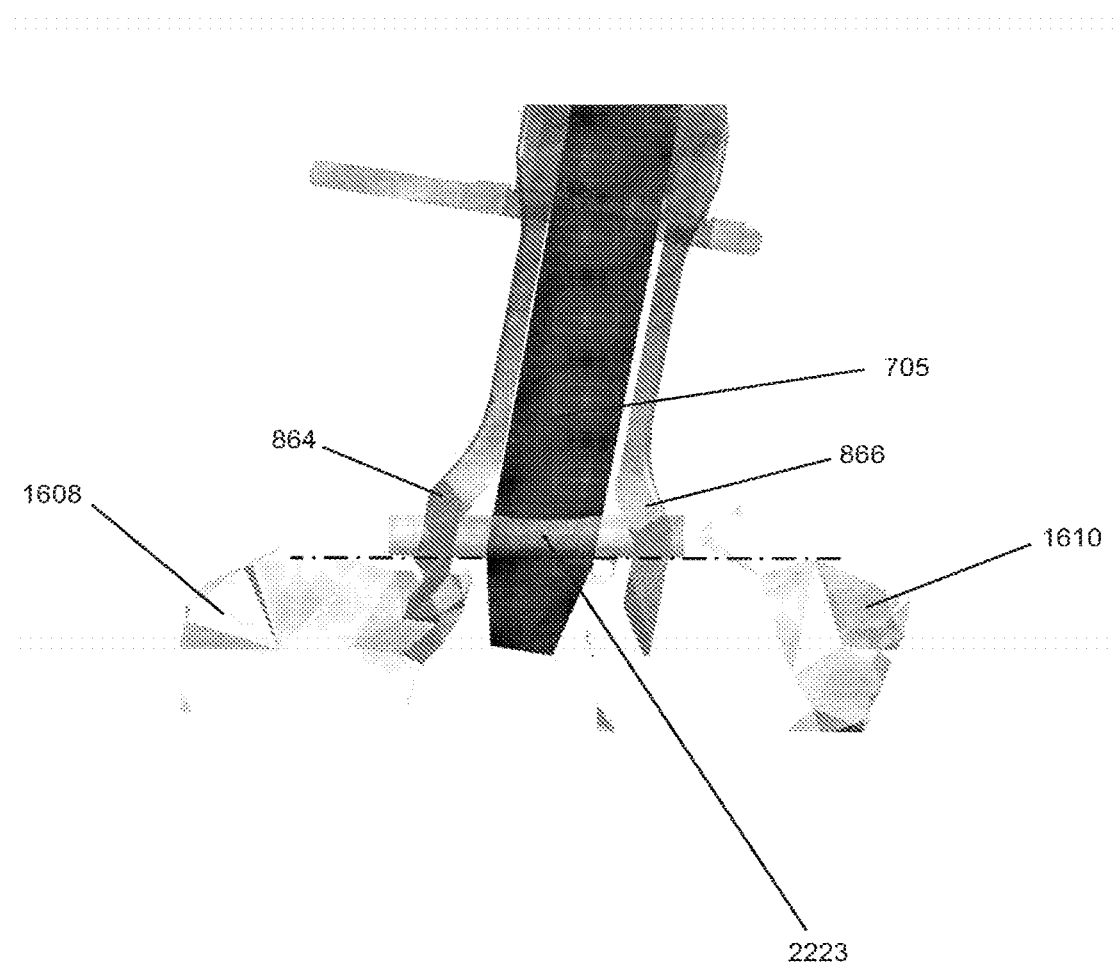
FIG. 27F is a detailed side view of the docking tower and dilator showing the positioning of the distal end of the dilator just past the anterior side of the supraspinous ligament.

The second illustrative dilator 705 (FIG. 7) is then placed over the first illustrative dilator 605 and through the center lumen of the mounting tower 850. The second illustrative dilator 705 is inserted over the first illustrative dilator 605 to an appropriate depth so that the tapered end portion 721 of dilator 705 is located just past the anterior side of the supraspinous ligament 2223 as shown in FIG. 27F. The appropriate depth is determined using fluoroscopy, or alternatively, by aligning the proximal end of dilator 705 with the groove 611 in dilator 605. In some applications of the invention, it may be helpful for the operator to rotate or rock the dilator 705 using a back and forth motion as it is being inserted through the tissue. Markers, such as circumferential groove 711 and longitudinal groove 715, described above, generally provide alignment and/or proper depth control of dilator 705. In addition, the spinous process channel 726 on dilator 705, which is also described above, helps to maintain a desired mid-line positioning of dilator 705 with respect to the supraspinous ligament 2223.

Block 2146 in FIG. 21A indicates Step 7 in the illustrative procedure in which a working channel is created by the insertion of cannula 903 (FIG. 9) over the second dilator 705 (FIG. 7) and, if utilized, through mounting bracket 802 (FIG. 8). The operator may rotate and/or rock cannula 903 during insertion in some applications of the invention. In some alternative applications, the second dilator 705 may be used to distract the spinous processes using its tapered end portion 721.

Pointing arrow 912 (FIG. 9) of cannula 903 is aligned by the operator with the cephalad and mid-line of the supraspinous ligament. The markers 811 disposed in mounting bracket 802 are also used to align the mounting bracket 802 with the mid-line of the supraspinous ligament. The cannula 903 is advanced to an appropriate position where the spinous processes channels 924 at its distal end is aligned and/or touching (i.e., mating) with adjacent spinous processes. In some applications, the appropriate depth is achieved by having the operator align the top of proximal end of the cannula 903 with the circumferential groove 711 in the dilator 705.

Once the cannula 903 is positioned, the operator locks the mounting bracket 802 to the cannula 903 by turning the nut 813 (FIG. 8). Second dilator 705 is removed as indicated in block 2149 in FIG. 21A and mounting bracket 802 is then fixedly attached to a stabilizing device such as stabilizing arm 1012 (FIG. 10).

Figure 28:
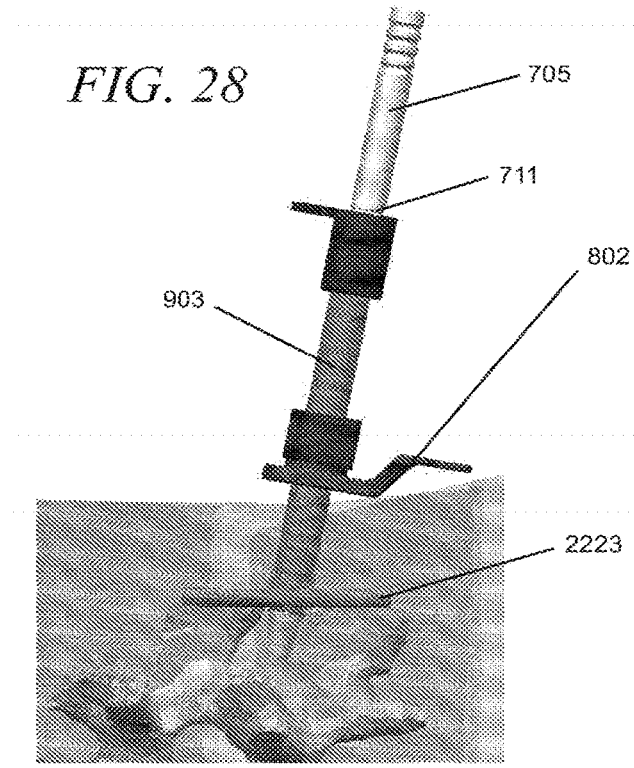
FIG. 28 is a pictorial side view of the cannula shown in FIGS. 9, 9A and 9B as inserted through the mounting bracket and over the dilators.
Figure 28B:
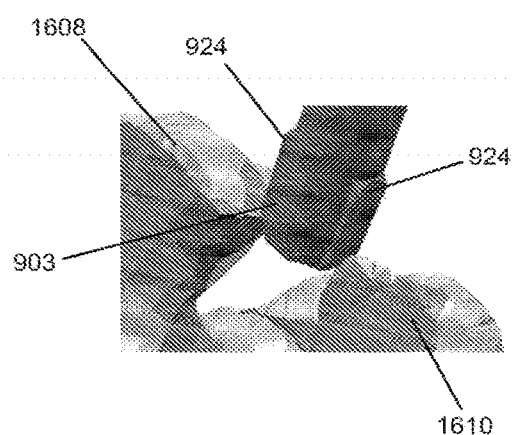
FIG. 28B is a detailed side view of the distal end of the cannula with respect to the distal end of the dilator, supraspinous ligament, and spinous processes.
Figure 28A:
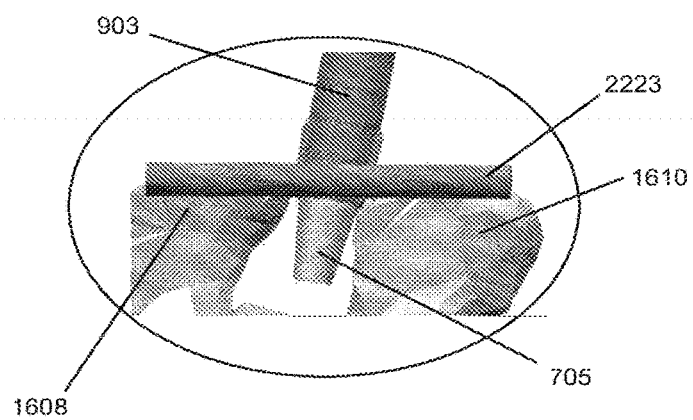
FIG. 28A is a detailed view of the distal end of the cannula showing the alignment of the end channels with the spinous processes.
Figure 28C:
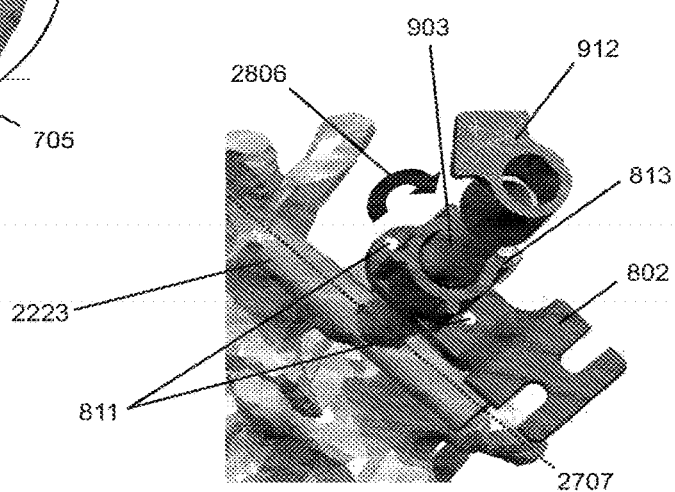
FIG. 28C is a pictorial view of the mounting bracket and cannula showing the locking orientation of a rotating nut.

FIG. 28 shows the operative relationship between the cannula 903, mounting bracket 802 and second dilator 705 where the top of the proximal end of cannula 903 is aligned with the groove 711 in dilator 705. FIG. 28A is an enlarged view showing the cannula 903 inserted through the supraspinous ligament 2223 prior to the removal of dilator 705. FIG. 28B is an enlarged view showing a desired alignment of the spinous process channels 924 with the superior spinous process 1608 and inferior spinous processes 1610. FIG. 28C shows a desired alignment of the markers 811 in mounting bracket 802 and pointing arrow 912 of cannula 903 with the mid-line 2707 of the supraspinous ligament 2223. FIG. 28C also shows the operative relationship between the mounting bracket 802 and cannula 903 whereby the nut 813 is rotated (as indicated by the reference arrow 2806) in order to clamp cannula 903 in a releasable fashion. Note that in FIG. 28C, a stabilizing device, such as stabilizing arm 1012 (FIG. 10) may be used but is not shown.

Figure 28D:
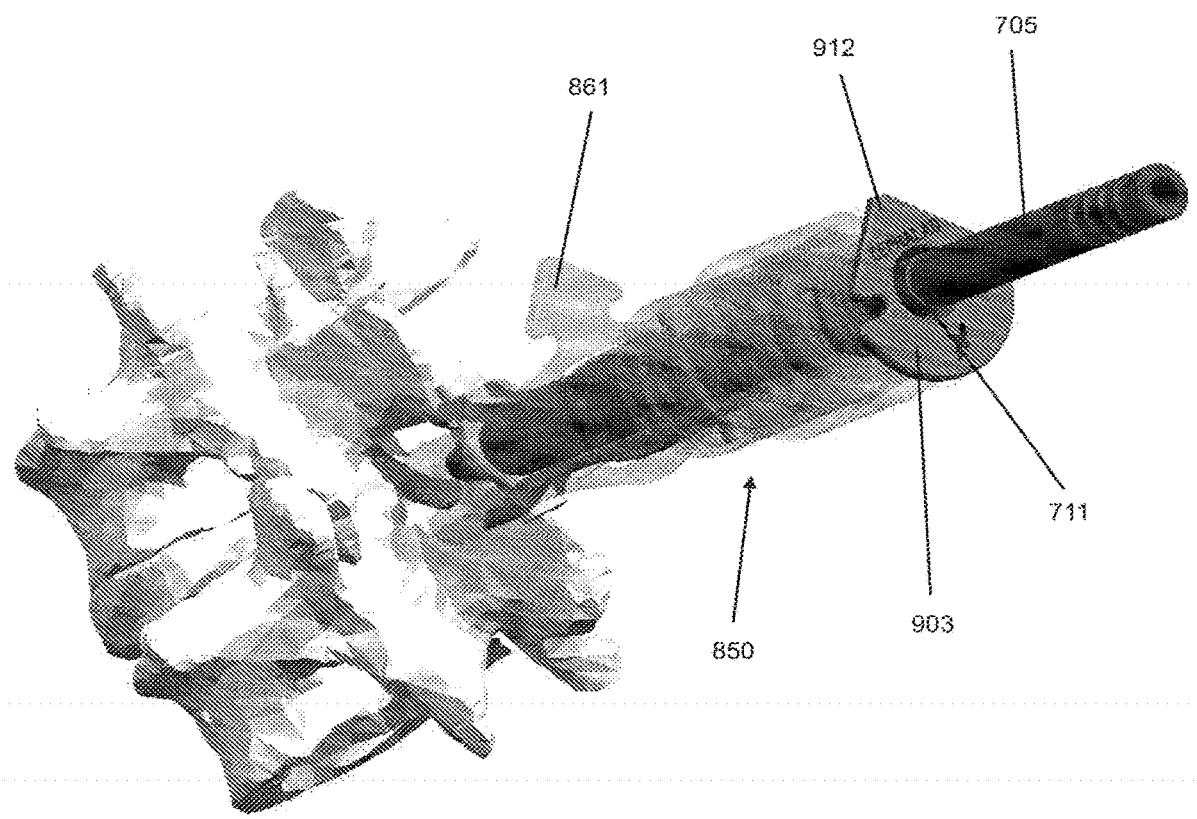
FIG. 28D is a pictorial view of the mounting tower, cannula and dilator.

In cases where the mounting tower 850 (FIG. 8D) is utilized instead of the mounting bracket 802, the first illustrative dilator 605 is removed from the mounting tower 850. The cannula 903 (FIG. 9) is inserted over the second illustrative dilator 705 and through the center lumen of the mounting tower 850 as shown in FIG. 28D. The operator ensures the correct orientation of cannula 903 by aligning the cannula's pointing arrow 912 with pointing arrow 861 of the mounting tower 850. The cannula 903 is advanced to an appropriate position where the spinous processes channels 924 at its distal end is aligned and/or touching (i.e., mating) with adjacent spinous processes. In some applications, the appropriate depth is achieved by having the operator align the top of the proximal end of the cannula 903 with the circumferential groove 711 in the dilator 705.

Block 2155 in FIG. 21A shows Step 8 in the illustrative procedure in which the interspinous knife 1102 (FIG. 11) is inserted into the cannula 903. In most applications, the interspinous knife 1102 is inserted just to the distal end of cannula 903 by lowering the interspinous knife 1102 until its shoulder feature 1121 (FIG. 11) bottoms out on the counterbore 918 (FIG. 9B) of cannula 903. Alternatively, the interspinous knife 1102 is inserted to a depth in cannula 903 that is determined using other depth indicators (including for example, visual markers), or to some fixed depth, or as indicated through use of fluoroscopy.

Once inserted into cannula 903 to the desire depth, interspinous knife 1102 is generally operated to perform one, or in some applications more than one, plunge cut. A typical plunge cut depth is 15 mm, although interspinous knife 1102 may be arranged as shown in FIGS. 11 and 11B to be adjustable so that other plunge cut depths are achievable, for example, 20 mm in typical alternative arrangements. In alternative arrangements, other set plunge cut depths may be accommodated by interspinous knife 1102, or an infinitely adjustable plunge cut depth may be utilized.

In some applications of the invention where a second plunge cut is utilized, interspinous knife 1102 is typically adjusted so that the cutting blades 1117 (FIG. 11) are rotated to thereby enable the second plunge cut to be oriented at a different angle from the first plunge cut. With the interspinous knife 1102 shown in FIGS. 11, 11A and 11B, such adjustment is effectuated by rotating the inner tube 1110 to some desired angle with respect to outer tube 1115. As noted above, such rotation may be arranged using constrained rotation angles in an indexed manner. Alternatively, interspinous knife 1102 may be rotated with respect to cannula 903 to implement a rotated second plunge cut. In alternative arrangements, interspinous knife 1102 may be configured to use a mechanically assisted plunge cut.

Upon completion of the desire plunge cuts, interspinous knife 1102 is removed from cannula 903.

Figure 29:
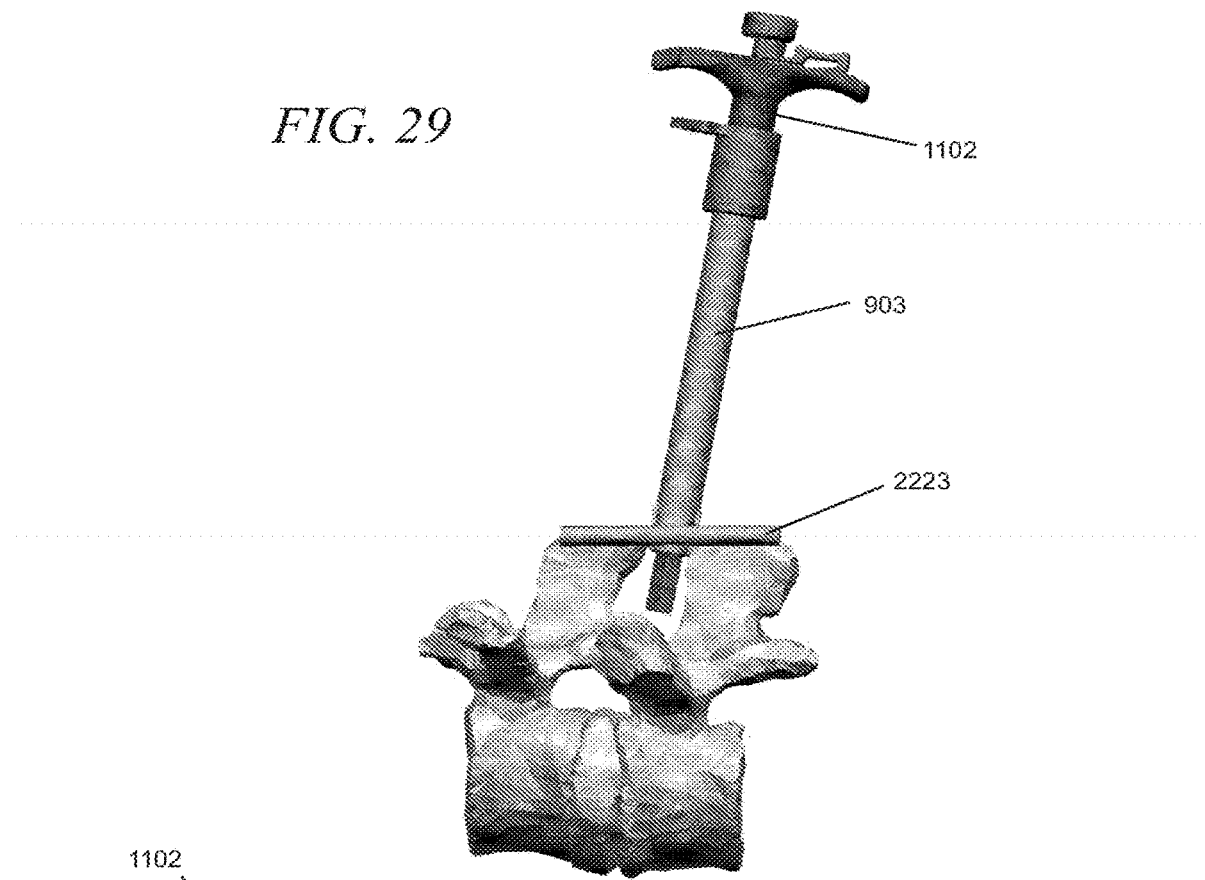
FIG. 29 is a pictorial view of the interspinous knife shown in FIGS. 11, 11A and 11B as inserted into the cannula.
Figure 29A:
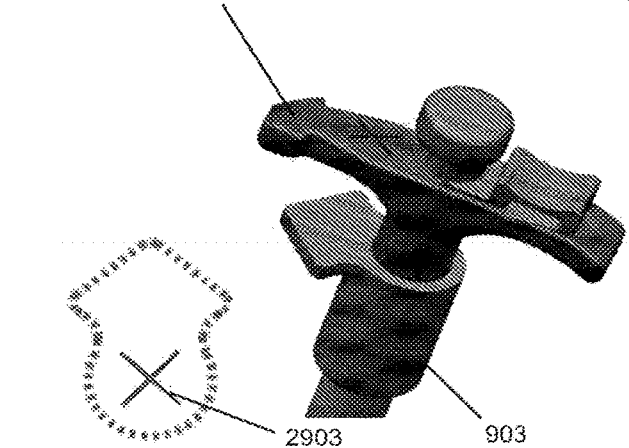
FIG. 29A is a detailed view of the initial cut pattern and the orientation of the interspinous knife with respect to the cannula.
Figure 29B:
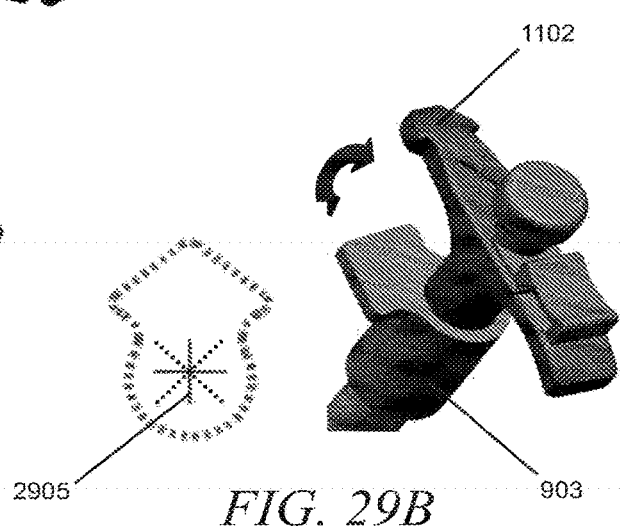
FIG. 29B is a detailed view of an optional cut pattern that is oriented 45 degrees from the initial cut through rotation of the interspinous knife with respect to the cannula.

FIG. 29 shows the operative relationship between the interspinous knife 1102 and cannula 903 when the interspinous knife 1102 is oriented to the appropriate depth through supraspinous ligament 2223. FIG. 29A shows the cutting pattern 2903 of the initial plunge cut. FIG. 29B shows the cutting pattern 2905 of the second plunge cut that is implemented through rotation of the interspinous knife 1102 with respect to the cannula 903. In the illustrative example shown in FIGS. 29A and 29B, the first and second plunge cuts are rotated 45 degrees with respect to each other. As noted above, other rotation angles may be employed as may be desired for a particular application of the invention.

Step 8 in the illustrative procedure may alternatively use interspinous knife 1130 (FIG. 11C) instead of interspinous knife 1102, or to supplement the cuts made by interspinous knife 1102.

Block 2158 in FIG. 21 shows an optional Step 9 in the illustrative procedure in which interspinous reamer 1201 (FIG. 12B) is used, as needed, to remove bone and/or other tissue in order to create a working space for an interspinous spacer. In typical applications where the interspinous reamer is used, the hole cutter 1212 (FIG. 12A) is first inserted through the cannula 903 (FIG. 9). Depth control may be maintained, for example, visually or using mechanical indicators or stops as the hole cutter 1212 cuts the tissue. Core cutter 1208 (FIG. 12) is then inserted into the hole cutter 1212 so that the hole cut of the tissue is followed by core cut by the core cutter 1208 to evacuate the tissue from the tube of the hole cutter 1212. Depth control of core cutter 1208 is maintained visually or using mechanical indicators or stops, for example. Once the interspinous reamer 1201 completes the tissue cutting, it is removed from cannula 903.

In alternative arrangements, optional Step 9 in the illustrative procedure may use one or more interspinous reamers that are configured to have different diameters and/or different distal end geometries to accommodate a variety of tissue types.

Block 2161 in FIG. 21 shows Step 10 in the illustrative procedure in which the interspinous gauge 1306 (FIG. 13) is used to measure or size the appropriate interspinous spacer for a particular patient application by measuring the space between the spinous processes. The interspinous gauge 1306 is first inserted through the cannula 903 (FIG. 9) where the depth and alignment of the insertion is typically determined through use of markers or via fluoroscopy. Alternatively, the widened shoulder feature 1330 (FIG. 13) of interspinous gauge 1306 is configured to engage with the counterbore 918 and flat 921 (FIG. 9) in cannula 903 when the interspinous gauge 1306 is inserted through the lumen 906 of cannula 903. Such engagement between the shoulder feature and counterbore/flat may thereby locate and align the interspinous gauge 1306 at the proper depth and orientation with respect to the cannula 903 and the spine.

The operator then manipulates the control lever 1314 (FIG. 13) to radially extend the feelers 1317 to touch adjacent spinous processes. The operator reads the distance between the distal ends of the feelers on a gauge or other visual readout on the interspinous gauge 1306.

Figure 30:
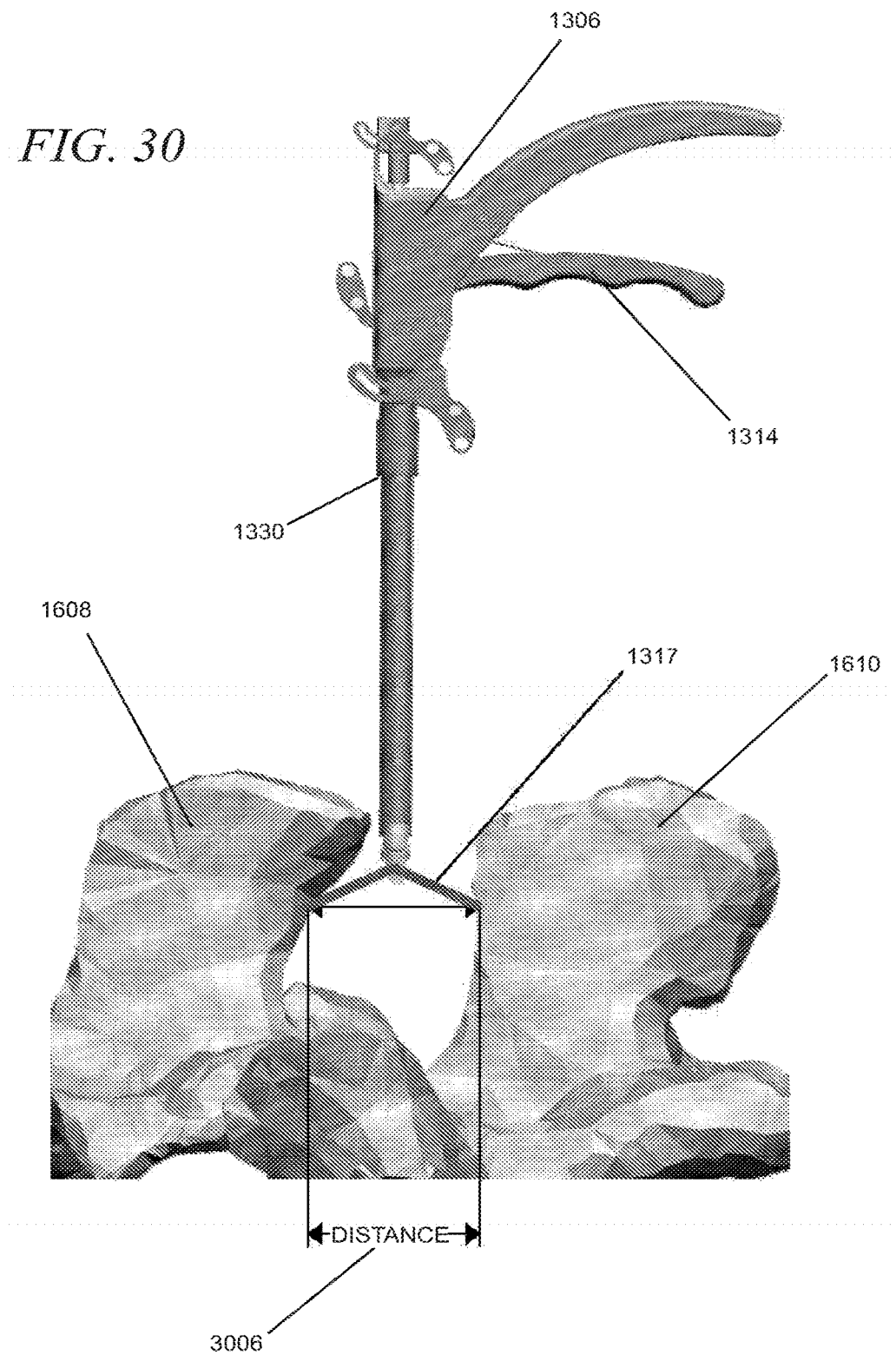
FIG. 30 is a pictorial view of the first illustrative interspinous gauge shown in FIGS. 13 and 13A making a measurement of the interspinous space between the superior and inferior spinous processes.

FIG. 30 shows the interspinous gauge 1306 with deployed feelers 1317 in operative relationship with the superior and inferior spinous processes 1608 and 1610. The distance indicated by reference numeral 3006 is provided to the operator on a gauge that is typically affixed to interspinous gauge 1306 to assist in selecting the appropriately sized interspinous spacer. Note that the cannula 903 is not shown for the sake of clarity in the illustration.

In alternative arrangements, Step 10 in the illustrative procedure may include using the interspinous gauge 1306 to distract the spinous processes. Once the spinous processes are distracted, the interspinous gauge 1306 may be used as a measuring instrument as described above. The interspinous gauge 1306 may further be configured and used to measure the force applied to the spinous processes during distraction.

Interspinous gauge 1306 may be further utilized during Step 10 in the illustrative procedure to provide "Go" and/or "No Go" information as described above in the text accompanying FIGS. 13 and 13A. Such information may be helpful in shortening the procedure and avoiding wasting product (e.g., interspinous spacer) and disposable tooling when it is determined that a No Go condition exists.

Figure 30A:
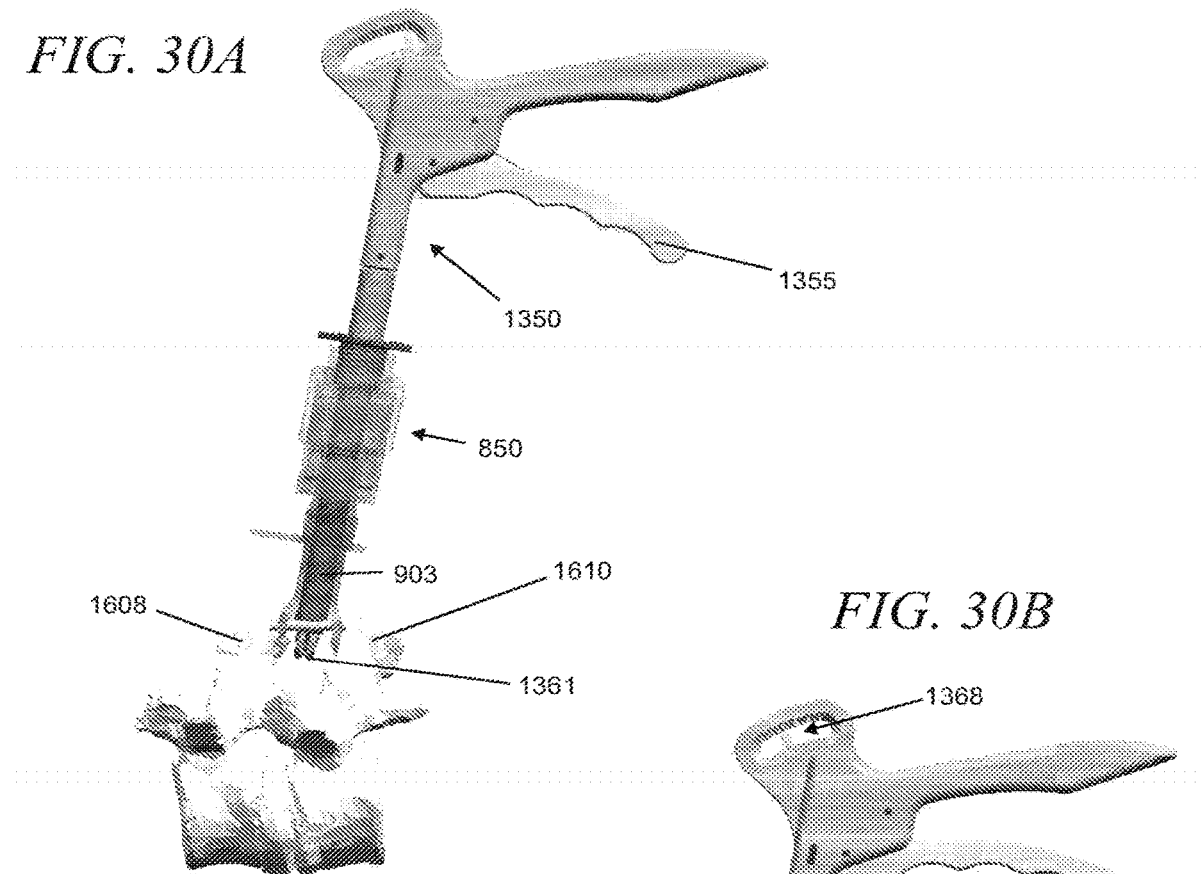
FIGS. 30A and 30B are pictorial views of the second illustrative interspinous gauge shown in FIGS. 13B, 13C and 13D.
Figure 30B:
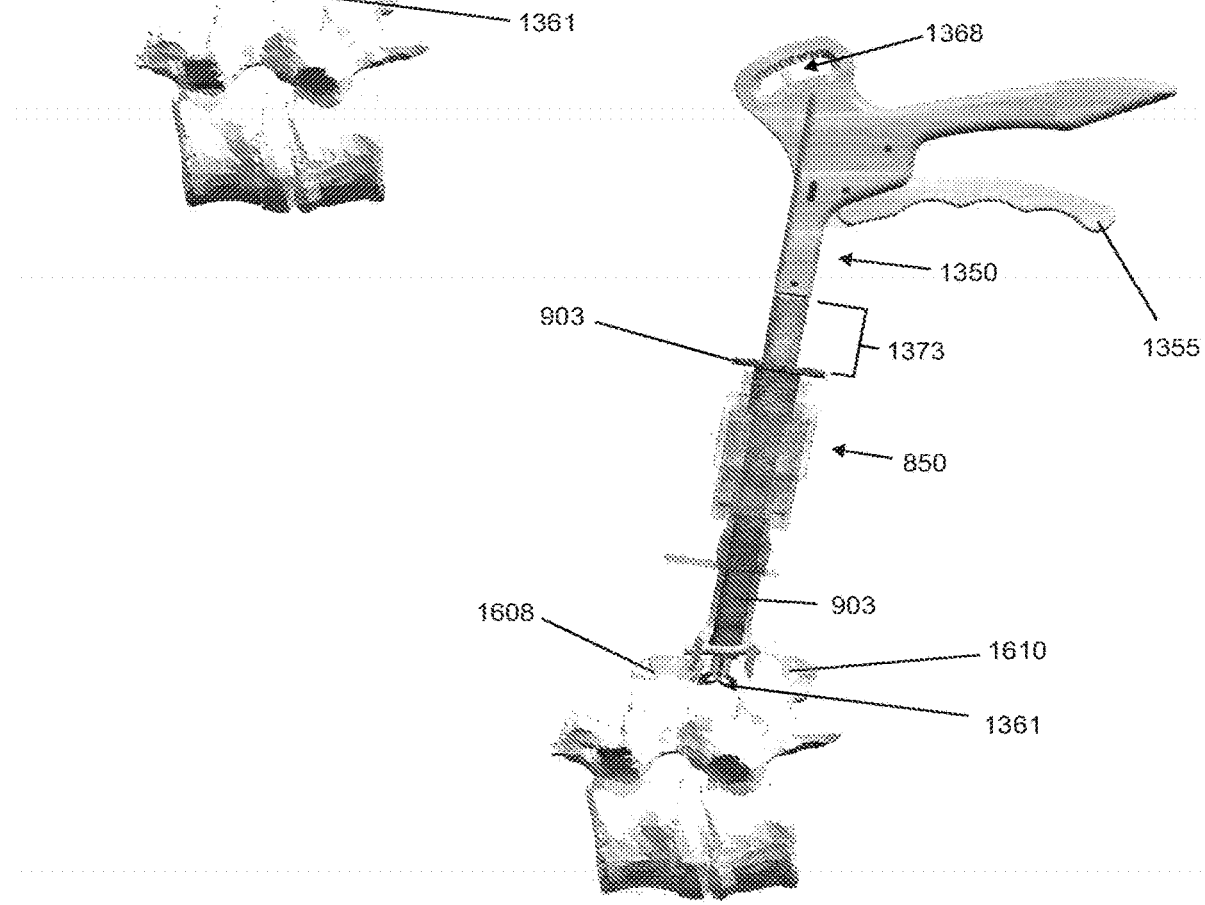

Step 10 in the illustrative procedure may be alternatively performed using interspinous gauge 1350 (FIG. 13B), as shown in FIGS. 30A and 30B. In this alternative process step, interspinous gauge 1350 is shown inserted through cannula 903 (FIG. 9) as held in the alternatively utilized mounting tower 850 (FIG. 8D) rather than the mounting bracket 802 (FIG. 8). The operator firmly actuates trigger 1355 until resistance is detected at the distal feelers 1361. As the supraspinous ligament may relax over time, the interspinous space measurement is preferably taken over a two to four minute time interval. A readout of the distance between adjacent spinous processes is provided on the gauge 1368. The insertion depth is read from the markings disposed on the marker area 1373 with respect to the top of the cannula 903. In some applications, an accurate measurement is achieved after some degree of distraction of the spinous processes is performed.

Steps 11 and 12 in the illustrative procedure are described below with reference to FIGS. 31A-F which show the interspinous spacer 1440 (FIG. 14) in various positions. Interspinous spacer 1440 comprises a body 3102, actuator 1458, and cam lobes which are pivotally mounted to the body 3102. A superior cam lobe 3105 is arranged to interface with the superior spinous process when the interspinous spacer 1440 is deployed. An inferior cam lobe 3110 interfaces with the inferior spinous process when the interspinous spacer 1440 is deployed.

Figure 31A:
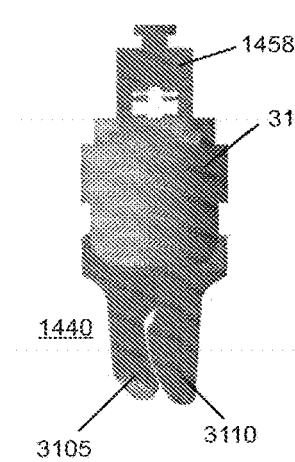
FIGS. 31A-F are pictorial views of an interspinous spacer in a variety of positions.
Figure 31C:
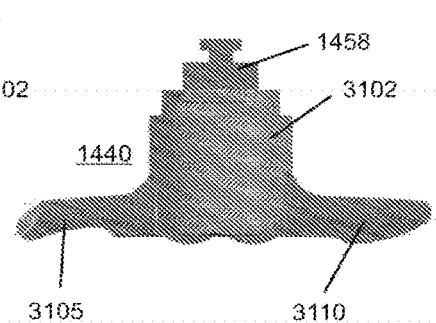
Figure 31E:
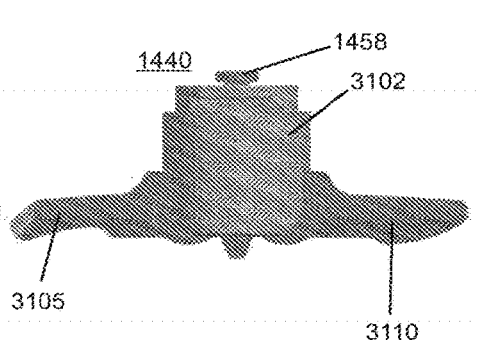
Figure 31B:
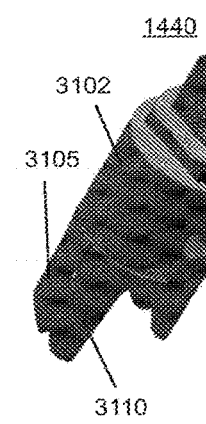
Figure 31D:
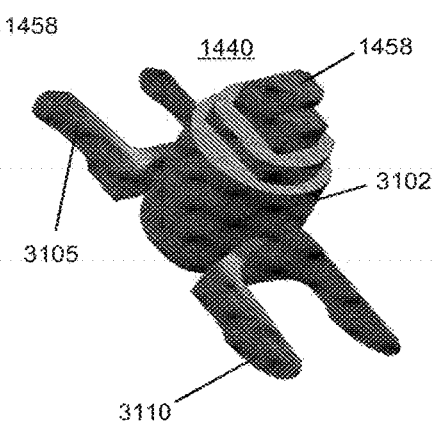
Figure 31F:
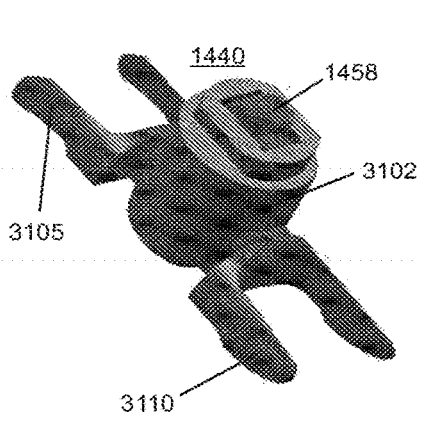

FIGS. 31A and 31B show the interspinous spacer 1440 in the Undeployed position in which the superior cam lobe 3105 and inferior cam lobe 3110 are in a non-extended (i.e., collapsed) position and the actuator 1458 is in a fully extended position with respect to the body 3102. FIGS. 31C and 31D show the interspinous spacer 1440 in the Deployed position in which the superior cam lobe 3105 and inferior cam lobe 3110 are rotated about their pivots to extend laterally outward from the body 3102. When in the deployed position, the actuator 1458 is partially translated into body 3102. FIGS. 31E and 31F show the interspinous spacer in the Extended position in which the superior cam lobe 3105 and inferior cam lobe 3110 are further extended laterally from the body 3102. When in the extended position, actuator 1458 is fully translated into body 3102.

Referring again to FIG. 21A, block 2167 shows Step 11 in the illustrative procedure in which an undeployed interspinous spacer is loaded on the insertion instrument 1404 (FIG. 14). Referring to FIGS. 31G-K, the operator first ensures that the inner shaft 1422 (FIG. 31H) of insertion instrument 1404 is fully retracted by appropriate manipulation of deployment lever 1419 (FIG. 31G) so that the deployment scale 1470 (FIG. 31I) indicates "L" for load. The operator then confirms the proper orientation of the interspinous spacer 1440 (FIG. 31J) with respect to the insertion instrument 1404 by aligning the extended tang 1428 (FIG. 14B) to the spacer 1440. Actuation of the second operating lever 1438 (FIG. 31G) locks the inner clamping mechanism 1455 at the distal end of the inner shaft 1422 to the actuator 1458 of the interspinous spacer 1440 as shown in FIGS. 31H, 31J, and 31K. Next, actuation of the first operating lever 1435 (FIG. 31G) locks the outer clamping mechanism 1426 to the lateral ribs on the proximal end of interspinous spacer 1440. In an alternative arrangement of the invention, it may be desirable to utilize only a single (e.g., the inner) clamping mechanism to lock the interspinous spacer 1440 to the insertion instrument 1404. Once loaded onto insertion instrument 1404, interspinous spacer 1440 is ready to be implanted.

Block 2172 in FIG. 21 shows Step 12 in the illustrative process in which the interspinous spacer 1440 (FIG. 14) is deployed. The insertion instrument 1404 (FIG. 14), with the interspinous spacer 1440 loaded as described above, is inserted into cannula 903 (FIG. 9). The insertion instrument 1404 is then advanced by the operator to a desired depth using, for example, depth markings under fluoroscopy. Alternatively by bottoming the widened shoulder feature 1473 (FIG. 14) against the counterbore 918 and flat 921 (FIG. 9) in cannula 903, insertion instrument 1404 may be located at both an appropriate "zero" depth with a desired orientation, for example, with respect to the mid-line of the supraspinous ligament. Such zero depth alignment is shown in FIG. 32.

Figure 32A:
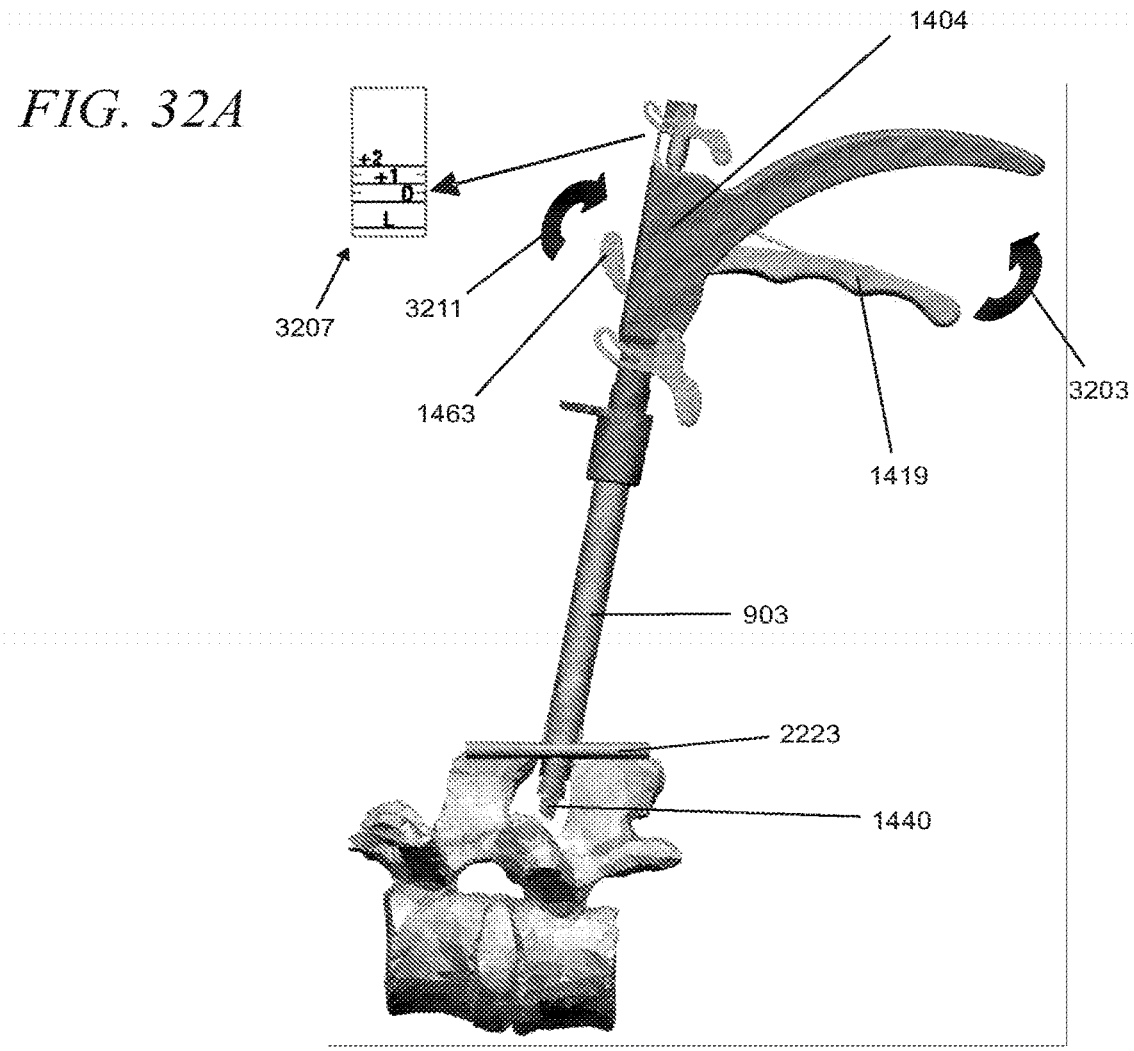
FIG. 32A is a pictorial view of the insertion instrument with loaded interspinous spacer as inserted through the cannula.
Figure 32:
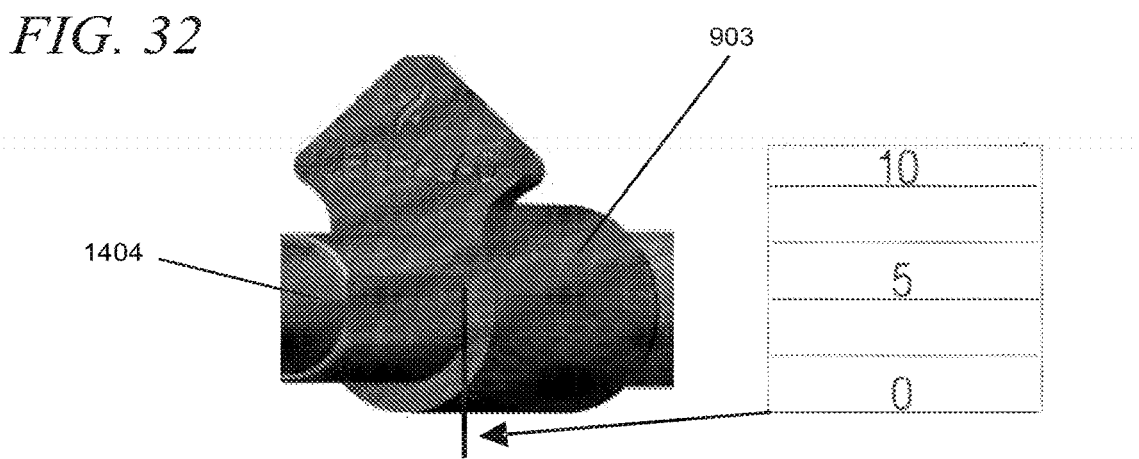
FIG. 32 is a detailed view of a flat portion of the insertion instrument in alignment with a flat surface of the cannula that sets a depth indicator of "zero"

Referring to FIG. 32A, the operator actuates deployment lever 1419 on insertion instrument 1404 as indicated by arrow 3203 until the deployment scale 3207 reaches "D" to thereby deploy the interspinous spacer 1440. The operator then confirms that the interspinous spacer 1440 is properly deployed in its expanded and locked position, and extends deployment as necessary.

The above described steps advantageously implant the interspinous spacer 1440 very precisely. Such precision prevents interspinous spacer migration, minimizes local fractures, and minimizes intrusion upon the dural canal by maintaining the interspinous spacer 1440 with the interspinous space (i.e., a "safe zone").

Optionally, the operator may reverse the extension of interspinous spacer 1440 by using retraction lever 1463.

Block 2176 in FIG. 21 shows Step 13 in the illustrative procedure in which the deployed interspinous spacer 1440 (FIG. 14) is extended to the proper height by the operator by actuating the deployment lever 1419 on insertion instrument 1404 to thereby rotate the inner shaft 1422 (FIGS. 14, 14B and 14C) and expand the interspinous spacer 1440. Such height is verified using various alternatives including, for example, visible, radiopaque, ultrasonic or magnetic markers. Upon the extension of spacer 1440 to the proper height, insertion instrument 1404, cannula 903 (FIG. 9) and mounting bracket 802 (FIG. 8) are removed. The illustrative procedure ends at block 2183 in FIG. 21A.

Figure 32B:
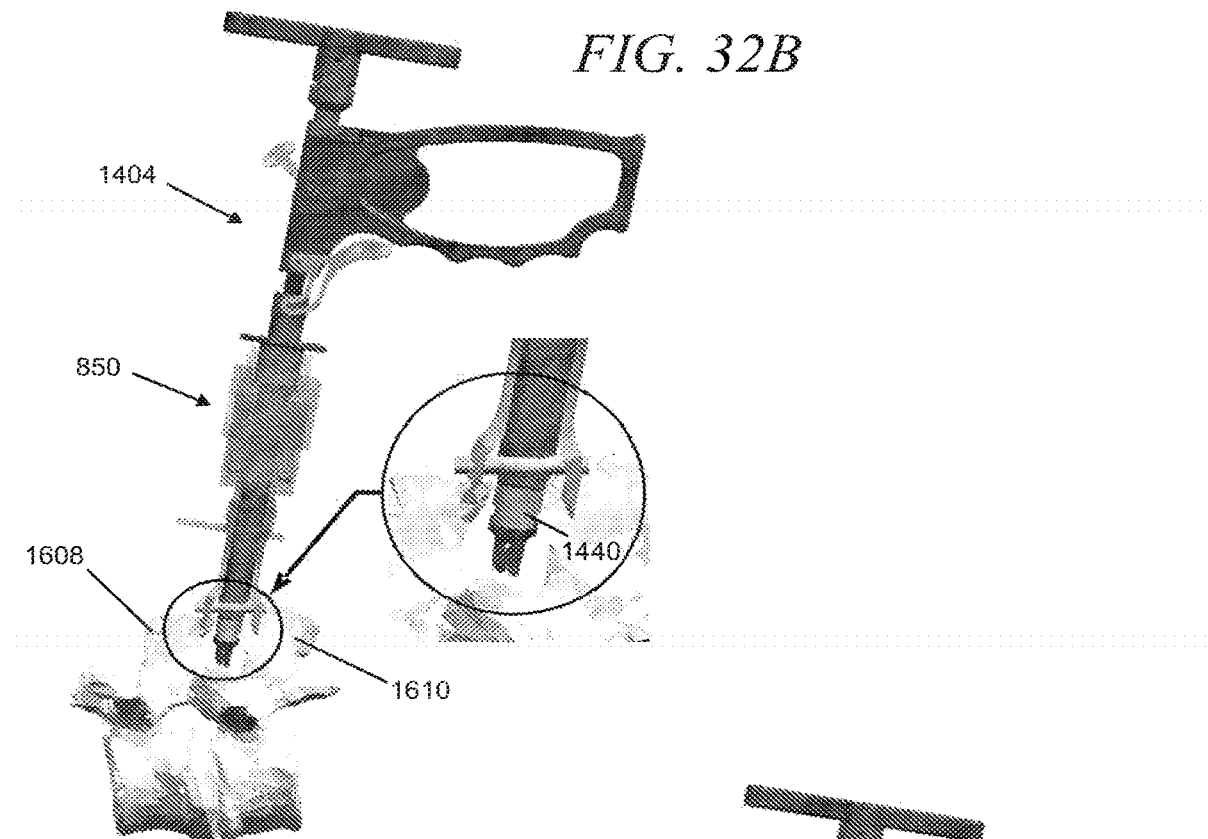
FIG. 32B is a pictorial view of the insertion instrument of FIGS. 14F and 14G in operative engagement with an interspinous spacer as placed into the interspinous space in an undeployed position.
Figure 32C:
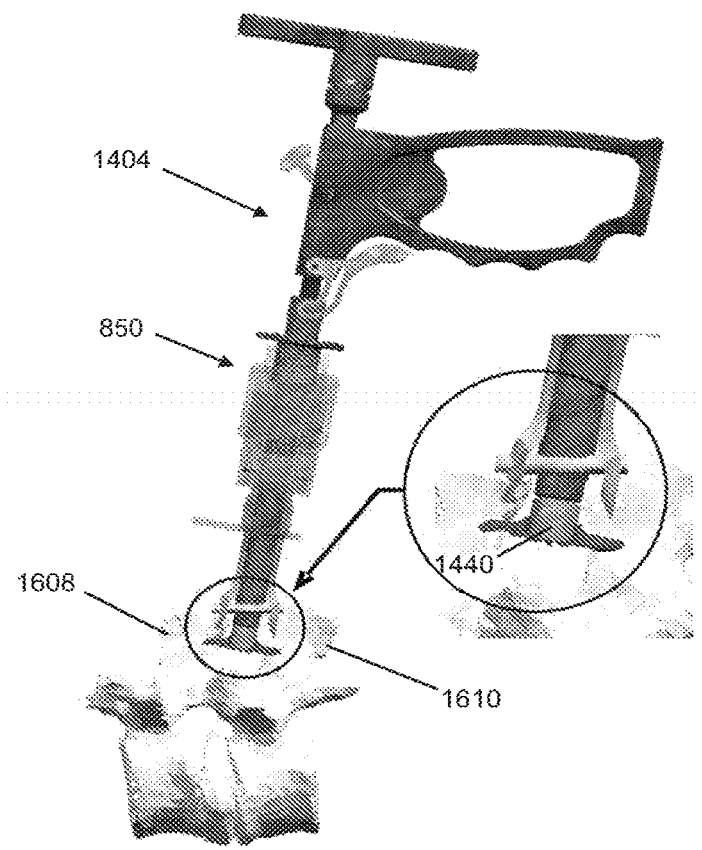
FIG. 32C is a pictorial view of the insertion instrument of FIGS. 14F and 14G in operative engagement with an interspinous spacer as placed into the interspinous space in a deployed position.

FIG. 32B is a pictorial view of the alternatively utilized insertion instrument 1404 with an attached, loaded interspinous spacer 1440 in the Undeployed position. Insertion instrument 1404 is shown with cannula 903 in the alternatively utilized mounting tower 850. FIG. 32C is a pictorial view of the interspinous spacer in the Deployed position.

Figure 33:
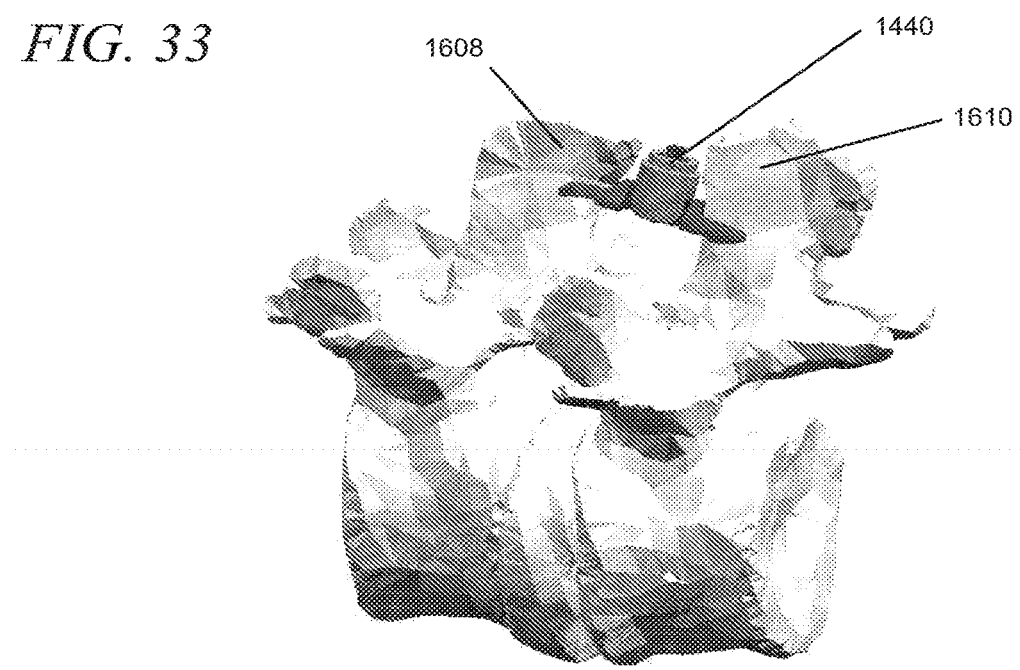
FIG. 33 is a pictorial view of an interspinous spacer as deployed.
Figure 34:
FIG. 34 is a pictorial representation of an image that shows the interspinous spacer as deployed.

FIG. 33 is a pictorial view of the interspinous spacer 1440 in the deployed condition after the insertion instrument is withdrawn. FIG. 34 is a fluoroscopic image of the interspinous spacer 1440 (FIG. 14) in the deployed condition.

The preceding merely illustrates the principles of the Invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed as new and desired to be protected by Letters Patent of the United States is:

1. An implantable spacer for placement between adjacent interspinous processes, the implantable spacer comprising:
   a body defining a longitudinal axis;
   a first arm and a second arm that are both coupled to the body and configured for rotation relative to the body, each of the first arm and the second arm having a pair of extensions spaced apart from one another to define an opening between the extensions, the opening being configured to receive a spinous process;
   an actuator extending from the body and configured for rotation relative to the body to move the first and second arms from an undeployed configuration in which the first and second arms are substantially parallel to the longitudinal axis of the body to a deployed configuration in which the first and second arms are substantially perpendicular to the longitudinal axis of the body.

2. The implantable spacer of claim 1, wherein the first and second arms retain a same shape in the deployed and undeployed configuration.

3. The implantable spacer of claim 1, wherein the actuator is configured for rotation relative to the body to move the first and second arms from the deployed configuration to the undeployed configuration.

4. A system for implanting an implantable spacer, comprising:
   the implantable spacer of claim 1;
   an insertion instrument comprising a barrel and an outer clamping mechanism disposed at a distal end of the barrel, wherein the outer clamping mechanism is configured for clamping onto the body of the implantable spacer.

5. The system of claim 4, further comprising an inner shaft extendable out of the barrel of the insertion instrument and configured for coupling to the actuator of the implantable spacer for rotation of the actuator by rotation of the inner shaft.

6. The system of claim 4, wherein the insertion instrument comprises an operating lever coupled to the outer clamping mechanism and configured to operate to lock the outer clamping mechanism onto the body of the implantable spacer.

7. The system of claim 6, wherein body of the implantable spacer comprises lateral ribs to facilitate locking the outer clamping mechanism to the body of the implantable spacer.

8. An implantable spacer for placement between adjacent interspinous processes, the implantable spacer comprising:
   a body defining a longitudinal axis;
   a first arm and a second arm that are both pivotably mounted on the body and configured for pivoting relative to the body, each of the first and second arms having a pair of extensions spaced apart from one another to define an opening between the extensions, the opening being configured to receive a spinous process;
   an actuator extending from the body and configured for rotation relative to the body to pivot the first and second arms relative to the body from an undeployed configuration in which the first and second arms are substantially parallel to the longitudinal axis of the body to a deployed configuration in which the first and second arms are substantially perpendicular to the longitudinal axis of the body.

9. The implantable spacer of claim 8, wherein the first and second arms retain a same shape in the deployed and undeployed configuration.

10. The implantable spacer of claim 8, wherein the actuator is configured for rotation relative to the body to move the first and second arms from the deployed configuration to the undeployed configuration.

11. A system for implanting an implantable spacer, comprising:
the implantable spacer of claim 8;
an insertion instrument comprising a barrel and an outer clamping mechanism disposed at a distal end of the barrel, wherein the outer clamping mechanism is configured for clamping onto the body of the implantable spacer.

12. The system of claim 11, further comprising an inner shaft extendable out of the barrel of the insertion instrument and configured for coupling to the actuator of the implantable spacer for rotation of the actuator by rotation of the inner shaft.

13. The system of claim 11, wherein the insertion instrument comprises an operating lever coupled to the outer clamping mechanism and configured to operate to lock the outer clamping mechanism onto the body of the implantable spacer.

14. The system of claim 13, wherein body of the implantable spacer comprises lateral ribs to facilitate locking the outer clamping mechanism to the body of the implantable spacer.

15. An implantable spacer for placement between adjacent interspinous processes, the implantable spacer comprising:
a body defining a longitudinal axis;
a first arm and a second arm that are both coupled to the body and configured for rotation relative to the body, each of the first and second arms having a pair of extensions spaced apart from one another to define an opening between the extensions, the opening being configured to receive a spinous process;
an actuator extending from the body and configured for rotation relative to the body to move the first and second arms from an undeployed configuration in which the first and second arms are adjacent to each other to a deployed configuration in which the extensions of the first arm extend in an opposite direction to the extensions of the second arm.

16. The implantable spacer of claim 15, wherein the first and second arms retain a same shape in the deployed and undeployed configuration.

17. The implantable spacer of claim 15, wherein the actuator is configured for rotation relative to the body to move the first and second arms from the deployed configuration to the undeployed configuration.

18. A system for implanting an implantable spacer, comprising:
the implantable spacer of claim 15;
an insertion instrument comprising a barrel and an outer clamping mechanism disposed at a distal end of the barrel, wherein the outer clamping mechanism is configured for clamping onto the body of the implantable spacer.

19. The system of claim 18, further comprising an inner shaft extendable out of the barrel of the insertion instrument and configured for coupling to the actuator of the implantable spacer for rotation of the actuator by rotation of the inner shaft.

20. The system of claim 18, wherein the insertion instrument comprises an operating lever coupled to the outer clamping mechanism and configured to operate to lock the outer clamping mechanism onto the body of the implantable spacer.

* * * * *